(12) United States Patent
Gopalan et al.

(10) Patent No.: US 10,513,707 B2
(45) Date of Patent: Dec. 24, 2019

(54) TRANSGENIC LEGUMES

(71) Applicant: Arrowhead Center, Inc., Las Cruces, NM (US)

(72) Inventors: Champa Sengupta Gopalan, Las Cruces, NM (US); Mark Seger, Las Cruces, NM (US); Jose L. Ortega-Carranza, Las Cruces, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 0 days.

(21) Appl. No.: 15/907,141

(22) Filed: Feb. 27, 2018

(65) Prior Publication Data

US 2018/0195079 A1    Jul. 12, 2018

Related U.S. Application Data

(62) Division of application No. 15/232,687, filed on Aug. 9, 2016, now Pat. No. 9,902,966, which is a division of application No. 13/950,149, filed on Jul. 24, 2013, now Pat. No. 9,410,162.

(60) Provisional application No. 61/675,253, filed on Jul. 24, 2012.

(51) Int. Cl.
*C12N 15/82*    (2006.01)

(52) U.S. Cl.
CPC ....... *C12N 15/8241* (2013.01); *C12N 15/827* (2013.01); *C12N 15/8245* (2013.01); *C12N 15/8261* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 5,665,892 A * | 9/1997 | Van Assche | C07K 16/40 800/284 |
| 5,714,365 A | 2/1998 | Van Assche et al. | |
| 5,767,365 A | 6/1998 | Sonnewald | |
| 6,107,547 A | 8/2000 | Coruzzi et al. | |
| 6,288,240 B1 | 9/2001 | Martinez et al. | |
| 6,555,500 B1 | 4/2003 | Unkefer et al. | |
| 6,593,275 B1 | 7/2003 | Unkefer et al. | |
| RE38,446 E | 2/2004 | Van Assche et al. | |
| 6,723,898 B2 | 4/2004 | Sonnewald | |
| 6,756,218 B2 | 6/2004 | Allen et al. | |
| 6,831,040 B1 | 12/2004 | Unkefer et al. | |
| 6,864,405 B1 | 3/2005 | Coruzzi et al. | |
| 7,091,400 B2 | 8/2006 | Haigler et al. | |
| 7,176,009 B2 | 2/2007 | Allen et al. | |
| 7,989,677 B2 | 8/2011 | Tanksley et al. | |
| 8,551,917 B2 | 10/2013 | Unkefer et al. | |
| 2004/0077090 A1 | 4/2004 | Short | |
| 2005/0124010 A1 | 6/2005 | Short et al. | |
| 2007/0218556 A1 | 9/2007 | Harris et al. | |
| 2010/0115662 A1 | 5/2010 | Gupta et al. | |
| 2010/0170009 A1 | 7/2010 | Unkefer et al. | |
| 2010/0186121 A1 | 7/2010 | Unkefer et al. | |
| 2010/0263090 A1 | 10/2010 | Unkefer et al. | |
| 2011/0004961 A1 | 1/2011 | Unkefer et al. | |
| 2011/0030089 A1 | 2/2011 | Unkefer et al. | |
| 2012/0060235 A1 | 3/2012 | Privat et al. | |
| 2012/0144528 A1 | 6/2012 | Unkefer et al. | |
| 2013/0160158 A1 | 6/2013 | Gupta et al. | |
| 2013/0232641 A1 | 9/2013 | Unkefer et al. | |
| 2013/0239256 A1 | 9/2013 | Unkefer et al. | |
| 2014/0038824 A1 | 2/2014 | Unkefer et al. | |

FOREIGN PATENT DOCUMENTS

| | | |
|---|---|---|
| WO | 9216631 | 10/1992 |
| WO | 2011025515 A1 | 3/2011 |
| WO | 2011106794 A1 | 9/2011 |
| WO | 2012134906 A1 | 10/2012 |

OTHER PUBLICATIONS

Ortega et al, 2001, Plant Physiology, 126: 109-121.*
Fei, Houman, et al., "Overexpression of a soybean cystolic glutamine synthetase gene linked to organi-specific promoters in pea plants grown in difference concentrations of nitrate", Planta, 2003, 467-474.
Foyer, Christine H., et al., "Modulation of carbon and nitrogen metabolism in transgenic plants with a view to improved biomass production", Biochemical Society Transactions, 1994, 909-915.
Gallais, A., et al., "Genetic Variation and Selection for Nitrogen Use Efficiency in Maize: A Synthesis", Maydica, 2005, 531-547.
Hirel, Bertrand, et al., "Forcing expression of a soybean root glutamine synthetase gene in tobacco leaves induces a native gene encoding cytosolic enzyme", Plant Molecular Biology, 1992, 207-218.
Laporte, Marianne M., et al., "Promoter strength and tissue specificity effects on growth of tomato plants transformed with maize sucrose-phosphate synthase", Planta, 2001, 817=822.
Luis-Ortega, Jose, et al., "Regulatory Mechanisms Underlying Posttranscriptional Regulation of Cytosolic Glutamine Synthetase in Alfalfa", Poster, 2009.

(Continued)

*Primary Examiner* — Jason Deveau Rosen
(74) *Attorney, Agent, or Firm* — Peacock Law P.C.; Issac Estrada; Deborah A. Peacock

(57) ABSTRACT

Embodiments of the present invention comprise altering the biosynthesis and accumulation of sucrose in legumes by transforming the plants with the sucrose phosphate synthase (SPS) gene of maize, and closely related regulatory genes. Embodiments of the present invention further comprise altering the assimilation of nitrogen in legumes by transforming the plants with the glutamine synthetase (GS) gene of soybean, and closely related regulatory genes. Embodiments of the present invention further comprise transforming legume plants with both SPS and GS genes. In addition, embodiments of the present invention relate to enhancing expression of transgenes through the 5' UTR of the *glycine max* (soybean) cytosolic glutamine synthetase (Gmgln$\beta_1$) gene.

12 Claims, 51 Drawing Sheets

Specification includes a Sequence Listing.

(56) References Cited

OTHER PUBLICATIONS

Miao, Guo-Hua, et al., "Ammonia-Regulated Expression of a Soybean Gene Encoding Cytosolic Glutamine Synthetase in Transgenic Lotus corniculatus", The Plant Cell, Jan. 1991, 11-22.

Ortega, Jose Luis, et al., "Constitutive Overexpression of Cystosolic Glutamine Synthetase (GS1) Gene in Transgenic Alfalfa DEmonstrates that GS1 May be Regulated at the Level of RNA Stability and Protein Turnover", Plant Physiology, vol. 126, American Society of Plan Biologists, May 2001, 109-121.

Ortega, Jose L., et al., "The 3' untranslated region of a soybean cytosolic glutamine synthetase (GS1) affects transcript stability and protein accumulation in transgenic alfalfa", The Plant Journal, 2006, 832-846.

Seger, Mark, "Manipulation of sucrose phosphate synthase (SPS) activity in *Medicago sativa* (Alfalfa)", http:www.nmspacegrant.com/files/tiny_mce/file_manager/fellowships_research/MarkSeger-2009.pdf, Oct. 23, 2009.

\* cited by examiner

GSβ150/GSβ153

-65 gaattcTCTAAAAGAGATCTTTTTCTGCTCTTTGAAGAAAGAACG -21
    Eco RI              oligopyrimidine track                SEQ ID NO. 17
-20 GTCTTTGCTTGATTTTGGAGATGTCTCTGCTCTCagatct +20
                                        Bgl II

GSβ100/GSβ103

-18 CACGGGGGACTCTTGACCATGTCTCTGCTCTCagatct +20 SEQ ID NO. 18
              Kozak            Bgl II

FIG. 32B

SEQ ID NO. 19

SEQ ID NO. 20

SEQUENCE LISTING

```
<160> NUMBER OF SEQ ID NOS: 20

<210> SEQ ID NO 1
<211> LENGTH: 3509
<212> TYPE: DNA
<213> ORGANISM: Zea mays

<400> SEQUENCE: 1
```

```
gaattccggc gtgggcgctg ggctagtgct cccgcagcga gcgatctgag agaacggtag    60
agttccggcc gggcgcgcgg gagaggagga gggtcgggcg gggaggatcc gatggccggg   120
aacgagtgga tcaatgggta cctggaggcg atcctcgaca gccacacctc gtcgcggggt   180
gccggcggcg cgcggcggcg ggggaccccc aggtcgccga cgaaggcggc gagccccgc   240 ggcgcgcaca tgaacttcaa cccctcgcac tacttcgtcg aggaggtggt caagggcgtc   300
gacgagagcg acctccaccg gacgtggatc aaggtcgtcg ccacccgcaa cgcccgcgag   360
cgcagcacca ggctcgagaa catgtgctgg cggatctggc acctcgcgcg caagaagaag   420
cagctggagc tggagggcat ccagagaatc tcggcaagaa ggaaggaaca ggagcaggtg   480
cgtcgtgagg cgacggagga cctggccgag gatctgtcag aaggcgagaa gggagacacc   540
atcggcgagc ttgcgccggt tgagacgacc aagaagaagt tccagaggaa cttctctgac   600
cttaccgtct ggtctgacga caataaggag aagaagcttt acattgtgct catcagcgtg   660
catggtcttg ttcgtggaga aaacatggaa ctaggtcgtg attctgatac aggtggccag   720
gtgaaatatg tggtcgaact tgcaagagcg atgtcaatga tgcctggagt gtacagggtg   780
gacctcttca ctcgtcaagt gtcatctcct gacgtggact ggagctacgg tgagccaacc   840
gagatgttat gcgccggttc caatgatgga gaggggatgg gtgagagtgg cggagcctac   900
attgtgcgca taccgtgtgg gccgcgggat aaatacctca agaaggaagc gttgtggcct   960
tacctccaag agtttgtcga tggagccctt gcgcatatcc tgaacatgtc caaggctctg  1020
ggagagcagg ttggaaatgg gaggccagta ctgccttacg tgatacatgg cactatgcc   1080 gatgctggag atgttgctgc tctcctttct ggtgcgctga atgtgccaat ggtgctcact  1140
ggccactcac ttgggaggaa caagctggaa caactgctga gcaagggcg catgtccaag  1200 gaggagatcg attcgacata caagatcatg aggcgtatcg agggtgagga gctggccctg  1260
gatgcgtcag agcttgtaat cacgagcaca aggcaggaga ttgatgagca gtggggattg  1320
tacgatggat ttgatgtcaa gcttgagaaa gtgctgaggg cacgggcgag gcgcggggtt  1380
agctgccatg tcgttacat gcctaggatg gtggtgattc ctccgggaat ggatttcagc  1440
aatgttgtag ttcatgaaga cattgatggg gatggtgacg tcaaagatga tatcgttggt  1500
ttggagggtg cctcacccaa gtcaatgccc ccaatttggg ccgaagtgat gcggttcctg  1560
accaaccctc acaagccgat gatcctggcg ttatcaagac cagacccgaa gaagaacatc  1620
actaccctcg tcaaagcgtt tggagagtgt cgtccactca gggaacttgc aaaccttact  1680
ctgatcatgg gtaacagaga tgacatcgac gacatgtctg ctggcaatgc cagtgtcctc  1740
accacagttc tgaagctgat tgacaagtat gatctgtacg gaagcgtggc gttccctaag  1800
catcacaatc aggctgacgt cccggagatc tatcgcctcg cggccaaaat gaagggcgtc  1860
ttcatcaacc ctgctctcgt tgagccgttt ggtctcaccc tgatcgaggc tgcggcacac  1920
ggactcccga tagtcgctac caagaatggt ggtccggtcg acattacaaa tgcattaaac  1980
aacggactgc tcgttgaccc acacgaccag aacgccatcg ctgatgcact gctgaagctt  2040
gtggcagaca agaacctgtg gcaggaatgc cggagaaacg ggctgcgcaa catccacctc  2100
tactcatggc cggagcactg ccgcacttac ctcaccaggg tggccgggtg ccggttaagg  2160
aacccgaggt ggctgaagga cacaccagca gatgccggag ccgatgagga ggagttcctg  2220
gaggattcca tggacgctca ggacctgtca ctccgtctgt ccatcgacgg tgagaagagc  2280
tcgctgaaca ctaacgatcc actgtggttc gaccccagg atcaagtgca agagatcatg  2340
```

```
aacaacatca agcagtcgtc agcgcttcct ccgtccatgt cctcagtcgc agccgagggc    2400
acaggcagca ccatgaacaa atacccactc ctgcgccggc gccggcgctt gttcgtcata    2460
gctgtggact gctaccagga cgatggccgt gctagcaaga agatgctgca ggtgatccag    2520
gaagttttca gagcagtccg atcggactcc cagatgttca agatctcagg gttcacgctg    2580
tcgactgcca tgccgttgtc cgagacactc cagcttctgc agctcggcaa gatcccagcg    2640
accgacttcg acgccctcat ctgtggcagc ggcagcgagg tgtactatcc tggcacggcg    2700
aactgcatgg acgctgaagg aaagctgcgc ccagatcagg actatctgat gcacatcagc    2760
caccgctggt cccatgacgg cgcgaggcag accatagcga agctcatggg cgctcaggac    2820
ggttcaggcg acgctgtcga gcaggacgtg gcgtccagta atgcacactg tgtcgcgttc    2880
ctcatcaaag ccccccaaaa ggtgaaaacg tcgatgaga tgaggggagcg gctgaggatg    2940 cgtggtctcc gctgccacat catgtactgc aggaactcga caaggcttca ggttgtccct    3000
ctgctagcat caaggtcaca ggcactcagg tatctttccg tgcgctgggg cgtatctgtg    3060
gggaacatgt atctgatcac cggggaacat ggcgacaccg atctagagga gatgctatcc    3120
gggctacaca agaccgtgat cgtccgtggc gtcaccgaga agggttcgga agcactggtg    3180
aggagcccag gaagctacaa gagggacgat gtcgtcccgt ctgagacccc cttggctgcg    3240
tacacgactg gtgagctgaa ggccgacgag atcatgcggg ctctgaagca agtctccaag    3300
acttccagcg gcatgtgaat ttgatgcttc ttttacattt tgtccttttc ttcactgcta    3360
tataaaataa gttgtgaaca gtaccgcggg tgtgtatata tatattgcag tgacaaataa    3420
aacaggacac tgctaactat actggtgaat atacgactgt caagattgta tgctaagtac    3480
tccatttctc aatgtatcaa tcggaattc                                     3509

<210> SEQ ID NO 2
<211> LENGTH: 1403
<212> TYPE: DNA
<213> ORGANISM: Glycine max

<400> SEQUENCE: 2
tctaaaagag atcttttttct gctctttgaa gaaagaaggg tctttgcttg attttggaga      60
tgtctctgct ctcagatctc atcaacctta acctctccga taccaccgag aaggtgatcg     120
cagagtacat atggatcggt ggatcaggaa tggacctgag gagcaaagca aggactctcc     180
caggaccagt tagcgaccct tcagagcttc ccaagtggaa ctatgatggt tccagcacag     240
gtcaagctcc tggtgaagac agtgaagtga ttttataccc acaagccatt tcagggatc     300 cattcagaag gggtaacaat atcttggtta tctgtgatgc ctacactcct gctggagaac     360
ctattcccac taacaagagg cacgctgctg ccaaggtttt cagccatcct gatgttgttg     420
ctgaagtgcc atggtacggt attgaacaag aatacacctt gttgcagaaa gatatccaat     480
ggcctcttgg gtggcctgtt ggtggttttcc ctggacctca gggtccatac tactgtggtg     540
ttggcgctga caaggctttt ggccgtgaca ttgttgacgc acactacaaa gcctgtattt     600
atgctggcat caacatcagt ggaattaatg gagaagtgat gcccggtcag tgggaattcc     660
aagttggacc ttcagttgga atctcagctg gtgatgagat tgggcagct cgttacatct     720 tggagaggat cactgagatt gctggtgtgg tggtttcctt tgaccccaag ccaattaagg     780
gtgattggaa tggtgctggt gctcacacaa actacagcac caagtccatg agaagatg     840 gtggctatga agtgatcaaa gcagcaattg acaagttggg gaagaagcac aaggagcaca    900
ttgctgctta tggagaaggc aacgaacgtc gtttgacagg acgccacgaa accgctgaca    960
```

```
tcaacacctt cttatgggga gttgcaaacc gtggagcttc tgttagggtt gggagagaca   1020
cagagaaagc agggaaggga tattttgagg acagaaggcc agcttccaac atggacccat   1080
acgtggttac ttccatgatt gcagacacaa ccattctgtg gaagccatga gcaaaacctg   1140
catgttttct ccctttggat ggaaggaac agttatgctt ttcttagtag gatttggtct   1200
ctctctcttt ttacctttg attggtacta tggttggtgc cttgttggtt ggtgcaacta   1260
actggcaagg gttgttcatt gttttcttct attcctttcc ctcgttttcc gattgttaca   1320
atgacaataa tttaatggtt attatcagtc ttgaacaaag aaatgctgat tgtgaagtat   1380
aataataata tatgaaattg ccg                                          1403

<210> SEQ ID NO 3
<211> LENGTH: 59
<212> TYPE: DNA
<213> ORGANISM: Glycine max

<400> SEQUENCE: 3
tctaaaagag atctttttct gctctttgaa gaaagaaggg tctttgcttg attttggag   59

<210> SEQ ID NO 4
<211> LENGTH: 1068
<212> TYPE: PRT
<213> ORGANISM: Zea mays

<400> SEQUENCE: 4

Met Ala Gly Asn Glu Trp Ile Asn Gly Tyr Leu Glu Ala Ile Leu Asp
1               5                   10                  15

Ser His Thr Ser Ser Arg Gly Ala Gly Gly Gly Gly Gly Gly Gly Asp
            20                  25                  30

Pro Arg Ser Pro Thr Lys Ala Ala Ser Pro Arg Gly Ala His Met Asn
        35                  40                  45

Phe Asn Pro Ser His Tyr Phe Val Glu Glu Val Val Lys Gly Val Asp
    50                  55                  60

Glu Ser Asp Leu His Arg Thr Trp Ile Lys Val Val Ala Thr Arg Asn
65                  70                  75                  80

Ala Arg Glu Arg Ser Thr Arg Leu Glu Asn Met Cys Trp Arg Ile Trp
                85                  90                  95

His Leu Ala Arg Lys Lys Lys Gln Leu Glu Leu Glu Gly Ile Gln Arg
            100                 105                 110

Ile Ser Ala Arg Arg Lys Glu Gln Glu Gln Val Arg Arg Glu Ala Thr
        115                 120                 125

Glu Asp Leu Ala Glu Asp Leu Ser Glu Gly Glu Lys Gly Asp Thr Ile
    130                 135                 140

Gly Glu Leu Ala Pro Val Glu Thr Thr Lys Lys Lys Phe Gln Arg Asn
145                 150                 155                 160

Phe Ser Asp Leu Thr Val Trp Ser Asp Asn Lys Glu Lys Lys Leu
                165                 170                 175

Tyr Ile Val Leu Ile Ser Val His Gly Leu Val Arg Gly Glu Asn Met
            180                 185                 190

Glu Leu Gly Arg Asp Ser Asp Thr Gly Gly Gln Val Lys Tyr Val Val
        195                 200                 205

Glu Leu Ala Arg Ala Met Ser Met Met Pro Gly Val Tyr Arg Val Asp
    210                 215                 220

Leu Phe Thr Arg Gln Val Ser Ser Pro Asp Val Asp Trp Ser Tyr Gly
225                 230                 235                 240
```

-continued

```
Glu Pro Thr Glu Met Leu Cys Ala Gly Ser Asn Asp Gly Glu Gly Met
                245                 250                 255

Gly Glu Ser Gly Gly Ala Tyr Ile Val Arg Ile Pro Cys Gly Pro Arg
            260                 265                 270

Asp Lys Tyr Leu Lys Lys Glu Ala Leu Trp Pro Tyr Leu Gln Glu Phe
        275                 280                 285

Val Asp Gly Ala Leu Ala His Ile Leu Asn Met Ser Lys Ala Leu Gly
    290                 295                 300

Glu Gln Val Gly Asn Gly Arg Pro Val Leu Pro Tyr Val Ile His Gly
305                 310                 315                 320

His Tyr Ala Asp Ala Gly Asp Val Ala Ala Leu Leu Ser Gly Ala Leu
                325                 330                 335

Asn Val Pro Met Val Leu Thr Gly His Ser Leu Gly Arg Asn Lys Leu
                340                 345                 350

Glu Gln Leu Leu Lys Gln Gly Arg Met Ser Lys Glu Glu Ile Asp Ser
            355                 360                 365

Thr Tyr Lys Ile Met Arg Arg Ile Glu Gly Glu Leu Ala Leu Asp
    370                 375                 380

Ala Ser Glu Leu Val Ile Thr Ser Thr Arg Gln Glu Ile Asp Glu Gln
385                 390                 395                 400

Trp Gly Leu Tyr Asp Gly Phe Asp Val Lys Leu Glu Lys Val Leu Arg
                405                 410                 415

Ala Arg Ala Arg Arg Gly Val Ser Cys His Gly Arg Tyr Met Pro Arg
                420                 425                 430

Met Val Val Ile Pro Pro Gly Met Asp Phe Ser Asn Val Val Val His
                435                 440                 445

Glu Asp Ile Asp Gly Asp Gly Asp Val Lys Asp Ile Val Gly Leu
450                 455                 460

Glu Gly Ala Ser Pro Lys Ser Met Pro Pro Ile Trp Ala Glu Val Met
465                 470                 475                 480

Arg Phe Leu Thr Asn Pro His Lys Pro Met Ile Leu Ala Leu Ser Arg
                485                 490                 495

Pro Asp Pro Lys Lys Asn Ile Thr Thr Leu Val Lys Ala Phe Gly Glu
            500                 505                 510

Cys Arg Pro Leu Arg Glu Leu Ala Asn Leu Thr Leu Ile Met Gly Asn
            515                 520                 525

Arg Asp Asp Ile Asp Asp Met Ser Ala Gly Asn Ala Ser Val Leu Thr
        530                 535                 540

Thr Val Leu Lys Leu Ile Asp Lys Tyr Asp Leu Tyr Gly Ser Val Ala
545                 550                 555                 560

Phe Pro Lys His His Asn Gln Ala Asp Val Pro Glu Ile Tyr Arg Leu
                565                 570                 575

Ala Ala Lys Met Lys Gly Val Phe Ile Asn Pro Ala Leu Val Glu Pro
            580                 585                 590

Phe Gly Leu Thr Leu Ile Glu Ala Ala His Gly Leu Pro Ile Val
    595                 600                 605

Ala Thr Lys Asn Gly Gly Pro Val Asp Ile Thr Asn Ala Leu Asn Asn
    610                 615                 620

Gly Leu Leu Val Asp Pro His Asp Gln Asn Ala Ile Ala Asp Ala Leu
625                 630                 635                 640

Leu Lys Leu Val Ala Asp Lys Asn Leu Trp Gln Glu Cys Arg Arg Asn
                645                 650                 655
```

```
Gly Leu Arg Asn Ile His Leu Tyr Ser Trp Pro Glu His Cys Arg Thr
            660                 665                 670

Tyr Leu Thr Arg Val Ala Gly Cys Arg Leu Arg Asn Pro Arg Trp Leu
            675                 680                 685

Lys Asp Thr Pro Ala Asp Ala Gly Ala Asp Glu Glu Phe Leu Glu
    690                 695                 700

Asp Ser Met Asp Ala Gln Asp Leu Ser Leu Arg Leu Ser Ile Asp Gly
705                 710                 715                 720

Glu Lys Ser Ser Leu Asn Thr Asn Asp Pro Leu Trp Phe Asp Pro Gln
                725                 730                 735

Asp Gln Val Gln Lys Ile Met Asn Asn Ile Lys Gln Ser Ser Ala Leu
        740                 745                 750

Pro Pro Ser Met Ser Ser Val Ala Ala Glu Gly Thr Gly Ser Thr Met
            755                 760                 765

Asn Lys Tyr Pro Leu Leu Arg Arg Arg Arg Leu Phe Val Ile Ala
770                 775                 780

Val Asp Cys Tyr Gln Asp Asp Gly Arg Ala Ser Lys Lys Met Leu Gln
785                 790                 795                 800

Val Ile Gln Glu Val Phe Arg Ala Val Arg Ser Asp Ser Gln Met Phe
                805                 810                 815

Lys Ile Ser Gly Phe Thr Leu Ser Thr Ala Met Pro Leu Ser Glu Thr
            820                 825                 830

Leu Gln Leu Leu Gln Leu Gly Lys Ile Pro Ala Thr Asp Phe Asp Ala
            835                 840                 845

Leu Ile Cys Gly Ser Gly Ser Glu Val Tyr Tyr Pro Gly Thr Ala Asn
850                 855                 860

Cys Met Asp Ala Glu Gly Lys Leu Arg Pro Asp Gln Asp Tyr Leu Met
865                 870                 875                 880

His Ile Ser His Arg Trp Ser His Asp Gly Ala Arg Gln Thr Ile Ala
                885                 890                 895

Lys Leu Met Gly Ala Gln Asp Gly Ser Gly Asp Ala Val Glu Gln Asp
            900                 905                 910

Val Ala Ser Ser Asn Ala His Cys Val Ala Phe Leu Ile Lys Asp Pro
            915                 920                 925

Gln Lys Val Lys Thr Val Asp Glu Met Arg Glu Arg Leu Arg Met Arg
    930                 935                 940

Gly Leu Arg Cys His Ile Met Tyr Cys Arg Asn Ser Thr Arg Leu Gln
945                 950                 955                 960

Val Val Pro Leu Leu Ala Ser Arg Ser Gln Ala Leu Arg Tyr Leu Ser
                965                 970                 975

Val Arg Trp Gly Val Ser Val Gly Asn Met Tyr Leu Ile Thr Gly Glu
            980                 985                 990

His Gly Asp Thr Asp Leu Glu Glu Met Leu Ser Gly Leu His Lys Thr
        995                 1000                1005

Val Ile Val Arg Gly Val Thr Glu Lys Gly Ser Glu Ala Leu Val
    1010                1015                1020

Arg Ser Pro Gly Ser Tyr Lys Arg Asp Asp Val Val Pro Ser Glu
1025                1030                1035

Thr Pro Leu Ala Ala Tyr Thr Thr Gly Glu Leu Lys Ala Asp Glu
    1040                1045                1050

Ile Met Arg Ala Leu Lys Gln Val Ser Lys Thr Ser Ser Gly Met
    1055                1060                1065
```

```
<210> SEQ ID NO 5
<211> LENGTH: 356
<212> TYPE: PRT
<213> ORGANISM: Glycine max

<400> SEQUENCE: 5

Met Ser Leu Leu Ser Asp Leu Ile Asn Leu Asn Leu Ser Asp Thr Thr
1               5                   10                  15

Glu Lys Val Ile Ala Glu Tyr Ile Trp Ile Gly Gly Ser Gly Met Asp
            20                  25                  30

Leu Arg Ser Lys Ala Arg Thr Leu Pro Gly Pro Val Ser Asp Pro Ser
        35                  40                  45

Glu Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Arg Asp
65                  70                  75                  80

Pro Phe Arg Arg Gly Asn Asn Ile Leu Val Ile Cys Asp Ala Tyr Thr
                85                  90                  95

Pro Ala Gly Glu Pro Ile Pro Thr Asn Lys Arg His Ala Ala Ala Lys
            100                 105                 110

Val Phe Ser His Pro Asp Val Val Ala Glu Val Pro Trp Tyr Gly Ile
        115                 120                 125

Glu Gln Glu Tyr Thr Leu Leu Gln Lys Asp Ile Gln Trp Pro Leu Gly
    130                 135                 140

Trp Pro Val Gly Gly Phe Pro Gly Pro Gln Gly Pro Tyr Tyr Cys Gly
145                 150                 155                 160

Val Gly Ala Asp Lys Ala Phe Gly Arg Asp Ile Val Asp Ala His Tyr
                165                 170                 175

Lys Ala Cys Ile Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

Ser Ala Gly Asp Glu Ile Trp Ala Ala Arg Tyr Ile Leu Glu Arg Ile
    210                 215                 220

Thr Glu Ile Ala Gly Val Val Val Ser Phe Asp Pro Lys Pro Ile Lys
225                 230                 235                 240

Gly Asp Trp Asn Gly Ala Gly Ala His Thr Asn Tyr Ser Thr Lys Ser
                245                 250                 255

Met Arg Glu Asp Gly Gly Tyr Glu Val Ile Lys Ala Ala Ile Asp Lys
            260                 265                 270

Leu Gly Lys Lys His Lys Glu His Ile Ala Ala Tyr Gly Glu Gly Asn
        275                 280                 285

Glu Arg Arg Leu Thr Gly Arg His Glu Thr Ala Asp Ile Asn Thr Phe
    290                 295                 300

Leu Trp Gly Val Ala Asn Arg Gly Ala Ser Val Arg Val Gly Arg Asp
305                 310                 315                 320

Thr Glu Lys Ala Gly Lys Gly Tyr Phe Glu Asp Arg Arg Pro Ala Ser
                325                 330                 335

Asn Met Asp Pro Tyr Val Val Thr Ser Met Ile Ala Asp Thr Thr Ile
            340                 345                 350

Leu Trp Lys Pro
        355

<210> SEQ ID NO 6
<211> LENGTH: 37
```

```
<212> TYPE: DNA
<213> ORGANISM: Artificial sequence
<220> FEATURE:
<223> OTHER INFORMATION: Glycine max with Cauliflower mosaic virus

<400> SEQUENCE: 6
gagaattccc gtgttctctc caaatgaaat gaacttc                           37

<210> SEQ ID NO 7
<211> LENGTH: 39
<212> TYPE: DNA
<213> ORGANISM: Artificial sequence
<220> FEATURE:
<223> OTHER INFORMATION: Glycine max with Cauliflower mosaic virus

<400> SEQUENCE: 7
agatctgaga gcgagacatg gtcaagagtc ccccgtgtt                         39

<210> SEQ ID NO 8
<211> LENGTH: 23
<212> TYPE: DNA
<213> ORGANISM: Artificial sequence
<220> FEATURE:
<223> OTHER INFORMATION: Glycine max with Cauliflower mosaic virus

<400> SEQUENCE: 8
aagcttcatg gagtcaaaga ttc                                          23

<210> SEQ ID NO 9
<211> LENGTH: 33
<212> TYPE: DNA
<213> ORGANISM: Artificial sequence
<220> FEATURE:
<223> OTHER INFORMATION: Glycine max with Cauliflower mosaic virus

<400> SEQUENCE: 9
cccgggatcg ttcaaacatt tggcaataaa gtt                               33

<210> SEQ ID NO 10
<211> LENGTH: 34
<212> TYPE: DNA
<213> ORGANISM: Artificial sequence
<220> FEATURE:
<223> OTHER INFORMATION: Glycine max with Cauliflower mosaic virus

<400> SEQUENCE: 10
gagctctgca gcccgatcta gtaacataga cacc                              34

<210> SEQ ID NO 11
<211> LENGTH: 34
<212> TYPE: DNA
<213> ORGANISM: Artificial sequence
<220> FEATURE:
<223> OTHER INFORMATION: Glycine max with Cauliflower mosaic virus

<400> SEQUENCE: 11
ccatggctcc aaaatcaagc aaagaccctt cttt                              34

<210> SEQ ID NO 12
<211> LENGTH: 41
<212> TYPE: DNA
<213> ORGANISM: Artificial sequence
<220> FEATURE:
<223> OTHER INFORMATION: Glycine max with Cauliflower mosaic virus

<400> SEQUENCE: 12
```
ggtgaccagc tcgaatttcc ccgatcgttc aaacatttgg c 41

<210> SEQ ID NO 13
<211> LENGTH: 27
<212> TYPE: DNA
<213> ORGANISM: Nicotiana tabacum

<400> SEQUENCE: 13
ccagtgagca gagtgacgag gaagctt 27

<210> SEQ ID NO 14
<211> LENGTH: 26
<212> TYPE: DNA
<213> ORGANISM: Nicotiana tabacum

<400> SEQUENCE: 14
cacgggaatt ctctaaaaga gatctt 26

<210> SEQ ID NO 15
<211> LENGTH: 22
<212> TYPE: DNA
<213> ORGANISM: Nicotiana tabacum

<400> SEQUENCE: 15
aacacggggg actcttgacc at 22

<210> SEQ ID NO 16
<211> LENGTH: 281
<212> TYPE: RNA
<213> ORGANISM: Artificial sequence
<220> FEATURE:
<223> OTHER INFORMATION: Glycine max with Cauliflower mosaic virus

<400> SEQUENCE: 16
ugagcaaaac cugcauguuu ucucccuuuu gauggaaagg aacaguuaug cuuuucuuag 60
uaggauuugg ucucucucuc uuuuuaccuu uugauuggua cuaugguugg ugccuuguug 120
guuggugcaa cuaacuggca aggguuguuc auuguuuucu ucuauuccuu ucccucguuu 180
uccgauuguu acaaugacaa uaauuuaaug guuauuauca gucuugaaca aagaaaugcu 240
gauugugaag uauaauaaua auauaugaaa uugccggaau c 281

<210> SEQ ID NO 17
<211> LENGTH: 85
<212> TYPE: DNA
<213> ORGANISM: Artificial sequence
<220> FEATURE:
<223> OTHER INFORMATION: Glycine max with Cauliflower mosaic virus

<400> SEQUENCE: 17
gaattctcta aaagagatct ttttctgctc tttgaagaaa gaagggtctt tgcttgattt 60
tggagatgtc tctgctctca gatct 85

<210> SEQ ID NO 18
<211> LENGTH: 38
<212> TYPE: DNA
<213> ORGANISM: Artificial sequence
<220> FEATURE:
<223> OTHER INFORMATION: Glycine max with Cauliflower mosaic virus

<400> SEQUENCE: 18
cacgggggac tcttgaccat gtctctgctc tcagatct 38

```
<210> SEQ ID NO 19
<211> LENGTH: 85
<212> TYPE: RNA
<213> ORGANISM: Artificial sequence
<220> FEATURE:
<223> OTHER INFORMATION: Glycine max with Cauliflower mosaic virus

<400> SEQUENCE: 19
gaauucucua aaagagaucu uuuucugcuc uuugaagaaa gaagggucuu ugcuugauuu      60
uggagauguc ucugcucuca gaucu                                           85

<210> SEQ ID NO 20
<211> LENGTH: 86
<212> TYPE: DNA
<213> ORGANISM: Artificial sequence
<220> FEATURE:
<223> OTHER INFORMATION: Glycine max with Cauliflower mosaic virus

<400> SEQUENCE: 20 ggatcccag gaattctcta aaagagatct ttttctgctc tttgaagaaa gaagggtctt      60
tgcttgattt tggagatgtc tctgct                                          86
```

TRANSGENIC LEGUMES

CROSS-REFERENCE TO RELATED APPLICATIONS

This application is a divisional of U.S. patent application Ser. No. 15/232,687 filed Aug. 9, 2016, entitled "METHOD OF ENHANCING TRANSLATION OF FOREIGN GENES IN PLANTS", issuing as U.S. Pat. No. 9,902,966 on Feb. 27, 2018, which is a divisional of U.S. patent application Ser. No. 13/950,149 filed Jul. 24, 2013, entitled "TRANSGENIC LEGUMES", issued as U.S. Pat. No. 9,410,162 on Aug. 9, 2016, which claims priority to and the benefit of the filing of U.S. Provisional Patent Application Ser. No. 61/675,253, entitled "TRANSGENIC LEGUMES", filed on Jul. 24, 2012, and the specifications and claims of which are incorporated herein by reference.

STATEMENT REGARDING FEDERALLY SPONSORED RESEARCH OR DEVELOPMENT

This invention was made with government support under USDA grant agreement #2007-35318-18483, and Hatch grants with accession numbers 0198573 and 0197919. The government has certain rights in the invention.

REFERENCE TO A SEQUENCE LISTING, A TABLE, OR COMPUTER PROGRAM

Applicant hereby submits a sequence listing as a text file titled SEQ-LISTING-DIV-2.txt created on Feb. 27, 2018 having 23 kbytes that is ASCII compliant and is incorporated herein by reference.

BACKGROUND OF THE INVENTION

Field of the Invention (Technical Field)

The present invention relates to the use of the sucrose phosphate synthase (SPS) gene of maize, and closely related regulatory genes, for altering the biosynthesis and accumulation of sucrose in alfalfa and other legumes. The present invention further relates to transgenic constructs containing the SPS and allied regulatory genes, for use in the transformation of alfalfa and other legumes, and it also relates to transgenic plants containing such constructs. The present invention also relates to the use of the glutamine synthetase (GS) gene of soybean, and closely related regulatory genes, for altering the assimilation of nitrogen in alfalfa and other legumes. The present invention further relates to transgenic constructs containing the GS1 gene and allied regulatory genes, for use in the transformation of alfalfa and other legumes, and it also relates to transgenic plants containing such constructs.

Description of Related Art

Sucrose phosphate synthase (SPS) is an enzyme used in the synthesis of sucrose in plants. SPS is involved in the synthesis of sucrose by the transfer of glucosyl moiety from UDP-glucose to fructose-6-phosphate, which is dephosphorylated by the action of sucrose-6-phosphate phosphatase (SPP) to yield sucrose. Sucrose is a stable product of photosynthesis that is transported from the photosynthetic tissues via the phloem into heterotrophic tissues which includes the root nodules in leguminous plants. The root nodule is an organ formed as a result of a symbiotic association of legume plants with a soil bacteria, *Rhizobium*. The root nodule is the site where the symbiont can convert free nitrogen into $NH_3$, which is then assimilated by host encoded enzymes. The symbiont is contained in a membrane bound vesicle called the symbiosome and this membrane is called the peribacteroid membrane which contains many host encoded proteins. The enzyme nitrogenase in the bacteria (symbiont), catalyzes ATP dependent reduction of $N_2$ to $NH_3$ in infected cells of the root nodules. Any ammonium produced is exported out through the peribacteroid membrane into the cytosol, where it is assimilated via host encoded enzymes glutamine synthetase (GS) and glutamate synthase to produce glutamine and glutamate.

The nodules are primarily dependent on the import and metabolism of sucrose to fuel the $N_2$ fixation process. Sucrose is metabolized initially by sucrose synthase (SuSy) (and to a lesser extent vacuolar invertase) and thereafter, via glycolysis to phosphoenolpyruvate (PEP). The products of sucrose metabolism have two major functions in the nodules. The first is to provide a substrate that can cross the peribacteroid membrane and be oxidized to provide the ATP and reducing power for the fixation of $N_2$. The second is its involvement in the assimilation of ammonia which is produced by the bacteria, the synthesis of nitrogen products and their export from the nodule via the xylem. The high carbon cost for the alfalfa/*Rhizobium* interaction renders the nodule a strong sink for sucrose. Furthermore, sucrose is stored in high concentrations in nodules during the photoperiod and utilized in the dark period (at night).

Sucrose plays a role in the nodules. SPS is encoded by a small multigene family. The family members, besides showing differences in tissue-specific expression, are also subject to differential regulation at the posttranslational level via phosphorylation. In alfalfa, SPSB gene shows leaf-specific expression and SPSA gene, though nodule-enhanced, exhibits constitutive expression. Embodiments of the present invention comprise genetically engineered alfalfa that expresses a maize SPSB gene driven by the CaMV35S promoter. These transformants show increased nodulation and $N_2$-fixation and overall increased N content at the whole plant level compared to control alfalfa plants. Moreover, the transformants show late flowering, shorter internodes, and intense green coloration mimicking the phenotypes seen in super/hypernodulating legumes.

Glutamine synthetase (GS) plays a central role in nitrogen metabolism in all plants. GS catalyzes the ATP dependent condensation of ammonia with glutamate, to yield glutamine. Plant GS is an octamer and occurs as a number of isoenzyme forms and these GS isoforms are located either in the cytosol (GS1) or chloroplast/plastid (GS2). GS1 represents a key component of nitrogen use efficiency and yield. Increase in GS1 activity is accompanied by a substantial improvement in plant performance.

Regulation of expression of a soybean (*Glycine max*) GS1 gene (Gmglnβ1) driven by a constitutive promoter (CaMV 35S) in transgenic plants typically occurs at a post-transcriptional level. The post-transcriptional regulatory step of the Gmglnβ1 and also the GS1 genes from alfalfa, is at the level of transcript turnover, mediated by their 3'UTR. Gmglnβ1 was investigated to determine if it is also subject to other modes of regulation by testing the role of its 5'UTR in the regulation of gene expression.

The synthesis of glutamine is a first step for the synthesis of all other essential nitrogenous compounds contained in the cells. GS also plays a crucial role in removing ammonia which is toxic to the cells, but at the same time GS levels and activity have to be fine-tuned to maintain a balance between the rates of amino acid biosynthesis and the cellular C skeletons and ATP levels, since they can be depleted by GS activity. GS in bacteria is highly regulated in vivo by transcriptional and post-translational mechanisms including adenylylation and metabolic feedback inhibition. The glutamine/α-ketoglutarate ratio and the adenylate energy charge are critical in the control of GS activity in bacteria. The glutamine/α-ketoglutarate ratio is also important for the control of nitrogen assimilation in plants. GS in plants, as in bacteria, is also regulated at multiple levels.

Analysis of the translation process of eukaryotic mRNAs has shown that the 5'UTR plays an important role in translation initiation by its secondary structure; the context of AUG codon; and the existence of AUG or upstream open-reading frames. The 5'UTR is also the target for the binding of microRNAs that cause translational repression or enhance translation. There are also some reports of the 5'UTR having a role in mRNA stabilization, though this is usually an attribute of sequences in the 3'UTR.

To demonstrate the role of the 5'UTR of the Gmglnβ1 gene in the regulation of its expression, a series of gene constructs were made with the Gmglnβ1 driven by the CaMV 35S promoter, with and without the 5' and 3' UTRs and tested for their expression by agroinfiltration in tobacco (*Nicotiana tabacum* cv *Xanthi*) leaves, at both the transcript and protein levels. Transient expression through agroinfiltration is a relatively easy procedure known to be effective in analyzing expression of transgenes. Results showed that whereas the 3'UTR of the GS1 gene is involved in the control of the mRNA accumulation or stability, the Gmglnβ1 5'UTR enhances the translation of both the GS1 gene and a β-glucuronidase (uidA) reporter gene in plants.

For a complete characterization of the 5'UTR of the Gmglnβ1 gene and its role as a translation enhancer, the question of whether the 5'UTR of Gmglnβ1 would have the necessary information for allowing initiation of translation in a bacterial cell was also addressed. In the traditional view of translation initiation, there are major differences between eukaryotes and prokaryotes in the way that ribosomes are recruited to the mRNA and this is mediated by sequences in the 5' non-coding region. However, there are reports that eukaryotic ribosomes can recognize prokaryotic signals and initiate synthesis at internal sites of polycistronic mRNAs. Similarly, the *Escherichia coli* ribosomes have been shown to recognize eukaryotic viral initiation signals and translate eukaryotic viral mRNAs suggesting that translation initiation signals in prokaryotes and eukaryotes are similar. To corroborate the universality of the translation initiation mechanism between prokaryotes and eukaryotes, the Gmglnβ1 gene was introduced with its 5'UTR in *E. coli* and showed accumulation of the corresponding protein in the bacterial cells, thus supporting the postulate that the mechanisms of translation initiation for this gene are conserved between plants and bacteria and may further support the notion that GS genes may have originated from a gene duplication event that preceded the divergence of prokaryotes and eukaryotes.

BRIEF SUMMARY OF THE INVENTION

Embodiments of the present invention comprise methods of enhancing translation of foreign genes in plants, plant tissue or plant cells comprising inserting a translation initiation signal from a 5' UTR of a soybean GS gene of SEQ ID NO: 3.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 32B shows the nucleotide sequences of the 5'UTR of the Gmglnβ1 and the CAMBIA leader/Gmglnβ$_1$ gene junctions (GSβ100 and GSβ103 gene constructs). The translation initiation sequence of the CAMBIA leader is underlined. Nucleotides are numbered relative to the position of the translation start site, labeled with an asterisk. The EcoRI and BglII restriction sites used to clone the Gmglnβ$_1$ gene constructs to the CaMV35S promoter are shown.

DETAILED DESCRIPTION OF THE INVENTION

Figure 1A:
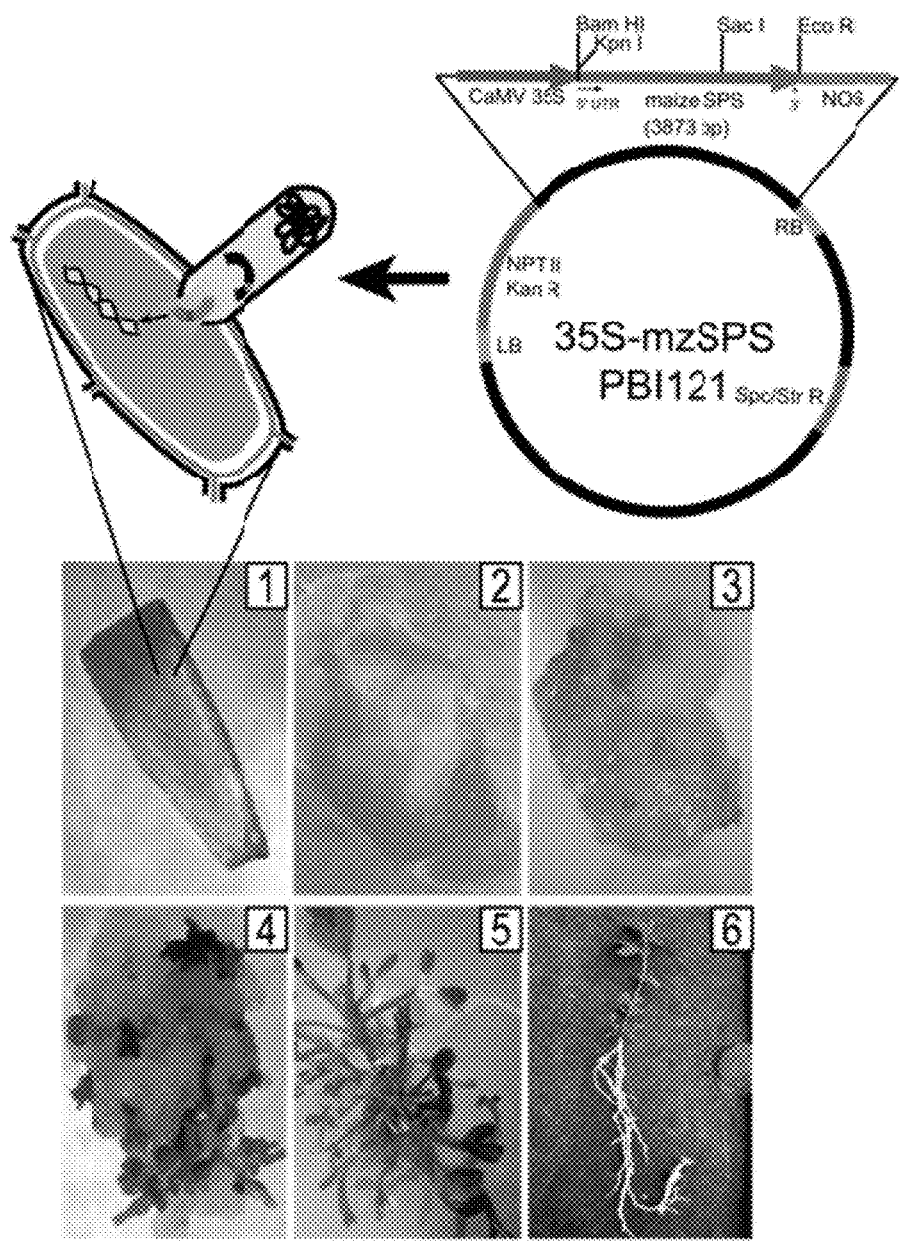
FIG. 1A shows a simple schematic of the 35S-mzSPS construct and several stages in the *A. tumefaciens* mediated plant transformation of alfalfa.

As used throughout the specification and claims, the term legume or leguminous refers to plants in the family Fabaceae (or Leguminosae), which are notable in that most of them have symbiotic nitrogen-fixing bacteria in their root nodules, including but not limited to alfalfa (lucerne; *Medicago sativa* and *M. falcata* and hybrids between them), white clover (*Trifolium repens*), red clover (*T. pratense*), alsike clover (*T. hybridum*), sweetclover (*Melilotus alba* and *M. officinalis*) and subterranean clover (*P. subterranium*), peas, beans, lentils, lupins, mesquite, carob, soybeans, peanuts, tamarind, and the woody climbing vine wisteria. The term alfalfa as used herein is intended to cover all such legumes.

Embodiments of the present invention provide methods for alteration of sucrose synthesis in a variety of plants, such as alfalfa and other forage legumes using the SPS gene. Embodiments of the present invention further provide transgenic constructs comprising the SPS gene, and allied regulatory genes, for use in the transformation of alfalfa and other legumes, and provides novel transgenic plants comprising such constructs.

As used throughout this application, the term sucrose means sugar, or a disaccharide composed of the monosaccharides glucose and fructose with the molecular formula $C_{12}H_{22}O_{11}$. The term carbon can mean the chemical element with symbol C and atomic number 6 but in some instances it can mean organic compounds comprising carbon such as sucrose. Further, as used throughout this application, the term senescence means biological aging or the change in the biology of an organism as it ages after its maturity.

In one embodiment, the SPS gene is used to transform alfalfa for the overexpression of sucrose. The genomic, cDNA and protein sequence of the SPS gene can be obtained in Genbank Accession No. NM_001112224, which provides the following sequence:

```
                                            (SEQ. ID. NO: 1)
gaattccggc gtgggcgctg ggctagtgct cccgcagcga gcgatctgag agaacggtag agttccggcc gggcgcgcgg gagaggagga gggtcgggcg gggaggatcc gatggccggg aacgagtgga tcaatgggta cctggaggcg atcctcgaca gccacacctc gtcgcgggt gccggcggcg gcggcggcgg ggggaccc aggtcgccga cgaaggcggc gagccccgc ggcgcgcaca tgaacttcaa cccctcgcac tacttcgtcg aggaggtggt caagggcgtc gacgagagcg acctccaccg gacgtggatc aaggtcgtcg ccacccgcaa cgcccgcgag cgcagcacca ggctcgagaa catgtgctgg cggatctggc acctcgcgcg caagaagaag cagctggagc tggagggcat ccagagaatc tcggcaagaa ggaaggaaca ggagcaggtg cgtcgtgagg cgacggagga cctggccgag gatctgtcag aaggcgagaa gggagacacc atcggcgagc ttgcgccggt tgagacgacc aagaagaagt tccagaggaa cttctctgac cttaccgtct ggtctgacga caataaggag aagaagcttt acattgtgct catcagcgtg catggtcttg ttcgtggaga aaacatggaa ctaggtcgtg attctgatac aggtgccag gtgaaatatg tggtcgaact tgcaagagcg atgtcaatga tgcctggagt gtacagggtg gacctcttca ctcgtcaagt gtcatctcct gacgtggact ggagctacgg tgagccaacc gagatgttat gcgccggttc caatgatgga gaggggatgg gtgagagtgg cggagcctac attgtgcgca taccgtgtgg gccgcgggat aaatacctca agaaggaagc gttgtggcct tacctccaag agtttgtcga tggagcccttc gcgcatatcc tgaacatgtc caaggctctg ggagagcagg ttggaaatgg gaggccagta ctgccttacg tgatacatgg gcactatgcc gatgctggag atgttgctgc tctcctttct ggtgcgctga atgtgccaat ggtgctcact ggccactcac ttgggaggaa caagctggaa caactgctga agcaagggcg catgtccaag gaggagatcg attcgacata caagatcatg aggcgtatcg agggtgagga gctggccctg gatgcgtcag agcttgtaat cacgagcaca aggcaggaga ttgatgagca gtggggattg tacgatggat ttgatgtcaa gcttgagaaa gtgctgaggg cacgggcgag gcgcgggtt agctgccatg gtcgttacat gcctaggatg gtggtgattc ctccgggaat ggatttcagc aatgttgtag ttcatgaaga cattgatggg gatggtgacg tcaaagatga tatcgttggt ttggagggtg cctcacccaa gtcaatgccc ccaatttggg ccgaagtgat gcggttcctg accaaccctc acaagccgat gatcctggcg ttatcaagac cagacccgaa gaagaacatc actaccctcg tcaaagcgtt tggagagtgt cgtccactca gggaacttgc aaaccttact ctgatcatgg gtaacagaga tgacatcgac gacatgtctg ctggcaatgc cagtgtcctc accacagttc tgaagctgat tgacaagtat gatctgtacg gaagcgtggc gttccctaag catcacaatc aggctgacgt cccggagatc tatcgcctcg cggccaaaat gaagggcgtc ttcatcaacc ctgctctcgt tgagccgttt ggtctcaccc tgatcgaggc tgcggcacac ggactcccga tagtcgctac caagaatggt ggtccggtcg acattacaaa tgcattaaac aacggactgc tcgttgaccc acacgaccag aacgccatcg ctgatgcact gctgaagctt gtggcagaca agaacctgtg gcaggaatgc cggagaaacg ggctgcgcaa catccacctc tactcatggc cggagcactg ccgcacttac ctcaccaggg tggccgggtg ccggttaagg aacccgaggt ggctgaagga cacaccagca gatgccggag ccgatgagga ggagttcctg gaggattcca tggacgctca ggacctgtca ctccgtctgt ccatcgacgg tgagaagagc tcgctgaaca ctaacgatcc actgtggttc gacccccagg atcaagtgca gaagatcatg aacaacatca gcagtcgtc agcgcttcct ccgtccatgt cctcagtcgc agccgagggc acaggcagca ccatgaacaa atacccactc ctgcgccggc gccggcgctt gttcgtcata gctgtggact gctaccagga cgatggccgt gctagcaaga agatgctgca ggtgatccag gaagttttca gagcagtccg atcggactcc cagatgttca agatctcagg gttcacgctg tcgactgcca tgccgttgtc cgagacactc cagcttctgc agctcggcaa gatcccagcg accgacttcg acgccctcat ctgtggcagc ggcagcgagg tgtactatcc tggcacggcg aactgcatgg acgctgaagg aaagctgcgc ccagatcagg actatctgat gcacatcagc
```

```
caccgctggt cccatgacgg cgcgaggcag accatagcga agctcatggg cgctcaggac ggttcaggcg acgctgtcga gcaggacgtg gcgtccagta atgcacactg tgtcgcgttc ctcatcaaag accccaaaa ggtgaaaacg gtcgatgaga tgagggagcg gctgaggatg cgtggtctcc gctgccacat catgtactgc aggaactcga caaggcttca ggttgtccct ctgctagcat caaggtcaca ggcactcagg tatctttccg tgcgctgggg cgtatctgtg gggaacatgt atctgatcac cggggaacat ggcgacaccg atctagagga gatgctatcc gggctacaca agaccgtgat cgtccgtggc gtcaccgaga agggttcgga agcactggtg aggagcccag gaagctacaa gagggacgat gtcgtcccgt ctgagacccc cttggctgcg tacacgactg gtgagctgaa ggccgacgag atcatgcggg ctctgaagca agtctccaag acttccagcg gcatgtgaat ttgatgcttc ttttacattt tgtccttttc ttcactgcta tataaaataa gttgtgaaca gtaccgcggg tgtgtatata tatattgcag tgacaaataa aacaggacac tgctaactat actggtgaat atacgactgt caagattgta tgctaagtac tccatttctc aatgtatcaa tcggaattc
```

The amino acid sequence encoded by the nucleic acid is:

```
                                            (SEQ ID. NO. 4)
MAGNEWINGYLEAILDSHTSSRGAGGGGGGGDPRSPTKAASPRGAHMNFN

PSHYFVEEVVKGVDESDLHRTWIKVVATRNARERSTRLENMCWRIWHLAR

KKKQLELEGIQRISARRKEQEQVRREATEDLAEDLSEGEKGDTIGELAPV

ETTKKKFQRNFSDLTVWSDDNKEKKLYIVLISVHGLVRGENMELGRDSDT

GGQVKYVVELARAMSMMPGVYRVDLFTRQVSSPDVDWSYGEPTEMLCAGS

NDGEGMGESGGAYIVRIPCGPRDKYLKKEALWPYLQEFVDGALAHILNMS

KALGEQVGNGRPVLPYVIHGHYADAGDVAALLSGALNVPMVLTGHSLGRN

KLEQLLKQGRMSKEEIDSTYKIMRRIEGEELALDASELVITSTRQEIDEQ

WGLYDGFDVKLEKVLRARARRGVSCHGRYMPRMVVIPPGMDFSNVVVHED

IDGDGDVKDDIVGLEGASPKSMPPIWAEVMRFLTNPHKPMILALSRPDPK

KNITTLVKAFGECRPLRELANLTLIMGNRDDIDDMSAGNASVLTTVLKLI

DKYDLYGSVAFPKHHNQADVPEIYRLAAKMKGVFINPALVEPFGLTLIEA

AAHGLPIVATKNGGPVDITNALNNGLLVDPHDQNAIADALLKLVADKNLW

QECRRNGLRNIHLYSWPEHCRTYLTRVAGCRLRNPRWLKDTPADAGADEE

EFLEDSMDAQDLSLRLSIDGEKSSLNTNDPLWFDPQDQVQKIMNNIKQSS

ALPPSMSSVAAEGTGSTMNKYPLLRRRRRLFVIAVDCYQDDGRASKKMLQ

VIQEVFRAVRSDSQMFKISGFTLSTAMPLSETLQLLQLGKIPATDFDALI

CGSGSEVYYPGTANCMDAEGKLRPDQDYLMHISHRWSHDGARQTIAKLMG

AQDGSGDAVEQDVASSNAHCVAFLIKDPQKVKTVDEMRERLRMRGLRCHI

MYCRNSTRLQVVPLLASRSQALRYLSVRWGVSVGNMYLITGEHGDTDLEE

MLSGLHKTVIVRGVTEKGSEALVRSPGSYKRDDVVPSETPLAAYTTGELK

ADEIMRALKQVSKTSSGM
```

One method of the present invention uses the SPS gene sequence in genetic constructs and vectors for transforming plant cells and plant tissues in order to generate transgenic alfalfa plants exhibiting overexpression of sucrose phosphate synthase, which catalyzes sucrose synthesis. Such plants exhibit an increase in leaf to stem ratio, show increased levels of soluble carbohydrates and protein, low fiber, resistance to some biotic and abiotic stresses, delayed senescence, and a significant increase in elemental N, suggesting increased nitrogen use efficiency (NUE).

It is noted that the nucleic acid molecules described in this application represent some of the multiple possible embodiments of the invention. However, the invention also comprises degenerate nucleic acids that differ from the aforementioned sequences. Due to degeneracy in the genetic code, variations in the DNA sequence result in translation of identical peptides. It is thus understood that numerous choices of nucleotides may be made that lead to a sequence capable of directing production of the peptides or functional analogs thereof. Therefore, embodiments of the present invention comprise degenerative nucleotide substitutions.

In accordance with another embodiment of the invention, alterations of the SPS gene can be used, for instance, for expression and functional studies of the encoded protein in alfalfa or other legumes. The DNA sequences can be altered using procedures such as restriction enzyme digestion, DNA polymerase fill-in, exonuclease deletion, terminal deoxynucleotide transferase extension, ligation of synthetic or cloned DNA sequences and site-directed in vitro mutagenesis, including site-directed sequence alteration using specific oligonucleotides together with PCR. The SPS gene sequence can also be altered using site-specific recombination, for instance.

In order to express sucrose phosphate synthase, eukaryotic and prokaryotic expression systems may be generated in which the SPS gene sequence is introduced into a plasmid or other vector, which is then used to transfect living plant cells. Constructs in which the SPS cDNA sequence comprising the entire open reading frame is inserted in a correct orientation into an expression plasmid, can be used for protein expression. Alternatively, portions of the sequence can be inserted. Prokaryotic and eukaryotic expression systems allow various important functional domains of the SPS protein to be recovered as fusion proteins and used for binding, structural and functional studies and also for the generation of appropriate antibodies.

Typical expression vectors comprise promoters that direct the synthesis of large amounts of mRNA corresponding to the gene. As used herein, a suitable promoter may be, for example, but not limited to, a 35S promoter, a nopaline synthase (NOS) promoter, a small subunit rubisco promoter, light-induced promoters, leaf specific promoters, vegetative promoters or any other promoters that are expressed in the desired plant tissue in accordance with the selected application. Plant cells and tissues include, but are not limited to, leaf, stem, flower, root, developing seed, mature seed and seedling. Typical expression vectors can also include sequences allowing autonomous replication within the host organism, sequences that encode genetic traits that allow cells containing the vectors to be selected, and sequences that increase the efficiency with which the mRNA is translated. Stable long-term vectors can be maintained as freely replicating entities by using regulatory elements of viruses. Cell lines can also be produced which have integrated the vector into the genomic DNA and in this manner the gene product is produced on a continuous basis.

Another embodiment of the invention comprises a transgenic plant or plant cell transformed with a nucleic acid comprising a nucleotide sequence encoding the amino acid sequence of SPS and wherein the nucleotide sequence is expressed. In one embodiment, the plant or plant cell is alfalfa, which is transformed with and expresses a nucleic acid comprising the nucleotide sequence of SPS. The plant or plant cell can be a monocot or a dicot. Preferably, the plant or plant cell is a legume, for example, alfalfa. The invention further provides a method for overexpressing sucrose in a legume plant that comprises, but is not limited to: Transforming a legume plant with a nucleic acid sequence from, including but not limited to:
  a) a nucleic acid encoding a coding region of the SPS regulatory gene;
  b) a nucleic acid coding for a SPS regulatory gene sequence;
  c) a nucleic acid sequence sharing at least 85% sequence identity with a) or b);
  d) a nucleic acid degeneracy equivalent to any one of a) to c); or
  f) a nucleic acid fragment exhibiting SPS gene biological activity of any one of a) to d); and growing the plant.

According to a further embodiment of the invention, the SPS gene can be used in a plant, plant cell or tissue, to increase sucrose content for improving forage quality and as a result, improving animal health, carcass weight gain, milk and wool production and decreasing bloat in animals. Such plants include, but are not limited to, alfalfa (lucerne; *Medicago sativa* and *M. falcata* and hybrids between them), white clover (*Trifolium repens*), red clover (*T. pratense*), alsike clover (*T. hybridum*), sweetclover (*Melilotus alba* and *M. officinalis*) and subterranean clover (*P. subterranium*).

In accordance with a further aspect of the present invention, a genetic construct, comprising the SPS nucleotide sequence, can be used under the control of a suitable promoter that is capable of expression in a designated plant part, e.g. the leaf. The genetic construct preferably transforms alfalfa and other forage legumes, increases tolerance or resistance to infection by fungi, viruses and/or bacteria; and, increases tolerance or resistance to disease, insects, nematodes, and other pest species.

There is a high degree of constraints in overexpressing GS1. Alfalfa transformants with a soybean GS1 gene (Gmglnβ1) driven by the CaMV 35S promoter previously showed no increase in GS1 polypeptide or GS activity. For example, there was transgene transcript accumulation in the leaves but not in the nodules. Furthermore, the alfalfa transformants showed a significant drop in the level of the transcript corresponding to the transgene when grown under nitrogen sufficient conditions. Since the CaMV 35S promoter is active in the nodules and its activity is not influenced by nitrate, it can be concluded that the expression of GS1 is regulated at the level of transcript stability. The absence of an increase in GS1 polypeptide or activity in the leaves where there is transgene transcript accumulation, indicates that there is regulation also at a translational or post-translational level. Embodiments of the present invention comprise a method of removing 3' UTR from the GS1 transgene (Gmglnβ1). The removal of 3' UTR from the GS1 transgene abolishes the regulatory constraints in the expression of the transgene in alfalfa and the transformants show not only increased GS1 transcript, but also an increase in the GS1 polypeptide and a novel GS isoenzyme. Moreover, results from the method show that the 3'UTR mediated posttranscriptional regulation requires a product of N assimilation.

GS1 encoded by Gmglnβ1 is regulated at the level of transcript turnover and/or translation initiation and this regulatory step is mediated via the 3'UTR. Furthermore, a trans-factor or micro RNA (miRNA) is involved in transcript turnover/translation repression. The trans-factor is either synthesized de novo or an existing protein is posttranslationally modified in response to the C/N ratio in the cells. If miRNA is involved, it can be synthesized under certain metabolic conditions associated with NH3 assimilation and it can target the GS1 mRNA for turnover and/or translation repression.

In one embodiment, the GS1 gene is used to transform alfalfa plants. The genomic, cDNA and protein sequence of the GS1 gene can be obtained in Genbank Accession No. AF301590.1, which provides the following sequence:

```
                                          (SEQ. ID. NO: 2)
tctaaaagag atcttttct gctctttgaa gaaagaaggg tctttgcttg attttggaga tgtctctgct ctcagatctc atcaaccttc acctctccga taccaccgag aaggtgatcg cagagtacat atggatcggt ggatcaggaa tggacctgag gagcaaagca aggactctcc caggaccagt tagcgaccct tcagagcttc ccaagtggaa ctatgatggt tccagcacag gtcaagctcc tggtgaagac agtgaagtga ttttataccc acaagccatt ttcagggatc cattcagaag gggtaacaat atcttggtta tctgtgatgc ctacactcct gctggagaac ctattcccac taacaagagg cacgctgctg ccaaggtttt cagccatcct gatgttgttg ctgaagtgcc atggtacggt attgaacaag aatacacctt gttgcagaaa gatatccaat ggcctcttgg gtggcctgtt ggtggtttcc ctggacctca gggtccatac tactgtggtg ttggcgctga caaggctttt ggccgtgaca ttgttgacgc acactacaaa gcctgtattt atgctggcat caacatcagt ggaattaatg gagaagtgat gcccggtcag tgggaattcc aagttggacc ttcagttgga atctcagctg gtgatgagat ttgggcagct cgttacatct tggagaggat cactgagatt gctggtgtgg tggtttcctt tgaccccaag ccaattaagg gtgattggaa tggtgctggt gctcacacaa actacagcac caagtccatg agagaagatg gtggctatga agtgatcaaa gcagcaattg acaagttggg gaagaagcac aaggagcaca ttgctgctta tggagaaggc aacgaacgtc gtttgacagg acgccacgaa accgctgaca tcaacacctt cttatgggga gttgcaaacc gtggagcttc tgttagggtt gggagagaca cagagaaagc agggaaggga tattttgagg acagaaggcc agcttccaac atggacccat
```

-continued

```
acgtggttac ttccatgatt gcagacacaa ccattctgtg gaagccatga gcaaaacctg catgttttct ccctttggat ggaaaggaac agttatgctt ttcttagtag gatttggtct ctctctcttt ttacctttg attggtacta tggttggtgc cttgttggtt ggtgcaacta actggcaagg gttgttcatt gttttcttct attccttcc ctcgttttcc gattgttaca atgacaataa tttaatggtt attatcagtc ttgaacaaag aaatgctgat tgtgaagtat aataataata tatgaaattg ccg
```

The amino acid sequence encoded by the nucleic acid is:

(SEQ ID. NO. 5)
```
MSLLSDLINLNLSDTTEKVIAEYIWIGGSGMDLRSKARTLPGPVSDPSEL

PKWNYDGSSTGQAPGEDSEVILYPQAIFRDPFRRGNNILVICDAYTPAGE

PIPINKRHAAAKVFSHPDVVAEVPWYGIEQEYTLLQKDIQWPLGWPVGGF

PGPQGPYYCGVGADKAFGRDIVDAHYKACIYAGINISGINGEVMPGQWEF

QVGPSVGISAGDEIWAARYILERITEIAGVVVSFDPKPIKGDWNGAGAHT

NYSTKSMREDGGYEVIKAAIDKLGKKHKEHIAAYGEGNERRLTGRHETAD

INTFLWGVANRGASVRVGRDTEKAGKGYFEDRRPASNMDPYVVTSMIADT

TILWKP
```

While most of the genetic manipulations have utilized one gene at a time and used a run-of-the-mill constitutive CaMV 35S promoter, an embodiment of the present invention fine-tunes the expression such that the transgenes are expressed in an organ/tissue-specific manner. In a different embodiment of the invention, introduction of both the transgenes into the same plant is performed behind different regulatory elements, such that the SPS gene, is expressed in the leaves and the $GS_1$ in the stems, roots and nodules. The dual gene transformants preferably enhance the traits that are with the individual gene transformants.

In one embodiment of the invention, the 5' UTR of the $Gmgln\beta_1$ gene is used as a translation enhancer for foreign genes in plants. Specifically, the cDNA sequence of the 5' UTR of the Gmglnβ1 gene being as follows:

(SEQ ID NO: 3)
```
tctaaaagag atcttttct gctctttgaa gaaagaaggg tctttgcttg attttggag
```

INDUSTRIAL APPLICABILITY

The invention is further illustrated by the following non-limiting examples.

Example 1

A maize SPS gene (mzSPS) cDNA was engineered between the constitutive CaMV35S promoter and the NOS terminator in the vector pMON316. The construct referred to as the 35S-mzSPS was introduced into alfalfa using a routine *A. tumefaciens* mediated transformation protocol and putative 35S-mzSPS alfalfa transformants were selected based on their ability to grow and root on selection media containing kanamycin. These putative alfalfa transformants, along with non-transformed (NT) alfalfa plants were transferred to pots and grown in the greenhouse. DNA was isolated from the leaves of these transformants and subjected to PCR amplification using NPTII gene specific primer sets. The PCR products were then analyzed by agarose gel electrophoresis.

Figure 1B:
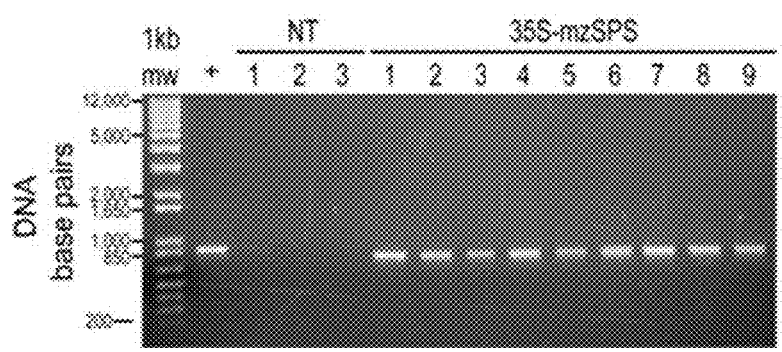
FIG. 1B shows the genomic DNA extracted from the leaves of non-transformed and putative 35S-mzSPS transformed alfalfa plants.

FIGS. 1A-1B show production and identification of putative alfalfa transformed plants constitutively overexpressing the maize SPS gene. Referring to FIG. 1A, a schematic of the 35S-mzSPS construct and several stages in the *A. tumefaciens* mediated plant transformation of alfalfa are shown beginning with infected leaf tissue (1), followed by cell proliferation/expansion (2), and the formation of calli (3), embryos (4) and plantlets (5). Fully developed plants (6) were placed and grown in pots under greenhouse conditions and then used for further analysis. Referring to FIG. 1B, genomic DNA extracted from the leaves of non-transformed and putative 35S-mzSPS transformed alfalfa plants was subjected to PCR using NPT II, kanamycin resistance gene, specific primers. An Invitrogen® 1 kb plus DNA ladder (lane 1), empty vector (+ control; lane 2) and samples from both the non-transformed (NT) and putative transformants (35S-mzSPS) were tested. The specific 800 bp amplified fragment obtained with the positive control template and the transformants is indicated in the gel shown. While nine randomly selected transformants used in this experiment along with the positive control (plasmid DNA) showed the presence of a 800 bp fragment, the NT plants and the negative control (*A. tumefaciens* with the empty vector) did not show the band. These results confirmed the integration of the tDNA with the 35S-mzSPS gene construct along with the NPTII gene in the transformants.

Figure 2:
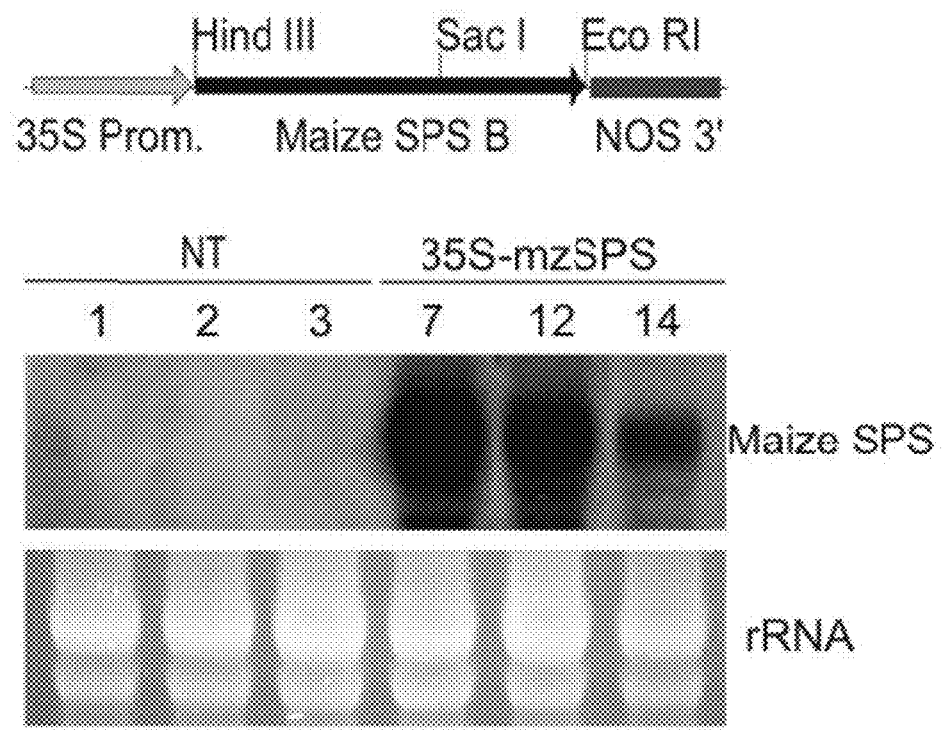
FIG. 2 shows an analysis of maize SPS transcript accumulation in the leaves of 35S-mzSPS transformed plants. Total RNA (about 18 µg) extracted from the leaves of non-transformed (NT; lanes 1-3) and 35S-mzSPS transformed alfalfa (lanes marked 7, 12 and 14) plants was subjected to northern blot hybridization, as described below, using $^{32}P$ radioactive-labeled cDNA of maize SPS. The gel was stained with SYBR gold and the rRNA bands are shown to represent the loads. A representative blot is shown.

To check for the functionality of the transgene construct, total RNA extracted from the leaves of three randomly picked 35S-mzSPS transformants and three NT plants were subjected to northern blot analysis using the mzSPS coding region as a probe. As seen in FIG. 2, under hybridization conditions, the probe did not hybridize to the RNA from the NT plants but showed a distinct hybridizing band in the transformants representing the mzSPS transcript. The mzSPS transcript level showed plant to plant variation, with the highest level being in transformant #7. The results indicate that the gene construct is functional with regards to transcription and the differences in the expression level is probably an attribute of position effect.

Figure 3A:
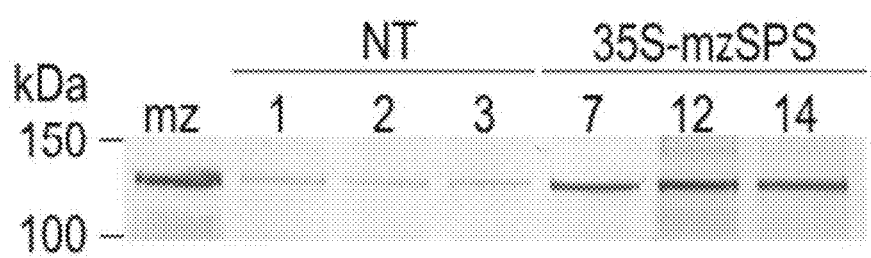
FIG. 3A shows fifty micrograms of total soluble protein extracted from the leaves of non-transformed (NT) and 35S-mzSPS transformed (7, 12, 14) alfalfa plants, along with maize (mz) leaf extract (about 10 µg), was fractionated by SDS-PAGE (10%) and was subjected to western blot analysis using anti-maize SPS antibodies.
Figure 3B:
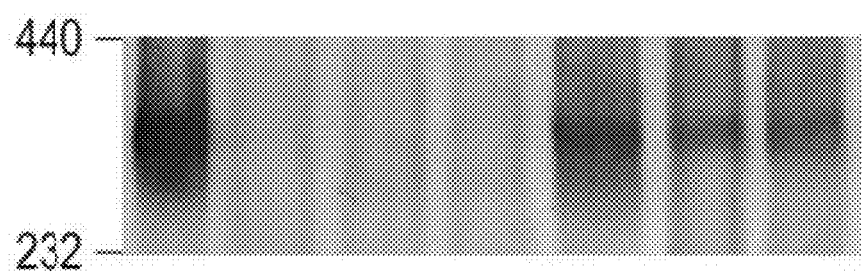
FIG. 3B shows the same leaf extracts (about 100 µg) used in panel 3A, were fractionated by native-PAGE (7.5%) followed by western blot analysis using the same anti-maize SPS antibodies.
Figure 3C:
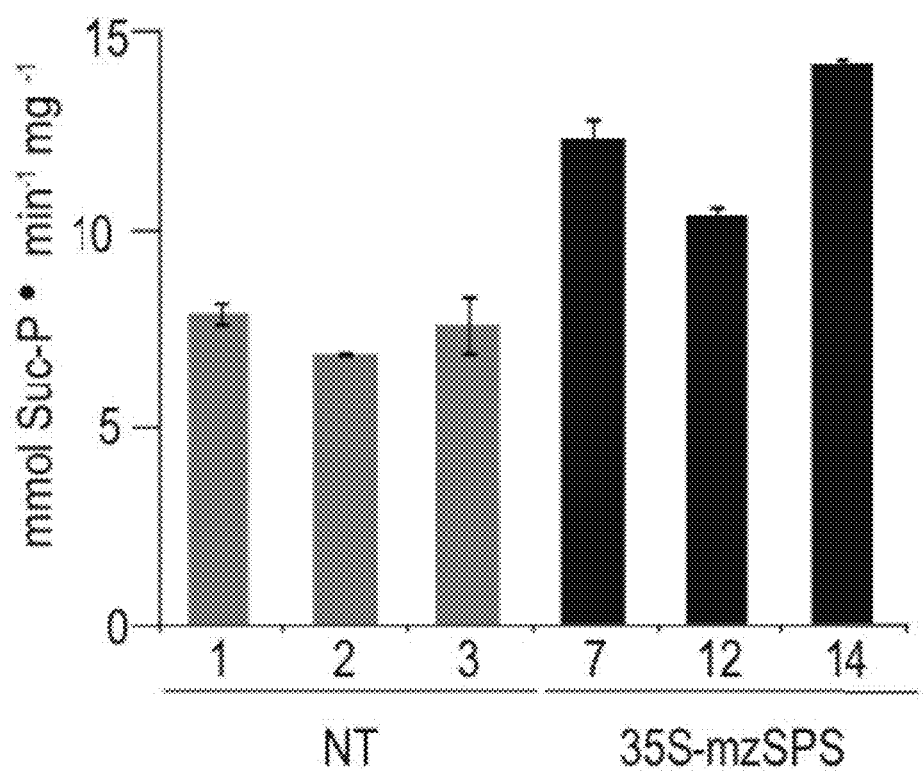
FIG. 3C shows the protein extracts used for PAGE in 3A assayed for SPS activity.

To check if mzSPS transcript accumulation in the leaves of the transformants translates into a functional protein, the same tissues that were used for RNA extraction, were used for SPS protein and SPS enzyme activity analysis. Total soluble protein extracted from the leaves was subjected to SDS- and native-PAGE western blot analysis using maize SPS antibodies. FIGS. 3A-3C show an analysis of Maize SPS polypeptide and holoenzyme accumulation and total SPS activity in the leaves of non-transformed and 35S-mzSPS transformed alfalfa plants. As seen in FIG. 3A, both the NT plants and the 35S-mzSPS transformants showed an immunoreactive band of about 140 kD that co-migrated with an immunoreactive band in the lane with the maize leaf extract on SDS PAGE, the level being about half of that seen in the maize leaf extract.

Considering that the amount of leaf extract loaded for maize leaf was 5-fold less than for the leaf extracts of alfalfa, it would seem that the alfalfa transformants showed about 10-fold less SPS than the maize leaf. The band in the NT plant extract was many fold less intense than the band in the extracts from the transformants. The immunoreactive band in the samples from NT plants probably represents the endogenous SPS protein which has some affinity for the maize SPS antibodies.

Since SPS is a dimeric protein in its native form, the transgene protein was checked to see if it was assembling into a dimer by performing native gel western analysis with the leaf extracts. As seen in FIG. 3B, the immunoreactive band corresponding to the maize SPS polypeptide migrated at about 140 kDa (3A) and the maize SPS holoenzyme migrated at about 280 kDa (3B), as shown in the lane marked mz, which serves as the positive control. The migration of the molecular weight standards is shown.

SPS activity was assayed in the same leaf protein extracts used for western analysis (panel 3A and 3B). Average values±SE of three experiments were plotted as nmol Sucrose-P min-1 mg-1 native gel western analysis showed a broad immunoreactive band only in the maize leaf extract and in the extracts from the three transformants. The band intensity of native SPS protein showed a correlation with the mzSPS transcript level. The absence of an immunoreactive native protein in the NT plants likely reflects the low affinity of the alfalfa SPS native protein for the mzSPS antibody or just a reflection of the relatively low levels of the holoprotein in the control plants compared to the transformants.

SPS enzyme is known to undergo post-translational modification that can affect its activity and as such, it is critical that the SPS transgene product is active in its non-native environment. The same protein extracts used for PAGE were assayed for SPS activity. SPS enzyme activity was measured by the quantification of fructosyl moiety of sucrose using the anthrone test in triplicate for each plant and as seen in FIG. 3C, the transformants showed higher SPS activity compared to the non-transformed plants. An approximately 50-120% increase in total SPS activity was seen in the leaves of the three 35S-mzSPS transformed plants, where transgenic line 35S-mzSPS #14 showed the highest levels, followed by #7 and #12. Taken together, these results indicate that the expression of the 35S-mzSPS gene in alfalfa is accompanied by an increase in SPS activity in the leaves. Transformant #7 was selected for further analysis.

The pathways of sucrose and starch formation are interdependent as they compete for the pool of triose phosphates produced by the Calvin cycle. A consequence of this complex interdependence is that sucrose formation and starch formation are reciprocally related. Thus, increasing SPS activity could have an impact on the sucrose and starch levels when the leaves are in the photosynthetic mode. To check this postulate, total soluble carbohydrate (TSC), sucrose, and starch content was determined in the leaves of NT alfalfa and 35S-mzSPS transformed plants during the light and dark period. A set of 10 clonally propagated NT alfalfa and 35S-mzSPS (#7) transformed plants were placed under greenhouse conditions and inoculated with $S.$ $meliloti$. Leaf tissue from five NT and five transformed alfalfa plants were harvested at midday representing the light period and another set of plants were harvested at midnight representing the dark period on that same day for carbohydrate analysis.

Figure 4:
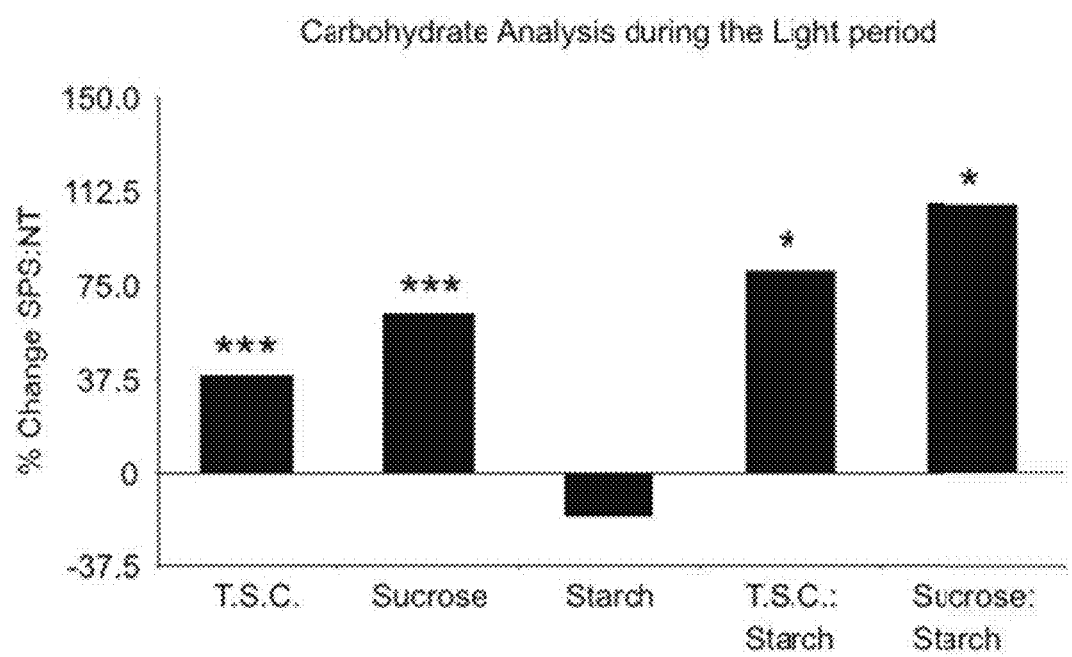
FIG. 4 shows a leaf carbohydrate analysis of non-transgenic control and 35S-mzSPS transformed alfalfa plants during the light period, and percent change in the leaf total soluble carbohydrate (TSC), sucrose, and starch content (35-mzSPS/NT) during the light period. Percent change was calculated from data in Table A.1 below. P values were calculated using Students t-test analysis (*, P≤0.05; , P≤0.01; *, P≤0.001).

Referring to FIG. 4, during the light period, the transformed plants exhibited an approximately 39 and 64 percent increase in leaf TSC and sucrose content (P<0.001), respectively, when compared to the non-transformed plants.

TABLE A.1

Total soluble carbohydrate (TSC), sucrose, and starch content in the leaves of alfalfa non-transformed and 35S-mzSPS transformed plants during the light period.

|  | T.S.C ($\mu$mol g FW-1) | Sucrose ($\mu$mol g FW$^{-1}$) | Starch ($\mu$mol g FW$^{-1}$) | T.S.C.:Starch ratio | Sucrose:Starch ratio |
|---|---|---|---|---|---|
| NT |  |  |  |  |  |
| 2a | 25.1 | 8.0 | 477.3 | 0.053 | 0.017 |
| 2b | 24.5 | 7.0 | 500.0 | 0.049 | 0.014 |
| 2c | 25.1 | 8.0 | ND | ND | ND |
| 2d | 27.2 | 9.0 | 701.2 | 0.039 | 0.013 |
| 2e | 24.2 | 7.0 | ND | ND | ND |
| Average | 25.2 | 7.8 | 559.5 | 0.047 | 0.015 |
| S.E. | ±0.2 | ±0.2 | ±24.6 | ±0.001 | ±0.000 |
| 35S-mzSPS |  |  |  |  |  |
| 7a | 32.0 | 10.0 | ND | ND | ND |
| 7b | 40.4 | 14.0 | 521.8 | 0.077 | 0.027 |
| 7c | 31.4 | 14.0 | ND | ND | ND |
| 7d | 34.0 | 12.0 | 315.8 | 0.108 | 0.038 |
| 7e | 37.4 | 14.0 | 542.8 | 0.069 | 0.026 |
| Average | 35.0 | 12.8 | 460.1 | 0.085 | 0.030 |
| S.E. | ±0.8 | ±0.4 | ±25.1 | ±0.004 | ±0.001 |
| % change | 38.9 | 64.1 | -17.8 | 80.9 | 107.9 |
| t-test | 0.0006 | 0.0005 | 0.3831 | 0.0386 | 0.0184 |

In Table A.1 above, leaf tissue from five non-transformed and five 35S-mzSPS transformed alfalfa plants were analyzed for total soluble carbohydrate, sucrose and starch levels. Values for each plant are shown along with TSC to starch ratios and sucrose to starch ratios. ND represents data that was not determined. Percent change was calculated from averages and P values were calculated using a two-sided Student t-test.

In FIG. 4, the transformed plants were approximately 18 percent lower in leaf starch content than the non-transformed plants (P=0.3831) during the same period. Consequently, the calculated TSC:starch and sucrose:starch ratios were approximately 80 and 110 percent higher, respectively, in the transformed plants when compared to the NT plants (P<0.05).

Figure 5:
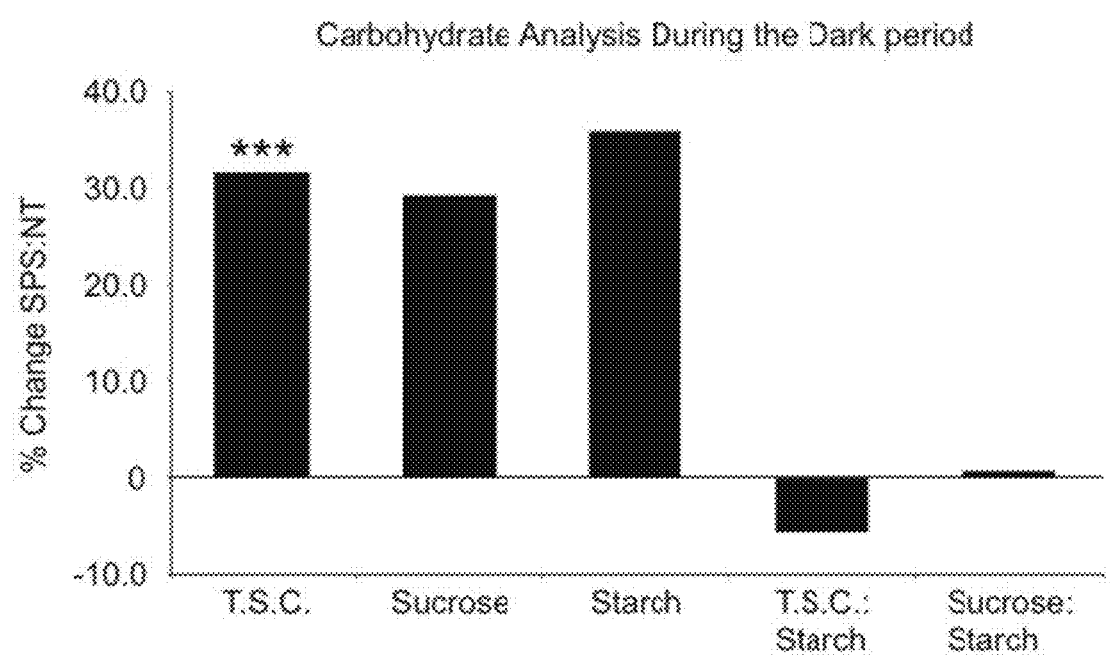
FIG. 5 shows a leaf carbohydrate analysis of non-transgenic control and 35S-mzSPS transformed alfalfa plants during the dark period, and percent change in the leaf total soluble carbohydrate (TSC), sucrose and starch content (35-mzSPS/NT) during the dark period. Percent change was calculated from data in Table A.1 below. P values were calculated using Students t-test analysis (*, P≤0.05; , P≤0.01; *, P≤0.01).

Referring now to FIG. 5, the leaf TSC in the transformed plants showed an about 32% increase over NT plants during the dark period (P<0.001; see table A.2 below).

TABLE A.2

Total soluble carbohydrate (TSC), sucrose, and starch content in the leaves of alfalfa non-transformed and 35S-mzSPS transformed plants during the dark period.

|  | T.S.C. (μmol g FW−1) | Sucrose (μmol g FW$^{-1}$) | Starch (μmol g FW$^{-1}$) | T.S.C.:Starch ratio | Sucrose:Starch ratio |
|---|---|---|---|---|---|
| NT |  |  |  |  |  |
| 2a | 20.5 | 4.0 | ND | ND | ND |
| 2b | 20.5 | 4.0 | 499.4 | 0.041 | 0.008 |
| 2c | 22.7 | 5.0 | 371.2 | 0.061 | 0.013 |
| 2d | 21.3 | 5.0 | 702.9 | 0.030 | 0.007 |
| 2e | 23.0 | 6.0 | ND | ND | ND |
| Average | 21.6 | 4.8 | 524.5 | 0.044 | 0.010 |
| S.E. | ±0.2 | ±0.2 | ±33.5 | ±0.003 | ±0.001 |
| 35S-mzSPS |  |  |  |  |  |
| 7a | 27.6 | 6.0 | ND | ND | ND |
| 7b | 26.9 | 5.0 | ND | ND | ND |
| 7c | 29.6 | 6.0 | 727.5 | 0.041 | 0.008 |
| 7d | 30.6 | 8.0 | 615.6 | 0.050 | 0.013 |
| 7e | 27.5 | 6.0 | 795.6 | 0.035 | 0.008 |
| Average | 28.4 | 6.2 | 712.9 | 0.042 | 0.010 |
| S.E. | ±0.3 | ±0.2 | ±18.2 | ±0.002 | ±0.001 |
| % change | 31.6 | 29.2 | 35.9 | −5.7 | 0.7 |
| t-test | 0.0001 | 0.0528 | 0.1617 | 0.8152 | 0.9818 |

Percent change in carbohydrates from the light period to dark period:

|  | T.S.C. | Sucrose | Starch | TSC:Starch | Sucrose:Starch |
|---|---|---|---|---|---|
| NT | −14.3 | −38.5 | −6.2 | −5.6 | −34.4 |
| 35S-mzSPS | −18.8 | −51.6 | 54.9 | −50.8 | −68.2 |
| NT-t-test | 0.001 | 0.000 | 0.785 | 0.806 | 0.096 |
| SPS-t-test | 0.007 | 0.000 | 0.047 | 0.027 | 0.008 |

Table A.2 shows the total soluble carbohydrate (TSC), sucrose, and starch content in the leaves of non-transformed and 35S-mzSPS transformed alfalfa plants during the dark period. Leaf tissue from five non-transformed and five 35S-mzSPS transformed alfalfa plants were analyzed for total soluble carbohydrate, sucrose and starch levels. Values for each plant are shown along with TSC to starch ratios and sucrose to starch ratios. ND represents data that was not determined. Percent change was calculated from averages between the two sets (NT and SPS) during the dark period and P values were obtained by using a two-sided Student t test. Same calculations were done comparing data from the light period to the dark period within each class of plants.

As shown in FIG. 5, while the leaf sucrose and starch content was also substantially higher, approximately 30 and 35 percent (respectively), in the transformed plants during the same period, these differences were not significant (P=0.053 and P=0.16, respectively). As such, no significant changes were seen in the calculated TSC:starch and sucrose: starch ratios when comparing the two classes of plants (P=0.81 and p=0.98, respectively; FIG. 5 and Table A.2) indicating C partitioning was not as enhanced to sucrose biosynthesis in the transformants. Hence, the increased SPS activity seen in the leaves of the transformed alfalfa plants enhanced carbon partitioning to sucrose synthesis only during the light period at which time the leaves are photosynthetically active.

Furthermore, the absence of photosynthetic activity in the leaves during the dark period resulted in a significant reduction in leaf TSC and sucrose content in both classes of plants compared to the levels seen in the light period (Table A.2). However, the starch content in the leaves of the transformed plants during the dark period was significantly higher than the levels during the light period (P<0.05; Table A.2). As such, the calculated leaf TSC:starch and sucrose: starch ratios showed a significant drop in the transformed plants (P<0.05 and P<0.01, respectively; Table A.2). On the contrary, the NT plants showed no significant changes in sucrose:starch ratios between the two time periods. The NT plants analyzed during the dark period showed approximately a 6 percent drop in starch content when compared to the plants analyzed during the light period.

SPS in some plants is known to be light regulated and the regulation may be by protein phosphorylation, allosterically by Glc-6-P and Pi, and in the case of developing leaves also by changes in the protein level. To check if changes in the sucrose level in light and dark period could be attributed to changes in SPS levels, total soluble protein (TSP), extracted from the leaves of the same plants analyzed during the two time periods, was subjected to SDS-PAGE western blot analysis using the maize SPS antibody. About 10 μg of maize leaf protein used in FIG. 6, was used as a positive internal control in both gels.

Figure 6A:
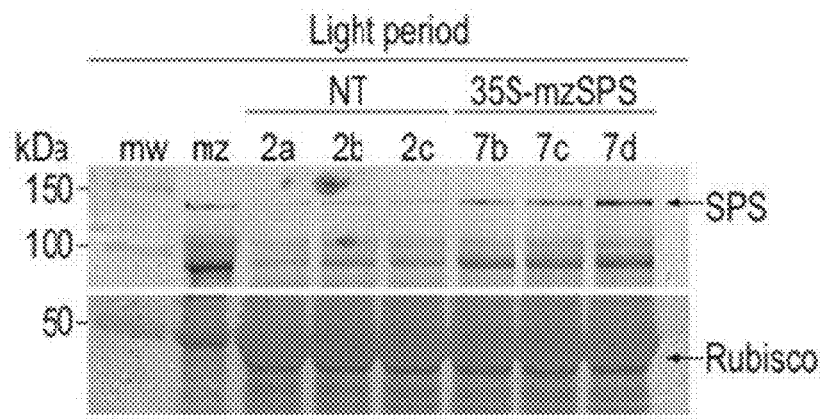
FIG. 6A shows an analysis of Maize SPS polypeptide in the leaves of non-transgenic and 35S-mzSPS transgenic alfalfa plants during the light period (day).
Figure 6B:
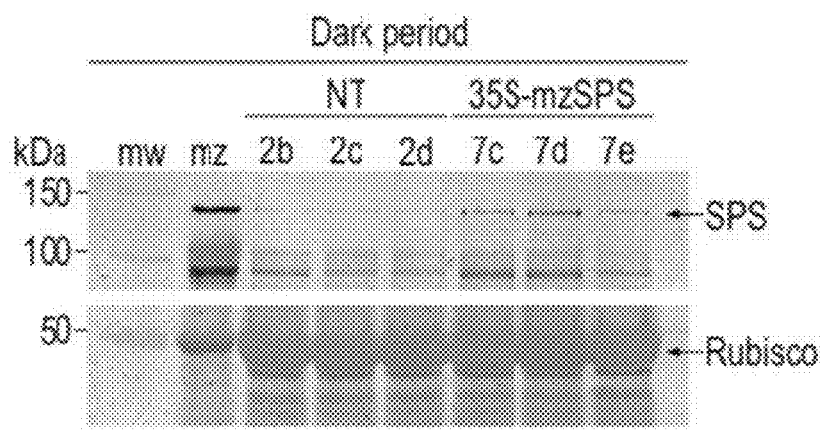
FIG. 6B shows an analysis of Maize SPS polypeptide in the leaves of non-transgenic and 35S-mzSPS transgenic alfalfa plants during the dark period (night).

Referring to FIG. 6, fifty micrograms of total soluble protein extracted from the leaves of non-transformed (NT) and 35-mzSPS alfalfa transformed plants during the light 6A and dark period 6B, along with maize (mz) leaf extract (about 10 μg), was fractionated by SDS-PAGE (10%) and was subjected to western blot analysis using anti-maize SPS antibodies. The maize leaf extract was used as control to account for differences in blotting conditions between the two gels. The blots from a representative experiment are presented. Arrows indicate the immunoreactive band corresponding to maize SPS polypeptide and the stained Rubisco polypeptide that migrate at approximately 140 kDa and 40 kDa, respectively. The migration of the molecular weight standards is as shown. The maize protein showed two major immunoreactive bands: about 140 kD band and a about 90 kD band, the latter probably representing a breakdown product of the 140 kD SPS protein. Both, the transformants and the NT plants showed higher accumulation of the SPS protein (140 kD and 90 kD immunoreactive bands) in the tissues harvested in the light period compared to the tissues harvested in the dark period. The change in maize SPS polypeptide accumulation in the leaves of the transformants followed a similar trend as seen in the sucrose content during the two periods with the higher accumulation of SPS protein seen during the light period. The data, shows the diurnal/circadian regulation pattern of the maize SPS at the protein level in alfalfa.

Clearly, the heterologous expression of the maize SPS transgene in alfalfa results in enhanced carbon partitioning to sucrose synthesis in the leaves and an increase in the sucrose:starch ratios during the light period and this is attributed to the diurnal changes in SPS level.

Figure 7A:
FIG. 7A shows established non-transformed and 35S-mzSPS (#7) transformed plants were cut back to the base/crown and allowed to grow until the flowering stage.
Figure 7B:
FIG. 7B shows inflorescence of transformed plants.
Figure 7C:
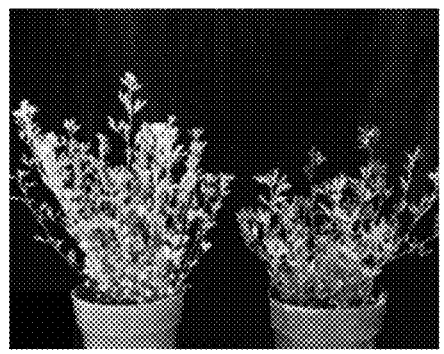
FIG. 7C shows side by side comparison of a representative transformed and control plants grown for the same period of time.
Figure 7D:
FIG. 7D shows inflorescence of control plants at the same developmental stage as the inflorescence from the transformed plants in FIG. 7B.
Figure 7E:
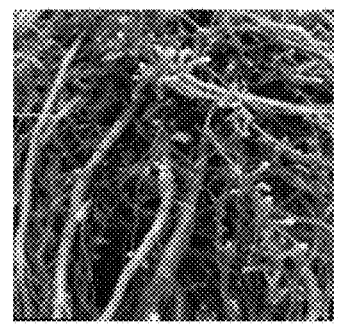
FIG. 7E shows nodulated roots of a representative control plant.
Figure 7F:
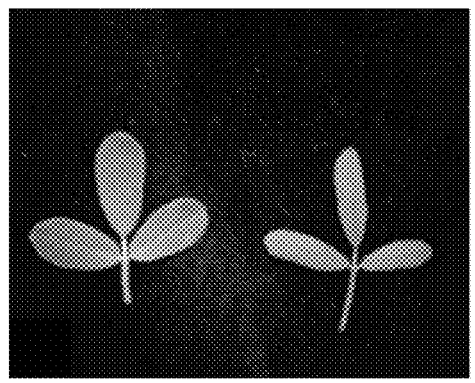
FIG. 7F shows a comparison of the leaf shape between control and transgenic plants. The adaxial side of the first fully expanded trifoliate leaf from the apex of a plant from each set is shown.
Figure 7G:
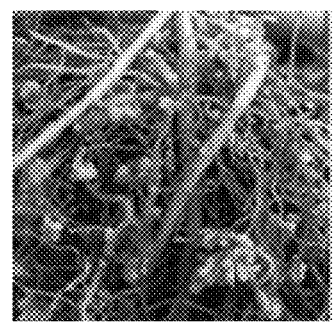
FIG. 7G shows nodulated roots of a representative transformed plant. Images represent what was seen in this set of plants and all following sets of plants produced by cuttings.

Increased SPS activity attained by introducing SPS transgene in different plants is associated with different phenotypes like increased fruiting and freeze tolerance, greater biomass in tomato, and a higher rate of cellulose synthesis. The transformant #7 along with a NT alfalfa plant was propagated via regeneration in tissue culture. The regenerants were moved into a vermiculite and sand mixture in pots in the greenhouse and were inoculated with S. meliloti. Under the symbiotic conditions, the transformants showed striking differences in the phenotype. FIGS. 7A-7G show phenotypic differences observed between the nodulated non-transformed and 35S-mzSPS (#7) transformed alfalfa plants. Images shown are of clonally propagated plants produced via tissue culture that were transferred to the greenhouse and kept under symbiotic $N_2$ fixing conditions. One of the more pronounced differences seen immediately between the two sets of plants was in leaf pigmentation. The leaves of the transformed plants displayed a darker shade of green (Bluish green) when compared to the NT plants (FIG. 7F). Leaf morphology was also altered in the transformed plants with the leaflets of each trifoliate being smaller in size and narrower in width (FIG. 7F). As these plants were allowed to grow, a clear effect on growth/height (FIGS. 7A and 7C, FIGS. 8A and 8B) was seen in the transformed plants along with a delay in the emergence of flowers. Only 12 percent of the 35S-mzSPS (#7) transformed plants showed signs of flowering approximately 10-14 days after 100 percent of the non-transgenic plants flowered (FIGS. 7B and 7D), about 8 weeks after being cut back. While the 35S-mzSPS transformed plants that showed signs of flowering had two to three flowers per inflorescence, the number of these also being very low at one to two per plant, the NT alfalfa plants had approximately 15-20 inflorescence per plant with each inflorescence containing approximately 10 flowers (FIGS. 7B and 7D). Additionally, the root system of the transformed plants had many more nodules, many of which formed large pronounced clusters compared to the non-transformed plants, which had a much smaller number of nodules, smaller size and in smaller clusters (FIGS. 7E and 7G). These trends were observed consistently in three consecutive sets of clonally propagated NT and 35S-mzSPS transformed plants produced via cuttings and when all plants were allowed to grow after being cut back to the crown/base.

Figure 8A:
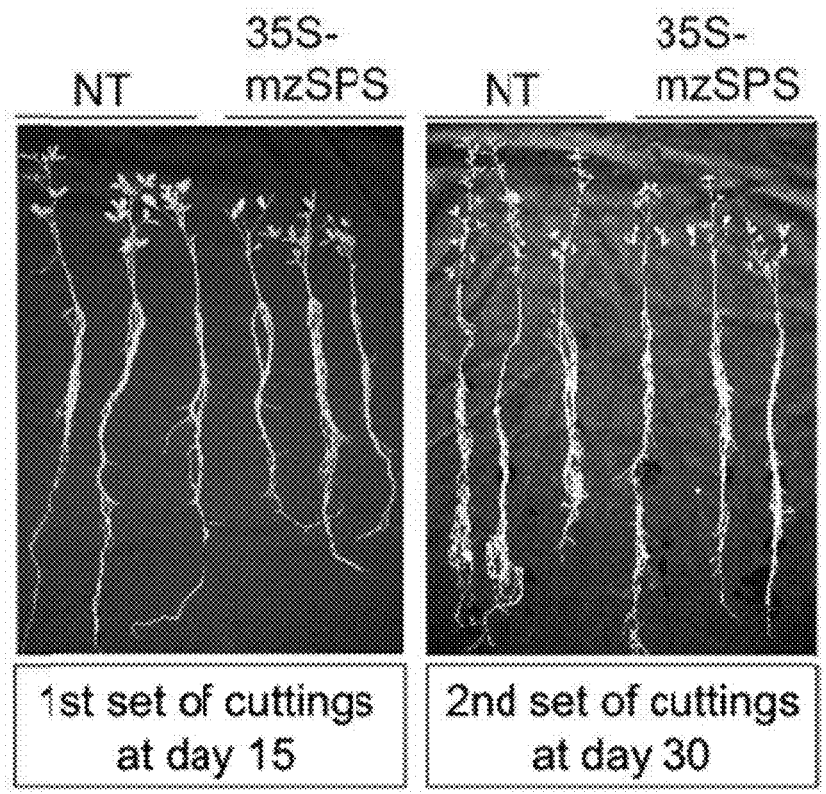
FIG. 8A shows the data from a representative experiment utilizing three plants from each class grown under symbiotic $N_2$ fixing conditions. Plants were removed from the pots from two different sets at day 17 (left panel, 8A) and day 30 (right panel 8A) to check for any differences in the roots. The plants seen in the right panel, 8A were used to determine stem:root ratios (maximum length).
Figure 8B:
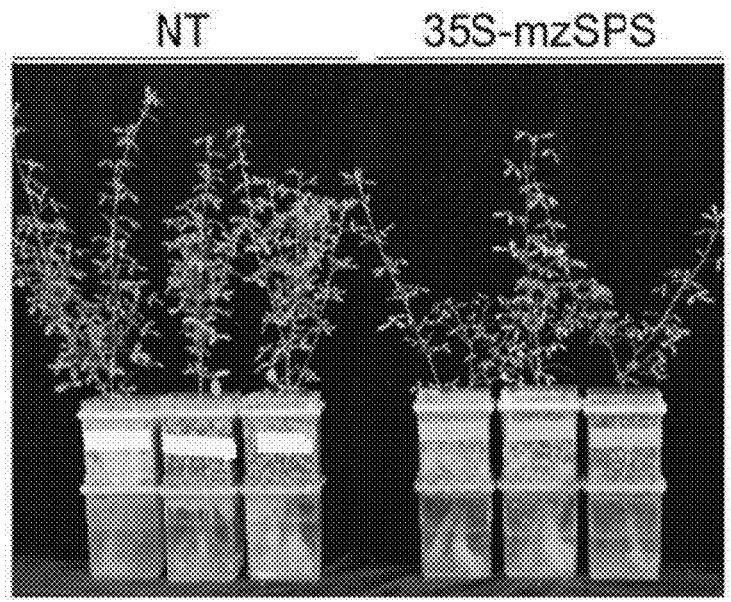
FIG. 8B shows a set of plants produced in a hydroponic system using magenta boxes to determine stem and root biomass production, as well as for later analysis of leaf and nodule tissue. Picture was taken at 42 days after these plants were established.
Figure 9A:
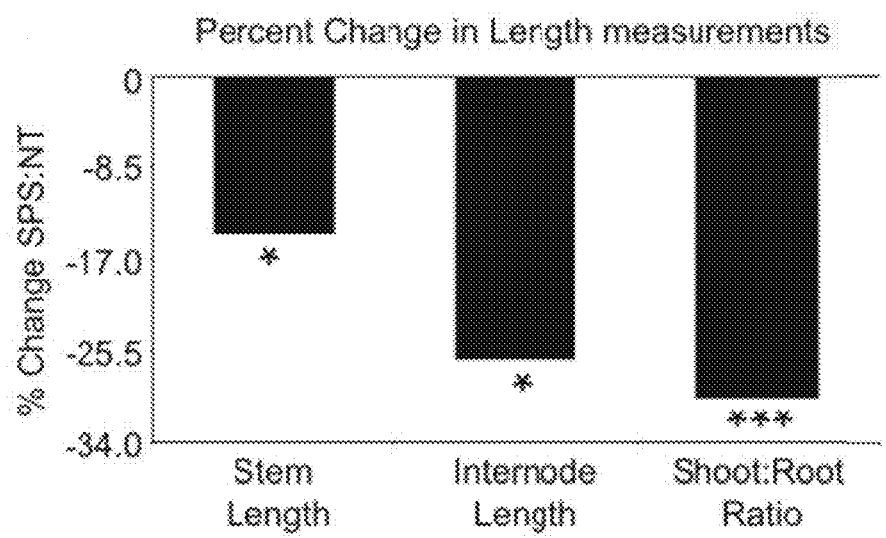
FIG. 9A shows stem length and internode length was determined from all the stems harvested from non-transformed and 35S-mzSPS transformed plants. Total shoot and root lengths were measured and values were used to calculate shoot:root ratios (length).
Figure 9B:
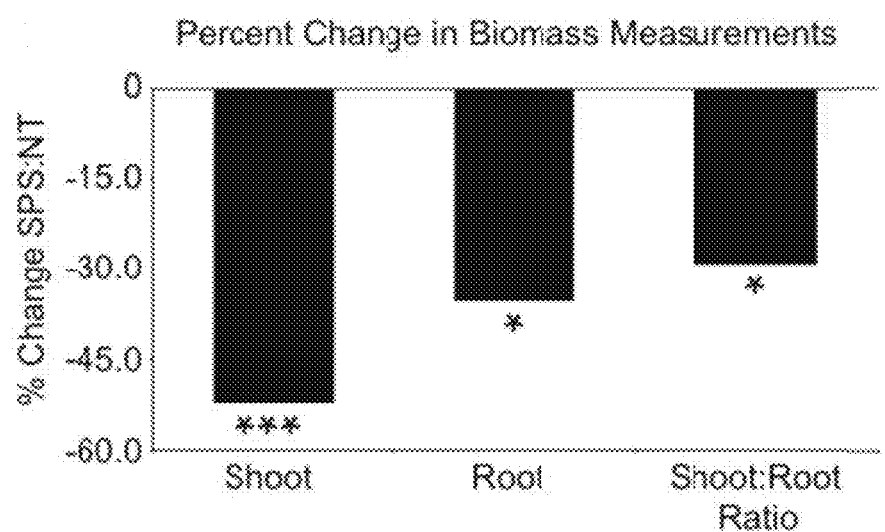
FIG. 9B shows shoot and root biomass of non-transformed and 35S-mzSPS transformed alfalfa plants were determined in another set of plants and the values were used to calculate shoot:root ratios (biomass weight). Percent change, calculated from averages in Tables A.5 and A.6, between the transformed and non-transformed plants are shown. (*, P≤0.05; ****, P≤0.001).

Shoot to root ratios, stem length, and internode length per stem were determined in both sets of plants to quantitatively evaluate the differences seen in plant growth at the phenotypic level. Twenty clonally propagated NT and 35S-mzSPS (#7) transformed alfalfa plants, produced via cuttings, were established in the greenhouse and inoculated with S. meliloti. FIGS. 8A and 8B show phenotypic differences in plant height and root size seen between the non-transformed and 35S-mzSPS transformed alfalfa plants. Several sets of cuttings of non-transformed and 35S-mzSPS transformed plants were produced and the root and shoot size and mass were measured. Approximately 30 days post inoculation (FIG. 8A, right panel and 8B), total shoot and root length was measured in each plant to calculate shoot to root ratios (length). While no significant difference was seen in root length between the two sets of plants, the stem length was approximately 22 percent lower in the 35S-mzSPS transformed (#7) plants (data not shown; P<0.01). FIGS. 9A and 9B show percent change in plant growth parameters between $N_2$ fixing non-transformed and 35S-mzSPS transformed alfalfa plants grown under greenhouse conditions. As seen in FIG. 9A, shoot to root ratios (length) derived from the above values were approximately 30 percent lower in the transformed plants compared to the NT plants (P<0.01). Moreover, shoot and root biomass (wet weight) was approximately 52 and 35 percent lower, respectively, in the transformed plants (FIG. 9B and Table A.6).

TABLE A.6

Shoot and root biomass measurements of alfalfa non-transformed and 35S-mzSPS transformed plants grown under symbiotic $N_2$ fixing conditions.

| Samples | Shoot Biomass | | | Root Biomass | | | Shoot:Root Ratio | | |
| --- | --- | --- | --- | --- | --- | --- | --- | --- | --- |
| N2 Fixing | Average | S.E. | t-test | Average | S.E. | t-test | Average | S.E. | t-test |
| NT | 4.06 | ±0.13 | 0.000 | 4.12 | ±0.19 | 0.034 | 1.05 | ±0.04 | 0.046 |
| SPS | 1.94 | ±0.07 | | 2.67 | ±0.11 | | 0.74 | ±0.02 | |
| % Change | −52.22 | | | −35.19 | | | −29.52 | | |

The values obtained from these measurements were used to calculate shoot:root biomass ratios (wet weight) and the transformed plants were significantly lower when compared to the non-transformed plants (FIG. 9B). The experiment was repeated and similar results were obtained. This data demonstrated a negative effect of the transgene on plant growth in the 35S-mzSPS transformed plants when kept under symbiotic $N_2$ fixing conditions. However, the reduction in the length of the internodes of the transformed plants represented an increase in the leaf to stem ratios, which is indicative of enhanced forage quality. The phenotype exhibited by transformant #7 was also displayed by all other independent transformants with the 35S-mzSPS gene that were analyzed (data not shown), confirming the phenotype to be a result of increased SPS activity.

Figure 10:
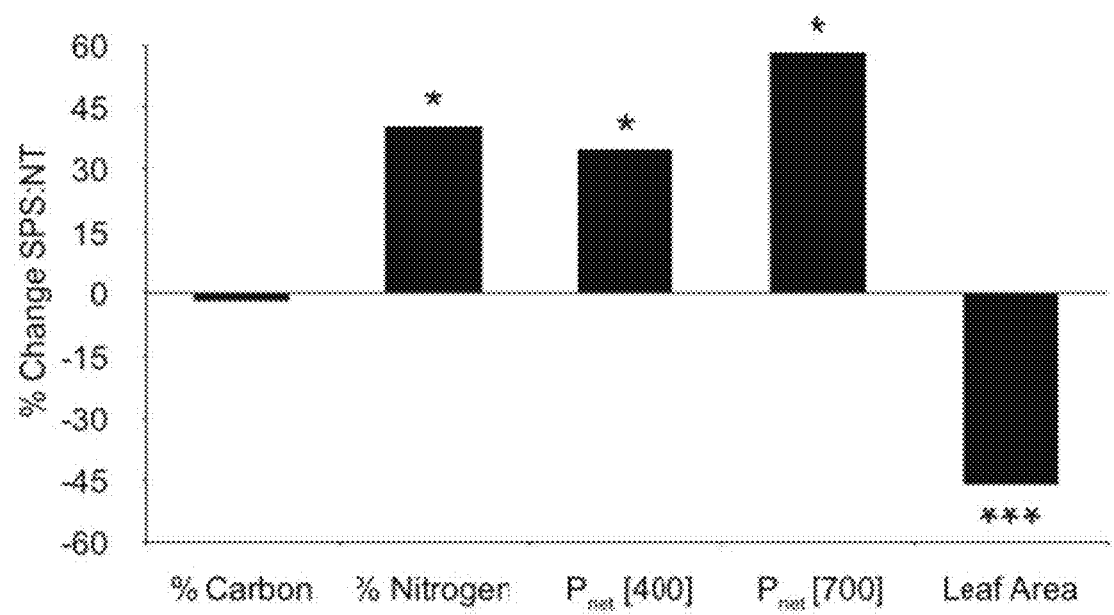
FIG. 10 shows percent change in the leaf photosynthetic rates, and changes in total C and N content between non-transformed and 35S-mzSPS transformed plants.

Referring to FIG. 10, percent change in leaf carbon and nitrogen content (% carbon and nitrogen, respectively), net photosynthetic rates under ambient ($P_{net}$ [400]) and elevated ($P_{net}$ [700]) $CO_2$ conditions, and leaf area between non-transformed and 35S-mzSPS transformed plants was determined from data in Table A.3 below.

TABLE A.3

Leaf photosynthetic, structural, and chemical characteristics of non-transformed and 35S-mzSPS transformed plants.

| Sample | % Carbon Average | S.E. | % Nitrogen Average | S.E. | Amax 400 umol Average | S.E. | Amax 700 umol Average | S.E. | Leaf area Average | S.E. |
|---|---|---|---|---|---|---|---|---|---|---|
| NT | 41.4 | ±0.3 | 3.3 | ±0.2 | 15.8 | ±0.48 | 18.1 | ±0.8 | 2.6 | ±0.06 |
| 35S-mzSPS | 40.7 | ±0.5 | 4.7 | ±0.1 | 21.29 | ±0.31 | 28.6 | ±0.7 | 1.4 | ±0.01 |
| % change | −1.7 | | 42.4 | | 34.7 | | 58.0 | | −46.2 | |
| t-Test | 0.68 | | 0.04 | | 0.01 | | 0.01 | | 0.00 | |

P values were calculated using Students t-test analysis (*, $P \leq 0.05$; ***, $P \leq 0.001$). Photosynthetic rates in the 35S-mzSPS transformed plants were approximately 35 and 58 percent ($P \leq 0.05$) higher under ambient and elevated $CO_2$ conditions, respectively, when compared to the NT plants. Moreover, the 35S-mzSPS transgenic plants showed a higher increase ($P \leq 0.05$) in photosynthetic rates ($P_{net}$), approximately 35 percent under ambient $CO_2$, compared to the $P_{net}$ values taken under elevated $CO_2$ conditions (data not shown). While the NT plants showed an approximately 14 percent increase in photosynthetic rates when comparing $P_{net}$ values of the two $CO_2$ conditions, this increase was not significant (P=0.38). Furthermore, the average leaf area of each trifoliate measured for $P_{net}$, was approximately 46 percent lower in the transformed plants when compared to the NT plants (FIG. 10 and Table A.3). Thus, the 35S-mzSPS transformed plants exhibited higher photosynthetic rates under both $CO_2$ conditions, albeit the smaller leaf size, and responded better to elevated $CO_2$ conditions as shown by the higher increase in $P_{net}$ values when comparing $P_{net}$ under the two $CO_2$ conditions.

Figure 11:
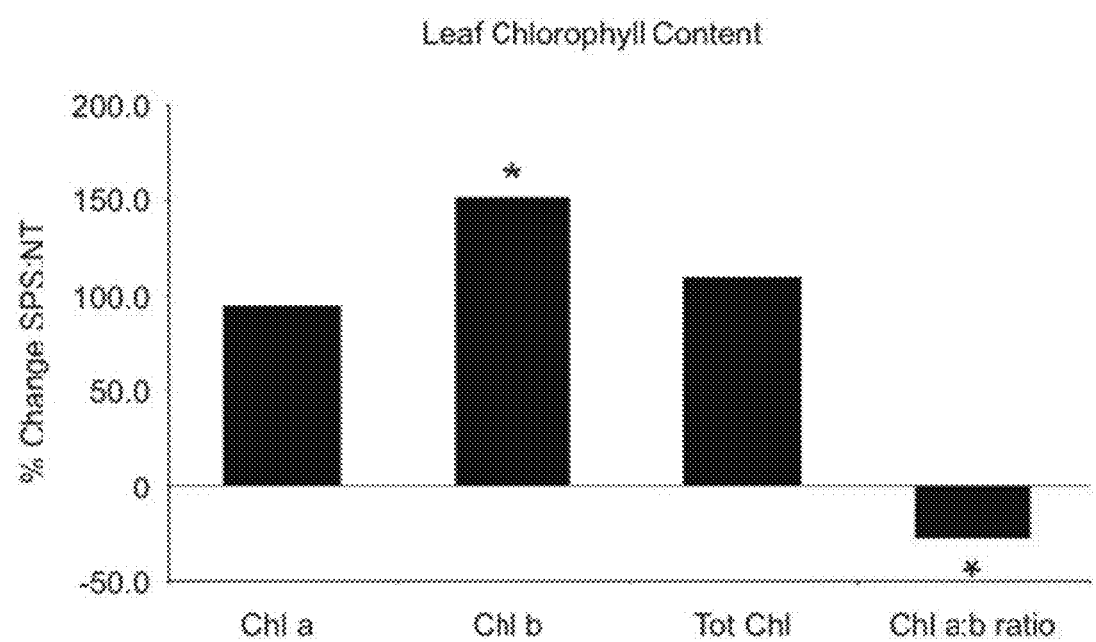
FIG. 11 shows percent change in the leaf chlorophyll content in the non-transformed and 35S-mzSPS transformed plants. Percent change in leaf chlorophyll content calculated from data in Table A.4 of the two sets of plants. P values were calculated using Students t-test analysis (*, P≤0.05).

Moreover, the difference in pigmentation in the leaves of the transformed plants (FIGS. 8A and 8B) suggest a change in the nitrogen status of the plants. As such, chlorophyll content and elemental composition of carbon and nitrogen were determined in the leaves of the NT and 35S-mzSPS transgenic alfalfa plants to address any changes in these parameters. As seen in FIG. 11 and Table A.4 below, pigment analysis of the 35S-mzSPS transformed plants showed approximately a 100 and 150 percent increase in the levels of chlorophyll a and chlorophyll b, respectively, when compared to the NT plants.

TABLE A.4

Leaf chlorophyll content of alfalfa non-transformed and 35S-mzSPS transformed plants.

| Sample | Chl a Average | S.E. | Chl b Average | S.E. | Tot Chl Average | S.E. | Chl a:b ratio Average | S.E. |
|---|---|---|---|---|---|---|---|---|
| NT | 481.9 | ±28.8 | 175.1 | ±15.3 | 656.92 | ±43.9 | 2.44 | ±0.11 |
| 35S-mzSPS | 941.0 | ±97.5 | 439.5 | ±43.9 | 1380.44 | ±140.4 | 1.77 | ±0.06 |
| % change | 95.3 | | 151.4 | | 110.1 | | −27.5 | |
| t-Test | 0.078 | | 0.034 | | 0.059 | | 0.024 | |

These values were combined and a similar trend was seen with the transformed plants exhibiting approximately 110 percent higher increase in total chlorophyll content. Statistical analysis of the three data sets showed significant changes in the levels of chlorophyll b (FIG. 11; Table A.4; $P \leq 0.05$). Elemental analysis of the leaves showed no significant difference in carbon content between the two sets of plants (FIG. 10; Table A.3; P=0.68). Conversely, nitrogen content was approximately 42 percent higher in the transformed plants when compared to the NT plants ($P \leq 0.05$). These results indicate the 35S-mzSPS transgenic plants, under symbiotic $N_2$-fixing conditions, have more available nitrogen than NT plants as represented by the higher nitrogen and chlorophyll content seen in the leaves. This would further imply that the increased N level is due to enhanced nodulation and the accompanying increase in $N_2$-fixation.

Figure 13:
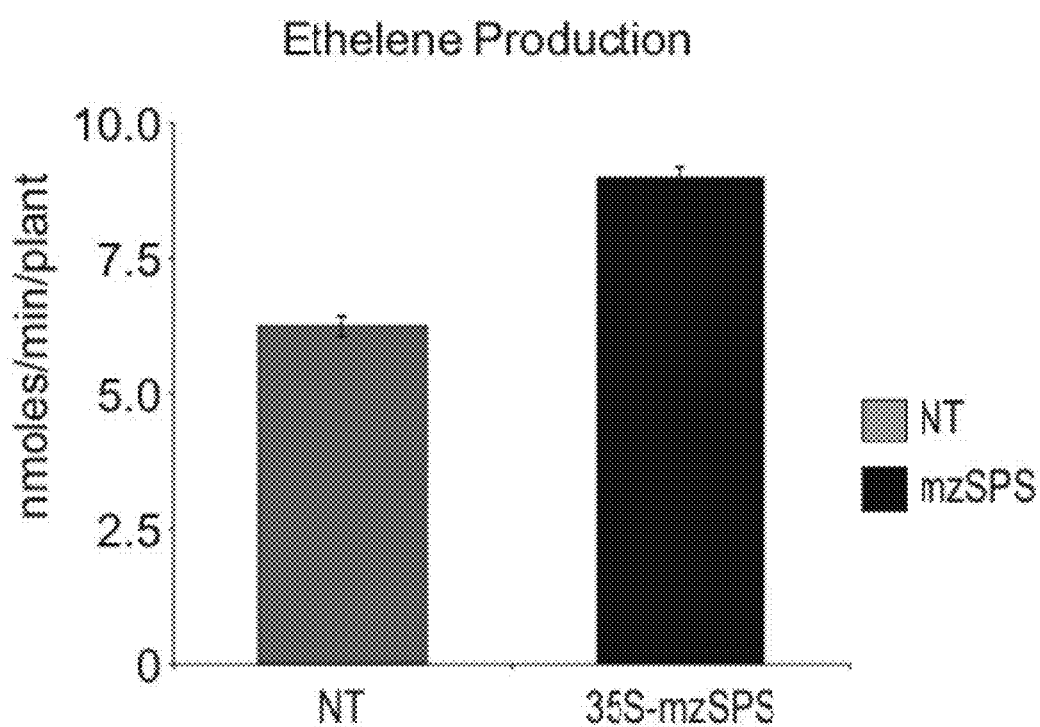
FIG. 13 shows ethylene production of five non-transformed and 35S-mzSPS transformed alfalfa plants. The estimation of nitrogenase activity in non-transformed (NT) and 35S-mzSPS alfalfa transformed plants was determined via the acetylene reduction assay as described in materials and methods. Average nmoles $C_2H_4 \cdot min^{-1} \cdot plant^{-1}$ of five clonally propagated NT and 35S-mzSPS plants±SE are shown. *P<0.05 with two-tailed Students t-test.

To determine any changes in $N_2$ fixation rates, acetylene-reduction by nitrogenase was assayed using the entire root system of NT and transformed alfalfa plants. As seen in FIG. 13, the nodules of the transformed plants exhibited approximately 44 percent increase in the acetylene-reduction rates (ethylene production; $C_2H_4$ nmoles·min-1·plant-1) when compared to the NT plants. Therefore, the transformed plants showed enhanced $N_2$ fixation rates when compared to the NT plants.

Figure 14:
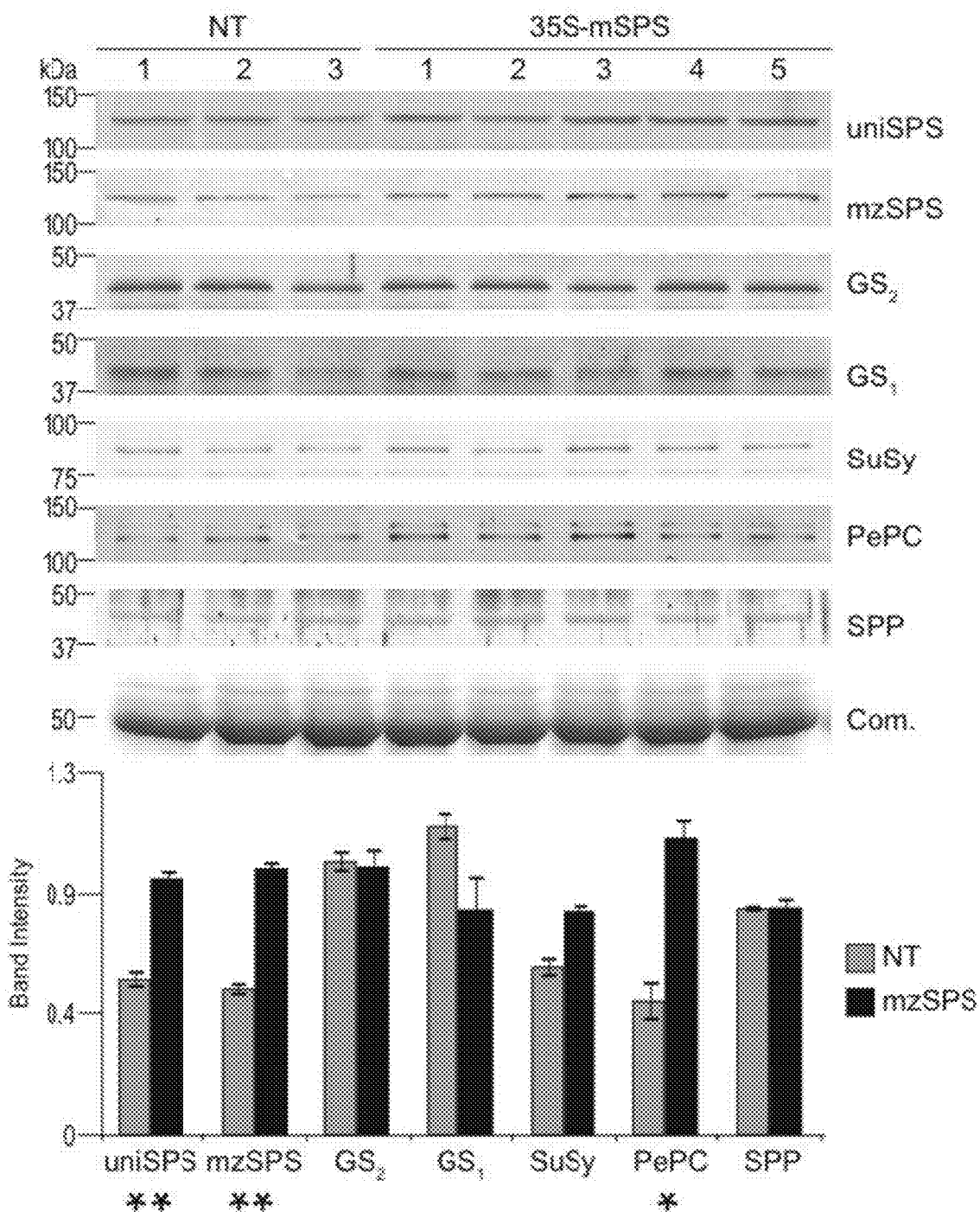
FIG. 14 shows a polypeptide analysis of carbon and nitrogen enzymes in the leaves of non-transformed and 35S-mzSPS transformed plants.

Referring to FIG. 14, total soluble protein, extracted from the leaves of the two classes of plants, was subjected to SDS-PAGE western blot analysis using antibodies specific to key enzymes in carbon and nitrogen metabolism. As previously seen in FIGS. 3A-C, significant accumulation of the maize SPS polypeptides was seen in the leaves of the transformed plants. The use of the universal and maize SPS antibodies showed a similar increase in band intensity of approximately 64 and 81 percent, respectively, in the immunoreactive bands corresponding to SPS in the protein extract of the transformed plants when compared to the extract from NT plants (FIGS. 3A-C). Total soluble protein (TSP) extracted from the leaves of the same non-transformed and 35S-mzSPS transformed alfalfa plants used in FIG. 6, was subjected to SDS-PAGE followed by western blot analysis using antibodies specific for sucrose phosphate synthase (uniSPS; 50 µg TSP) and Maize SPS-specific (mzSPS; 50 µg TSP)), glutamine synthetase ($GS_1$; 7 µg TSP and $GS_2$; 7 µg TSP), sucrose synthase (SuSy; 3 µg TSP), sucrose phosphate phosphatase (SPP; 3 µg TSP) and phosphoenolpyruvate carboxylase (PePC; 3 µg TSP). Immunoreactive bands and corresponding enzymes are shown with molecular weight markers (kDa). Coomassie stained gel (15 µg TSP) is shown to confirm protein loads. Band intensities of all bands were determined, normalized to band intensities obtained from the Coomassie stained gel, and average values±SE were plotted. *P<0.05, **P<0.01 with two-tailed Students t-test. While the antibodies showed affinity for the endogenous SPS, the higher level of SPS polypeptide accumulation seen in the transformed plants compared to NT plants, can be attributed to the maize SPS transgene protein. While no significant differences were seen in the accumulation of GS, Susy, or SPP polypeptides in the leaves of the transformed plants, a significant increase was seen in band intensities that corresponded to the immunoreactive bands of PePC (FIG. 14).

Figure 12:
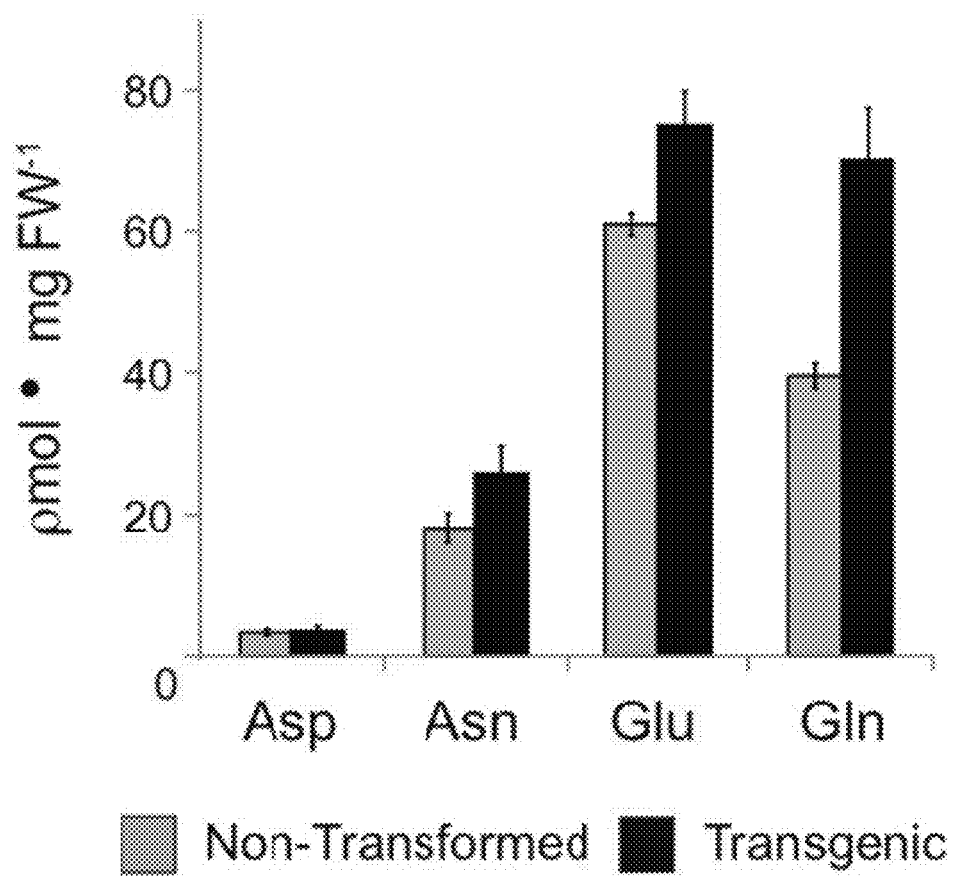
FIG. 12 shows an analysis of aspartate, asparagine, glutamate, and glutamine in the leaves of the 35S-mzSPS transformed plants.

Up-regulation of SPS activity has been shown to increase sink number and enhance sink strength in several plant species. The root nodules of legumes are a unique C sink in that they are metabolically highly active in fixing free N and assimilating the fixed nitrogen. Higher N content in the transformed plants compared to NT plants when grown under $N_2$-fixing conditions, suggests higher levels of $N_2$-fixation and assimilation in the nodules of the transformants (FIGS. 10, 11, and 12). In FIG. 12, amino acids were extracted from non-transformed and transformed alfalfa plants. Samples, along with standards for Asp, Asn, Glu, and Gln, were analyzed via liquid chromatography-mass spectroscopy (LCMS) to determine any change in the levels of these amino acids in the leaves of the transformed plants compared to control plants. Average values in pmol·mg $FW^{-1}$±S.E. bars are shown. Moreover, higher N metabolic activity in the nodules would imply higher import of sucrose from the leaves. As discussed earlier, the nitrogen fixation rates were higher in the transformants compared to the NT plants (FIG. 13).

To check if increased SPS activity in the photosynthetic tissues affects import of sucrose into the nodules which could eventually affect the expression of other genes encoding enzymes with roles in C and N metabolism, the levels of the several enzymes were checked in the nodules. Total soluble protein, extracted from the nodules of the two classes of plants, was subjected to SDS-PAGE western blot analysis using antibodies specific to key enzymes in carbon and nitrogen metabolism. A significant increase in the accumulation of SPS polypeptides was seen in the nodules of the transformed plants. As seen in FIG. 14, the presence of endogenous SPS in the nodules was confirmed via the use of the universal SPS antibody. The immunoreactive bands corresponding to SPS polypeptides (about 140 kDa) were of lower intensity in the protein extract from the NT plants when compared to the extract from the transformed plants (about 2.8 fold; P<0.05). The higher band intensity seen in the nodules of the transformed plants represents the accumulation of both the endogenous SPS and maize SPS polypeptides. A more pronounced difference between the two sets of plants in SPS polypeptide accumulation was seen with the use of the maize specific antibody.

Figure 15:
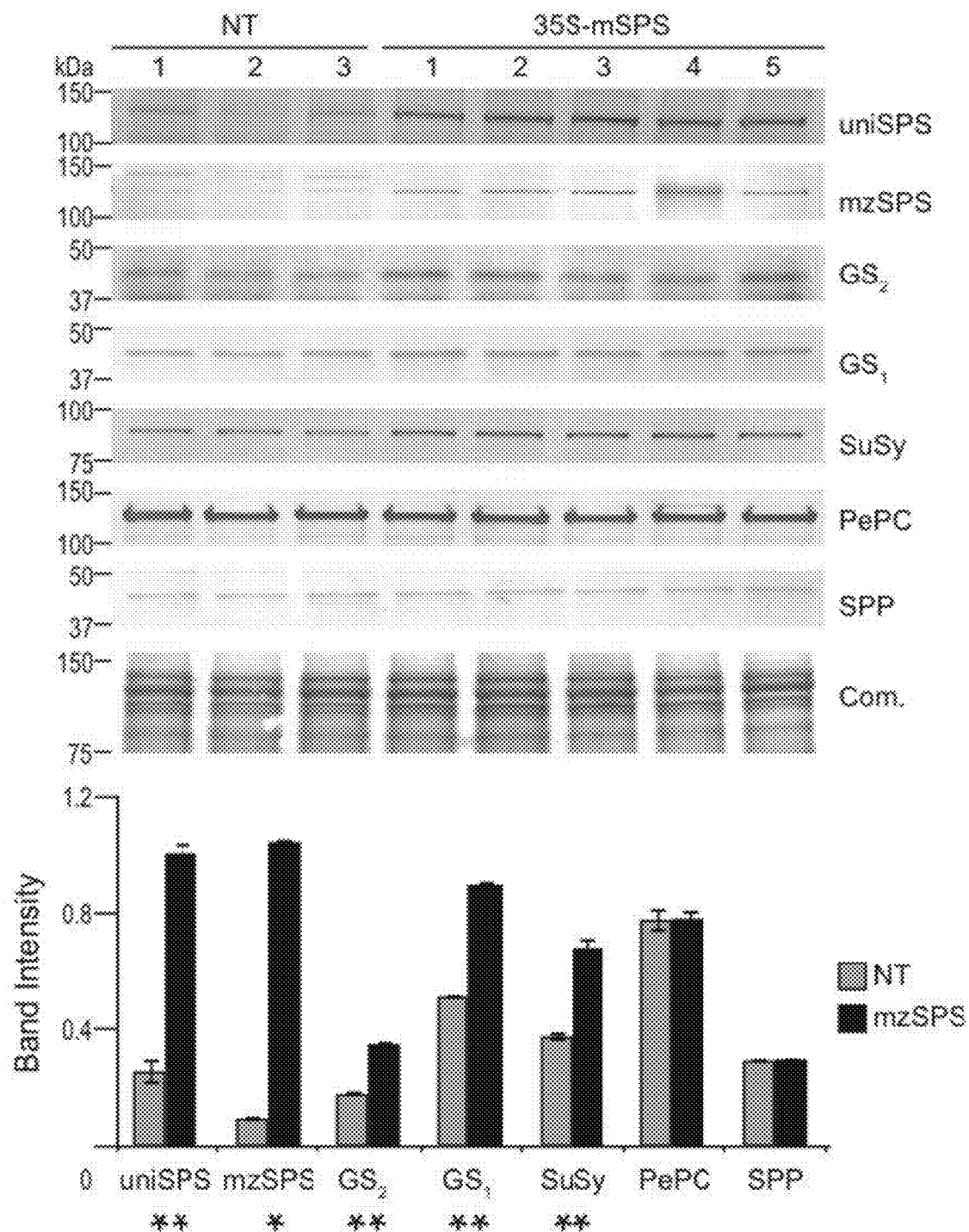
FIG. 15 shows a polypeptide analysis of carbon and nitrogen enzymes in the nodules of non-transformed and 35S-mzSPS transformed plants. Total soluble protein (TSP) extracted from the nodules of non-transformed and 35S-mzSPS transformed alfalfa plants was subjected to SDS-PAGE followed by western blot analysis using antibodies specific for sucrose phosphate synthase (uniSPS; 50 µg TSP) and Maize SPS-specific antibodies (mzSPS; 50 µg TSP)), glutamine synthetase ($GS_1$; 0.75 µg TSP and $GS_2$; 7 µg TSP), sucrose synthase (SuSy; 1.5 µg TSP), sucrose phosphate phosphatase (SPP; 3 µg TSP) and phosphoenolpyruvate carboxylase (PePC; 3 µg TSP). Immunoreactive bands and the corresponding enzymes are shown with molecular weight markers (kDa). Coomassie stained gel (15 µg TSP) shown to confirm loads. Band intensities of all the bands were determined, normalized to band intensities obtained from the Coomassie stained gel, and average values±SE are plotted. *P<0.05, **P<0.01 with two-tailed Students t-test.

However, no difference was seen between the two sets of plants in the band intensities of sucrose-6-phosphate phosphatase (SPP, about 40 and 50 kDa), an enzyme also involved in the synthesis of sucrose, along with SPS. Accumulation of the enzyme sucrose synthase (SuSy, about 90 kDa), known for its central role in modulating sink strength and maintaining proper nodule function was higher in the transformed plants, as shown by the average band intensities of the immunoreactive bands corresponding to SuSy (P<0.05, FIG. 14). Interestingly, no difference was exhibited between the two classes of plants in the accumulation of phosphoenolpyruvate carboxylase (about 110 kDa; P>0.05), which also plays an important role in the nodule by recycling carbon via anaplerotic $CO_2$ fixation. On the contrary, the nodules of the transformed plants exhibited a significant increase in the intensities of immunoreactive bands corresponding to cytosolic ($GS_1$, about 39 kDa) and plastidic ($GS_2$, about 42 kDa) glutamine synthetase of approximately 92 and 74 percent, respectively. While accumulation of PePC polypeptides showed no difference between the two classes of plants, the changes in $GS_1$ and $GS_2$ polypeptide accumulation is indicative of a response of these enzymes to the increased rates of $N_2$ fixation seen in the transformed plants (FIG. 15).

Figure 16:
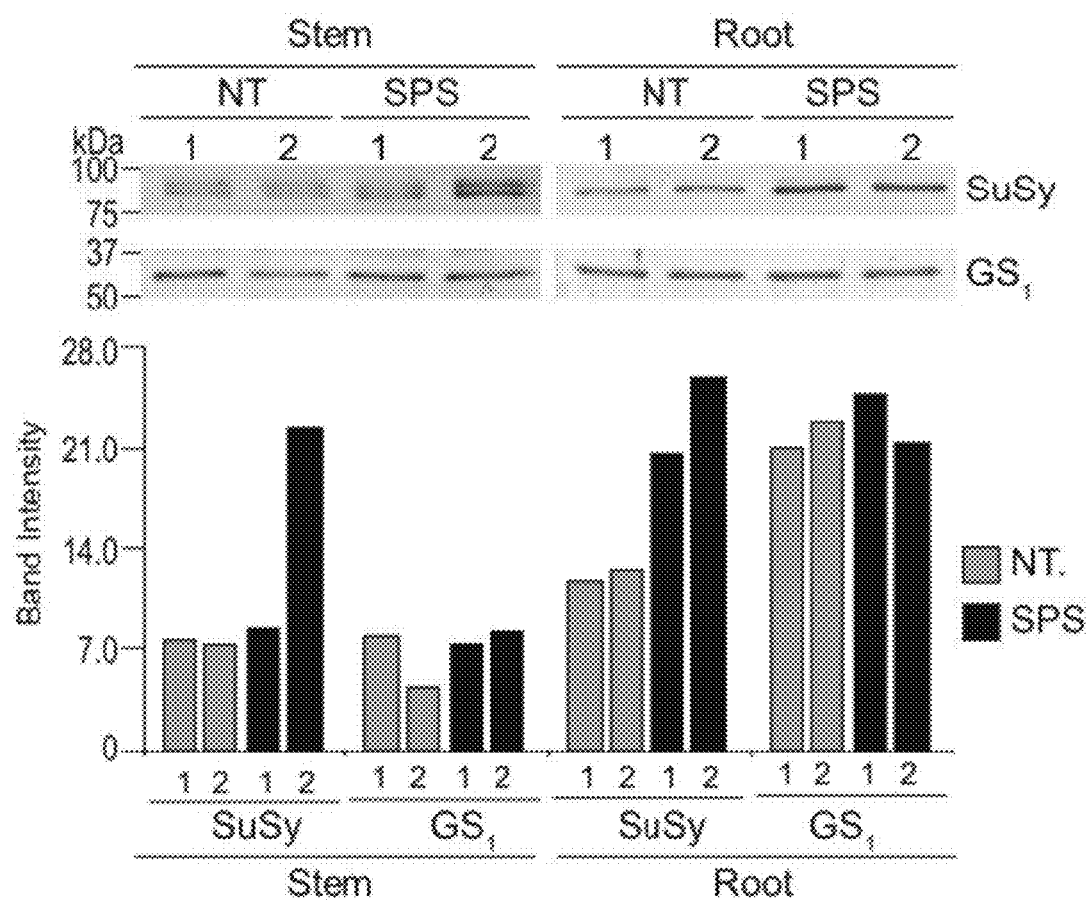
FIG. 16 shows an analysis of SPS and $GS_1$ polypeptide accumulation in the stem and roots of non-transformed and 35S-mzSPS transformed plants. Total soluble protein (TSP) extracted from the stems and roots of the non-transformed and 35S-mzSPS transformed alfalfa plants was subjected to SDS-PAGE followed by western blot analysis using antibodies specific for glutamine synthetase ($GS_1$; 1.5 µg TSP) and sucrose synthase (SuSy; 1.5 µg TSP). Immunoreactive bands and corresponding enzymes are shown with molecular weight markers (kDa). Band intensities of all blots were determined and values are shown.

In addition to the nodules, other C sinks such as the roots and stems may be affected by the constitutive expression of maize SPS in alfalfa. To address this, SuSy and GS polypeptide accumulation was analyzed in TSP, extracted from the stems and roots of NT, and transformed plants to determine any changes in sink strength or ammonium assimilatory capabilities in these organs. As seen in FIG. 16, the accumulation of GS protein was similar between the two classes of plants in both sets of tissues. However, a substantial increase was seen in SuSy polypeptide accumulation in the roots of the transformed plants and there was in general an increase also in the stem. Nonetheless, the 35S-mzSPS transformed plants clearly exhibited enhanced sink strength in heterotrophic tissues as seen by the higher level of SuSy protein in these tissues. Moreover, these plants showed improved $N_2$-fixing capabilities and the higher levels of GS polypeptide in the nodules are indicative of enhanced $NH_4^+$ assimilatory capabilities.

The leaves of forage crops are of higher quality than stems and the previous data indicate the 35S-mzSPS transformed plants have a higher leaf:stem ratio when compared to the NT plants (FIGS. 8 and 9). Moreover, the transformed plants showed higher nitrogen and chlorophyll content in the leaves as well as a delay in flowering time which implies a delay in senescence (FIGS. 10 and 11). Hence, a complete nitrogen profile and fiber analysis was conducted on the two sets of plants to determine if there were any changes in forage quality in the transformed plants.

Figure 17A:
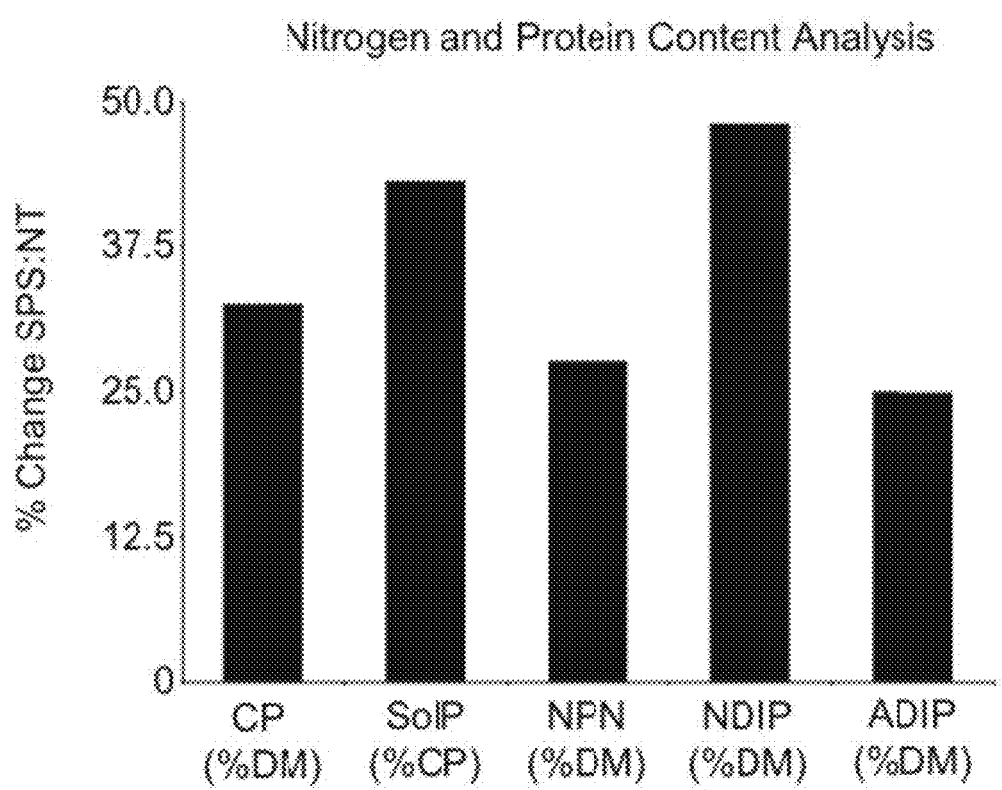
FIG. 17A shows protein content/nitrogen profile analysis that was performed on lyophilized shoot tissue. Percent change between the transformed and non-transformed plants of crude protein (CP), soluble protein (SoIP), non-protein nitrogen (NPN), acid detergent insoluble protein (ADIP), and neutral detergent insoluble protein (NDIP) are shown.
Figure 17B:
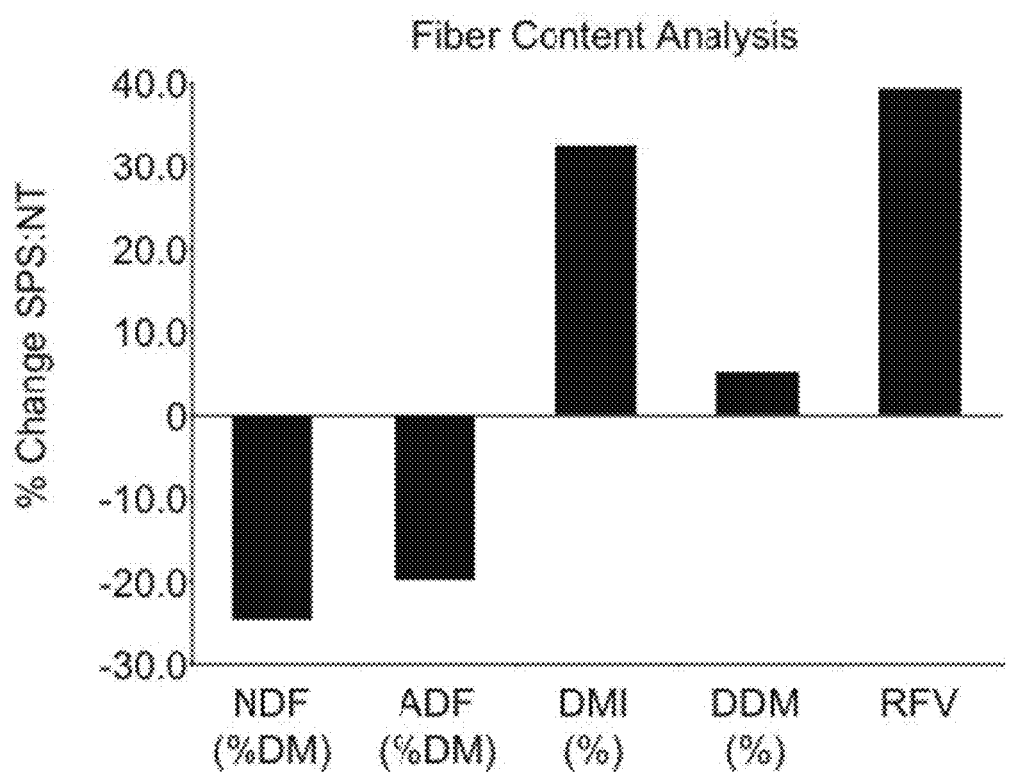
FIG. 17B shows fiber content analysis that was done on the same tissue used in 17A. Acid detergent fiber (ADF) and neutral detergent fiber (NDF) were used to calculate digestible dry matter (DDM) and dry matter intake (DMI), respectively. RFV values are derived from DDM and DMI. Percent change for each parameter was determined using values in Table A.7.

FIGS. 17A and 17B show the forage quality of non-transformed and 35S-mzSPS transformed alfalfa plants under symbiotic $N_2$ fixing conditions. The shoots of twenty clonally propagated NT and 35S-mzSPS transformed plants, kept under symbiotic $N_2$-fixing conditions, were harvested 40 days after being cut back to the crown/base and freeze dried via lyophilization. Data from pooled tissue is presented as percent of dry matter with the exception of soluble protein (SoIP) which is presented as percent of crude protein (CP). As seen in FIG. 17 and Table A.7, CP percentages in the shoots of the transformed plants were approximately 33 percent higher than the NT plants.

TABLE A.7

Forage quality and value of shoots harvested from alfalfa non-transformed and 35S-mzSPS transformed plants grown under different nitrogen conditions.

| Sample $N_2$ Fixing | CP (% DM) | SolP (% CP) | NPN (% DM) | NDIP (% DM) | ADIP (% DM) | NDF (% DM) | ADF (% DM) | DMI (%) | DDM (%) | RFV |
|---|---|---|---|---|---|---|---|---|---|---|
| NT | 18.2 | 38.0 | 2.9 | 0.8 | 0.5 | 30.6 | 23.4 | 3.9 | 70.7 | 215.0 |
| 35S-SPS | 24.2 | 41.0 | 3.7 | 1.2 | 0.7 | 23.1 | 18.8 | 5.2 | 74.3 | 299.5 |
| % Change | 32.6 | 43.1 | 27.6 | 48.1 | 25.0 | −24.5 | −19.8 | 32.5 | 5.1 | 39.3 |

TABLE A.7-continued

Forage quality and value of shoots harvested from alfalfa non-transformed and 35S-mzSPS transformed plants grown under different nitrogen conditions.

| 5 mM NH$_4$NO$_3$ | CP (% DM) | SolP (% CP) | NPN (% DM) | NDIP (% DM) | ADIP (% DM) | NDF (% DM) | ADF (% DM) | DMI (%) | DDM (%) | RFV |
|---|---|---|---|---|---|---|---|---|---|---|
| NT | 21.7 | 44.0 | 4.3 | 0.7 | 0.4 | 27.3 | 20.4 | 4.4 | 73.0 | 249.1 |
| 35S-SPS | 25.4 | 37.0 | 5.7 | 0.8 | 0.5 | 18.8 | 14.7 | 6.4 | 77.4 | 383.0 |
| % Change | 17.2 | −1.5 | 33.1 | 20.0 | 33.3 | −31.0 | −27.9 | 45.0 | 6.1 | 53.8 |

| % Change NH$_4$NO$_3$:N$_2$ | CP | SolP | NPN | NDIP | ADIP | NDF | ADF | DMI | DDM | RFV |
|---|---|---|---|---|---|---|---|---|---|---|
| NT | 18.7 | 37.4 | 46.9 | −17.7 | −25.0 | −10.8 | −12.9 | 12.1 | 3.3 | 15.8 |
| 35S-SPS | 4.9 | −5.4 | 53.2 | −33.3 | −20.0 | −18.5 | −21.7 | 22.6 | 4.3 | 27.9 |

Moreover, the percent of SolP and the percent non-protein nitrogen (NPN) in these plants increased approximately 43 and 28 percent, respectively. The amount of protein (nitrogen) bound to fiber, defined as neutral detergent insoluble protein (NDIP) and acid detergent insoluble protein (ADIP), was generally low in both sets of plants (Table A.7). Nevertheless, a 25 and 48 percent increase in the values of ADIP and NDIP, respectively, was seen in the 35S-mzSPS transformed plants (FIG. 17A). Values determined by NDIP analysis comprise a fraction of the protein (nitrogen) in fiber that is both slowly degradable by rumen microbes and digestible in the small intestine of animals, while the values of ADIP analysis, a component of NDIP, represents protein (nitrogen) in fiber that is highly resistant to microbial and mammalian enzymes and consequently, completely unavailable to both. An estimate of the degradable/digestible fraction of protein (nitrogen) bound to fiber was derived by subtracting the values of ADIP from NDIP of which, the 35S-mzSPS transformed plants demonstrated approximately 68 percent higher level of degradable/digestible protein (nitrogen) bound to fiber than the NT plants (data not shown).

Furthermore, neutral detergent fiber (NDF) and acid detergent fiber (ADF) analysis was performed on the same tissue from both sets of plants to evaluate fiber content. The NDF values, representing total cell wall components was approximately 25 percent lower in the 35S-mzSPS transformants when compared to the NT plants. Similarly, the most indigestible cell wall component (such as lignin), represented as ADF values showed an approximate drop of 20 percent in the 35S-mzSPS transformed plants. Dry matter digestibility (DDM) and dry matter intake (DDI) of the two sets of plants were determined using the ADF and NDF values, respectively. Estimations of DDM and DDI were further used to calculate the relative feed value (RFV), an index and ranking forages by potential digestible dry matter intake. As seen in FIG. 17B, more or less similar values of DDM were seen in both sets of plants with increase in the 35S-mzSPS transformed plants compared to the NT plants. However, a substantial increase in DDI and the calculated RFV content was seen in the transformed plants of approximately 33 and 39 percent, respectively.

Taken together, the 35S-mzSPS alfalfa transformed plants showed a substantial increase in the level of readily available protein (CP, SolP, and NPN) and degradable/digestible protein bound to fiber. Moreover, the lower fiber content in the transformed plants translated into higher RFV content enhancing potential digestible dry matter intake when compared to the NT plants. These results validate the nutritional superiority of the 35S-mzSPS transformed plants over the NT plants when kept under symbiotic N$_2$-fixing conditions. Moreover, the reduction in fiber content shows that up regulation of SPS in alfalfa results in the reduction of cell wall synthesis or production of structural carbohydrates.

The 35S-mzSPS transformed plants have some characteristics that are similar to those seen in hyper-nodulating soybean plants, such as an increase in nodule number, darker green leaf pigmentation, and a reduction in shoot biomass. Hence, it was hypothesized that the alfalfa 35S-mzSPS transformed plants were diverting carbon, typically used for growth and development, to the root nodules to meet the increased demand of carbon in these metabolically active carbon sinks. To test this hypothesis, another set of 20 NT and 35S-mzSPS transformed alfalfa plants were clonally propagated under greenhouse conditions. These plants, in contrast to the previous experiments, were kept under non-symbiotic N$_2$ fixing conditions by feeding them about 5 mM NH$_4$NO$_3$ and penicillin [100 µg·mL-1] in 0.5× Hoagland's nutrient solution. These experiments were conducted in parallel with the sets of plants grown under symbiotic N$_2$ conditions as described in previous sections.

TABLE A.5

Plant growth (length) measurements of alfalfa non-transformed and 35S-mzSPS transformed plants grown under different nitrogen conditions.

| Samples | Stem Length | | | Internode Length | | | Shoot:Root Ratio | | |
|---|---|---|---|---|---|---|---|---|---|
| | Average | S.E. | t-test | Average | S.E. | t-test | Average | S.E. | t-test |
| N$_2$ Fixing | | | | | | | | | |
| NT | 6.75 | ±0.07 | 0.04 | 1.22 | ±0.01 | 0.02 | 1.39 | ±0.02 | 0.00 |
| 35S-mzSPS | 5.77 | ±0.6 | | 0.90 | ±0.02 | | 0.98 | ±0.02 | |
| % Change | −14.62 | | | −26.30 | | | −29.90 | | |
| 5 mM NH$_4$NO$_3$ | Average | S.E. | t-test | Average | S.E. | t-test | Avereage | S.E. | t-test |

TABLE A.5-continued

Plant growth (length) measurements of alfalfa non-transformed and 35S-mzSPS transformed plants grown under different nitrogen conditions.

| NT | 7.84 | ±0.02 | 0.00 | 1.68 | ±0.00 | 0.00 | 1.13 | ±0.02 | 0.52 |
|---|---|---|---|---|---|---|---|---|---|
| SPS | 6.36 | ±0.02 | | 1.07 | ±0.00 | | 1.19 | ±0.01 | |
| % Change | −18.89 | | | −36.66 | | | 5.38 | | |

| % Change $NH_4NO_3:N_2$ Fixing | Stem Length | Intermode Length | Shoot:Root Ratio |
|---|---|---|---|
| NT | 16.03 | 37.65 | −18.68 |
| 35-mzSPS | 10.23 | 18.30 | 22.24 |

Figure 18:
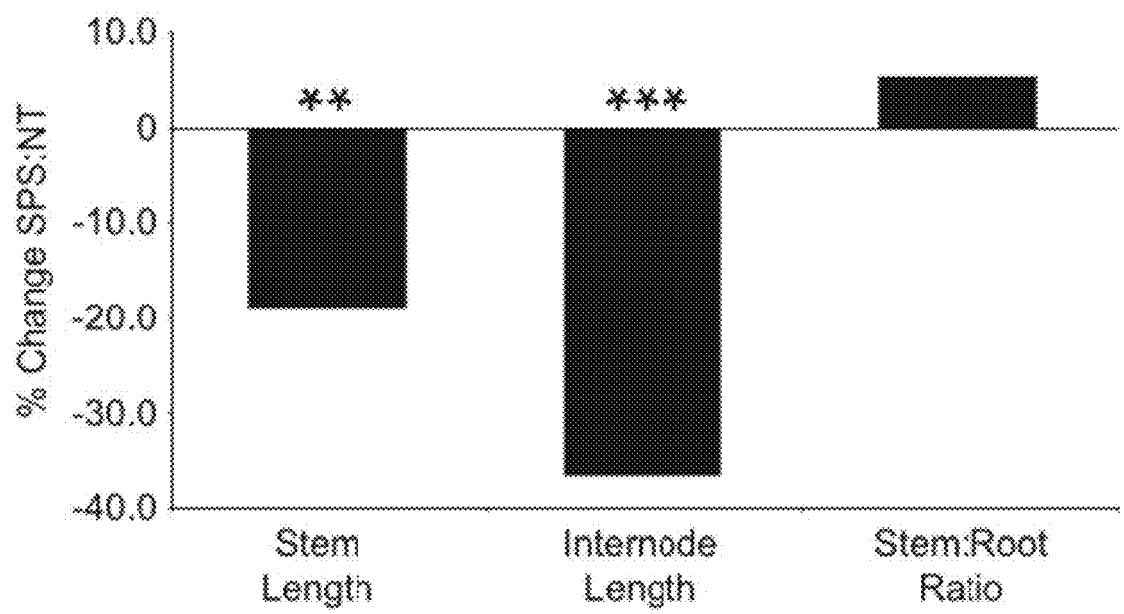
FIG. 18 shows the percent change in plant growth parameters between 5 mM $NH_4NO_3$ fed non-transformed and 35S-mzSPS transformed alfalfa plants grown under greenhouse conditions. Stem length and internode length was determined from all stems harvested from non-transformed and 35S-mzSPS transformed plants. Total shoot and root lengths were measured and values were used to calculate shoot:root ratios (length). Percent change, calculated from averages in Table A.5, between the transformed and non-transformed plants are shown. (, P≤0.01; *, P≤0.001).

Interestingly, quantitative analysis of stem and internode length showed similar trends with the exception of the shoot to root ratios (length) that showed no significant differences between the 35S-mzSPS transformed and NT plants (FIG. 18 and Table A.5; P=0.52). The total shoot and root lengths, however, were only measured once in the set of plants fed $NH_4NO_3$ and the measurement were done on the initial growth of the shoots after cuttings were established. Moreover, when comparing data of plants fed $NH_4NO_3$ with plants kept under symbiotic $N_2$ fixing conditions, only the 35S-mzSPS transformed plants demonstrated an increase of approximately 22 percent, in shoot to root ratios (Table A.5). In contrast to the transformed plants, the shoot to root ratios of the NT plants dropped approximately 19 percent in the set of plants fertilized with $NH_4NO_3$. Nonetheless, significant differences were seen in the average stem and internode length, of which, the 35S-mzSPS transformed plants were approximately 19 and 37 percent lower, respectively, than the NT plants. Shoots were cut back two consecutive times and similar trends were consistently seen in transformed plants. When comparing data of plants grown under the two different nitrogen regimens, the NT plants demonstrated a larger increase in stem and internode lengths of approximately 16 and 38 percent, respectively, when fed about 5 mM $NH_4NO_3$, while the 35S-mzSPS transformed plants showed about 10 and 18 percent increase. Moreover, the transformed plants fed $NH_4NO_3$ exhibited similar delays in flower emergence and changes in leaf pigmentation as previously described for the plants grown under symbiotic $N_2$ fixing conditions (Data not shown).

Figure 19A:
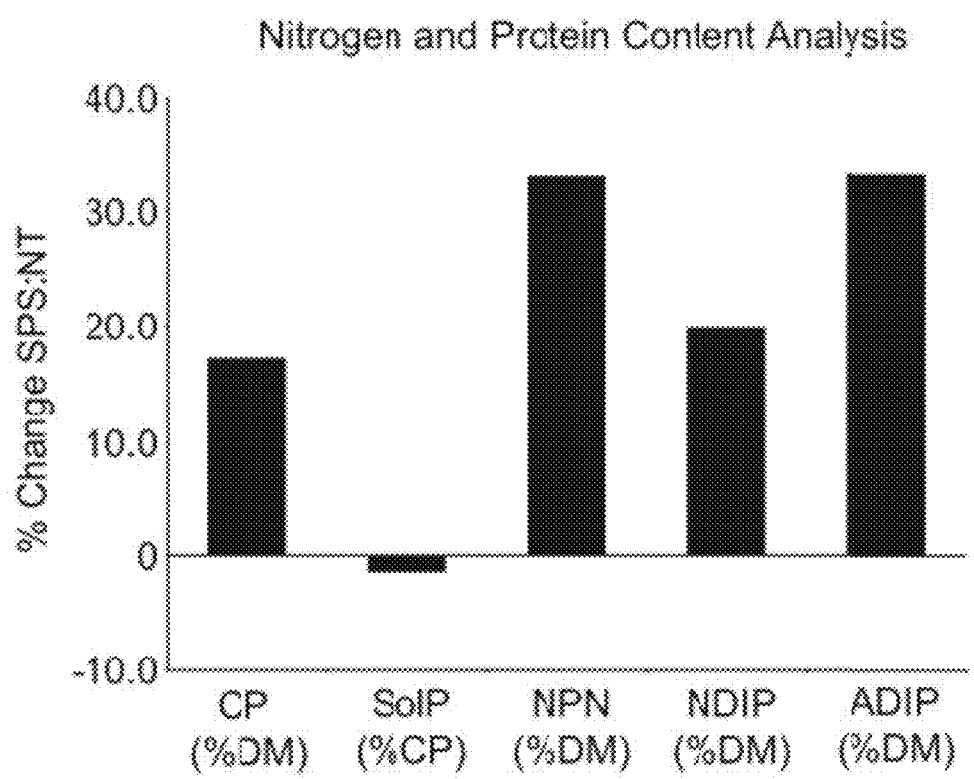
FIG. 19A shows protein (nitrogen) profile of the two sets of plants: Crude protein (CP), soluble protein (SoIP), non-protein nitrogen (NPN), acid detergent insoluble protein (ADIP), and neutral detergent insoluble protein (NDIP) are shown.
Figure 19B:
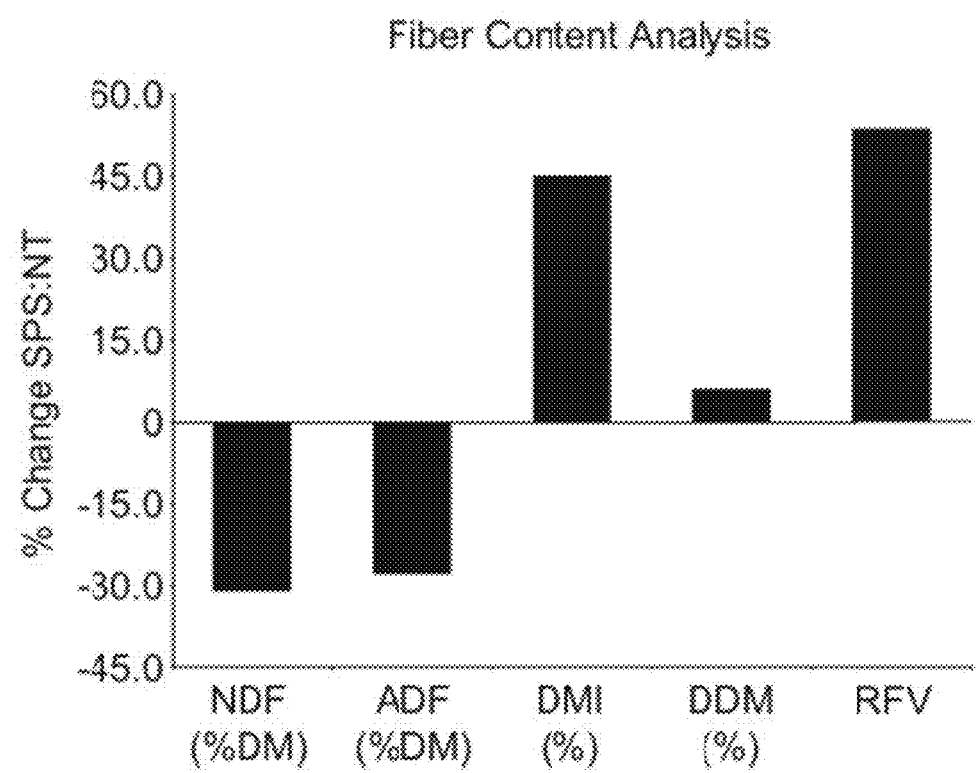
FIG. 19B shows fiber content analysis was done on the same tissue used in 19A. Acid detergent fiber (ADF) and neutral detergent fiber (NDF) were used to calculate digestible dry matter (DDM) and dry matter intake (DMI), respectively. RFV values are derived from DDM and DMI. Percent change for each parameter was determined using values in Table A.7.

Because the set of $NH_4NO_3$ fed plants shared similar characteristics with plants kept under symbiotic $N_2$ fixing conditions, this set of plants was also analyzed for any changes in forage quality as previously described. FIGS. 19A and 19B show the forage quality of non-transformed and 35S-mzSPS transformed alfalfa plants fed 5 mM $NH_4NO_3$. Alfalfa non-transformed and 35S-mzSPS transformed plants were cut back to the crown/base and allowed to grow for 40 days at which time shoots were harvested and lyophilized for analysis of forage quality. As shown in FIGS. 19A, 19B, and Table A.7 above, the percentage of CP and NPN was approximately 17 and 33 percent higher, respectively, in the transformed plants when compared to the NT plants. No substantial difference in the levels of SoIP was seen between the two sets of plants. While both ADIP and NDIP levels increased approximately 33 percent and 20 percent, respectively, in the transformed plants, the percent of degradable/digestible protein (nitrogen) bound to fiber was unchanged between the two sets of plants. Moreover, fiber content was approximately 30 percent lower in the ADF and NDF values which ultimately translated into a substantial increase, approximately 54 percent, in the RFV content of the $NH_4NO_3$ fed 35S-mzSPS transformed plants.

It would thus appear that the $NH_4NO_3$ fed 35S-mzSPS transformed plants behaved similarly as the transformants under $N_2$-fixing condition with regards to phenotype, forage quality, and stem and internode length. Furthermore, when comparing data between the two nitrogen conditions (Table A.7), both set of plants, non-transformed and 35S-mzSPS transformed plants, demonstrated improved forage quality when fed $NH_4NO_3$. While a more substantial increase in RFV content and decrease in degradable/digestible protein bound to fiber was seen in the 35S-mzSPS transformed plants, the NT plants showed a higher increase in the levels of CP and SoIP when fed $NH_4NO_3$. Both set of plants shared similar increases in NPN when comparing data from the two nitrogen conditions. It is important to note, the 35S-mzSPS transformed plants kept under symbiotic $N_2$ fixing conditions were higher in RFV content and shared similar to slightly higher values in protein content (CP, SoIP, NPN, and degradable/digestible protein bound to fiber) when compared to the non-transformed plants under fertilized conditions (Table A.7). Taken together, the data indicates that the 35S-mzSPS transformants, under symbiotic conditions, have equal to or better forage quality than alfalfa fertilized with synthetic nitrogen.

Figure 20:
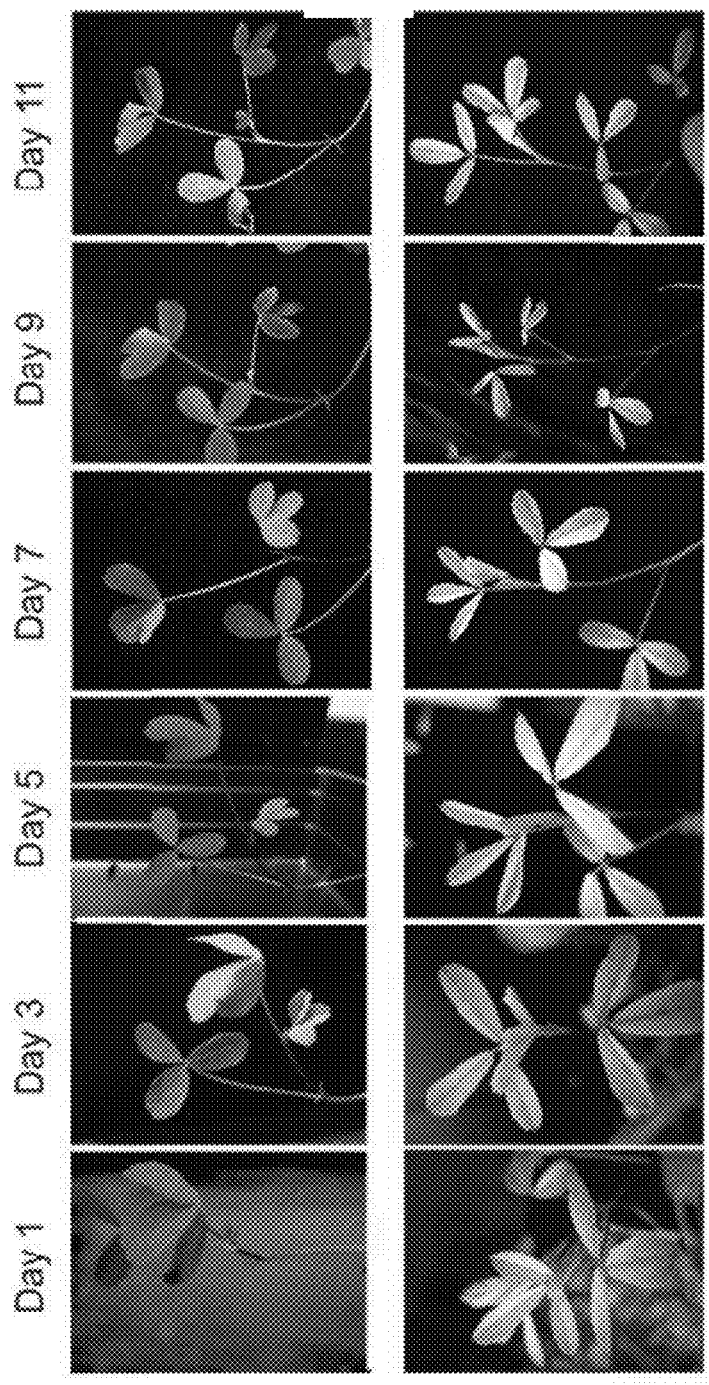
FIG. 20 shows the apical region with new emerging trifoliates of nontransformed and 35S-mzSPS transformed plants over a period of eleven days. A set of non-transformed and 35S-mzSPS transformed plants, transferred to a greenhouse, were immediately inoculated with *Rhizobia* and fed nitrogen free Hoaglands media (FIG. 2A). Pictures of the apical region were taken every two days to observe and compare the development and expansion of newly formed trifoliate in the 35S-mzSPS transformed plants and control plants. A representative sample of control and transformed plant is shown.

Several independent transformants with the 35S-mzSPS gene construct (#3, 6, 7, 12, 13, 14, 15, 17, 18) along with six non-transformed (1-6) plants were transferred to pots and placed under greenhouse conditions. These plants were immediately inoculated with S. meliloti and fed N free Hoagland's media to initiate the symbiotic relationship between the host and the bacteria. Following exposure to the bacteria, it takes about 3 weeks for $N_2$-fixation to begin and the plants go through nitrogen stress during this period. Interestingly, the transformed plants exhibited a phenotype not previously seen with the other sets of transformants which were first established by growing them with nitrogen. The newly emerged leaves in the shoot apical meristems of all the transformed plants were completely white and showed no signs of pigmentation (FIG. 20 and A.3). Growth of the shoot apical meristems was monitored for about 11 days to observe the development and expansion of newly emerged trifoliate in the transformed plants. Pictures taken every two days of the shoot apical meristems of NT (#4) and 35S-mzSPS transformant (#12) are shown in FIG. 20 and represents what was seen in each class of plants. All the plants exhibited normal emergence and expansion of the new trifoliates. However, the trifoliates were green from the start of emergence in the NT plants. The pigmentation in the newly emerged trifoliate in the 35S-mzSPS transformed plants, began to slowly appear near the apex of each leaflet only upon completion of trifoliate expansion. Even then, 100% of the leaflets were not green, an effect seen as far down as the third or fourth fully expanded trifoliate from the shoot apex (FIG. 20).

The major difference between the two sets of plants is the higher level of sucrose and its derivatives in the transformants under conditions of N deficiency compared to the control plants and this phenotype could be an attribute of this imbalance in C and N metabolites. To monitor the status of the C metabolic pathways, the plant apices of control plants and the transformants were stained for starch.

While the control plants showed staining for starch in the young emerging trifoliates, the same leaves in the transformed plants were not stained indicating the absence of starch synthesis, indicating that the extreme chlorosis seen in the apices of the transformants is due to the huge imbalance between sucrose and N, which affects the induction of many of the photosynthetic genes including those involved in the synthesis of the pigments and starch.

Figure 21A:
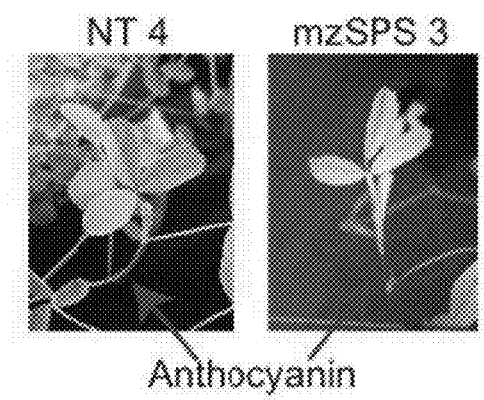
FIG. 21A shows stems of non-transformed and 35S-mzSPS transformed plants were bright red in color and indicated an accumulation of Anthocyanin in these tissues. Blue arrows point to the stems of representative plants.
Figure 21B:
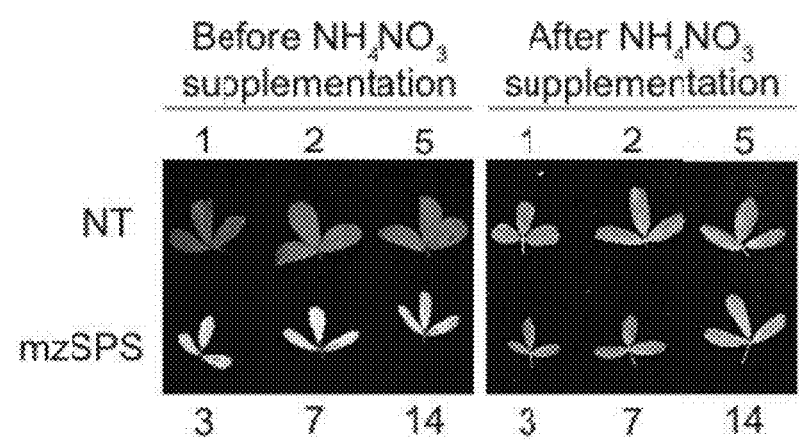
FIG. 21B shows the set of non-transformed and 35S-mzSPS transformed plants before and after $NH_4NO_3$ supplementation. Images were taken from trifoliates of representative plants (NT: 1, 2, and 4; SPS: 3, 7 and 14) before $NH_4NO_3$ supplementation and 29 days after $NH_4NO_3$ supplementation.
Figure 22:
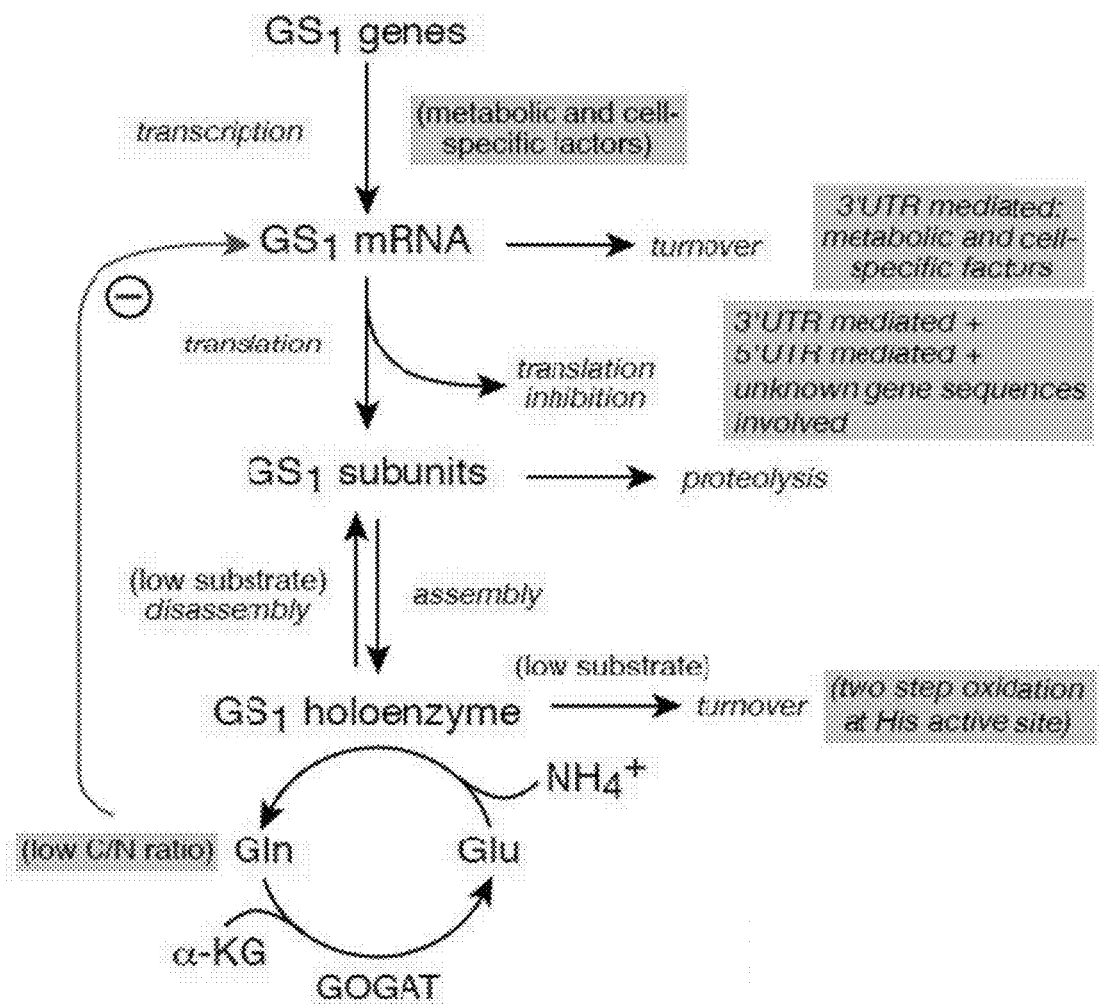
FIG. 22 shows a multistep regulation of Glutamine Synthetase.

To check if N deficiency was indeed the basis for chlorosis in the emerging leaflets, the transformants were supplemented with about 5 mM $NH_4NO_3$. FIGS. 21A and 21B show the accumulation of anthocyanin in the stems of all plants and the recovery of pigmentation in the leaves of the transformed plants supplemented with about 5 mM $NH_4NO_3$. The pigmentation in most of the leaves of the 35S-mzSPS transformed plants was restored within approximately 20 days. The NT plants, when treated with about 5 mM $NH_4NO_3$ showed a more intense green color, likely because the leaves were already green to start with.

The complete N profile and fiber analysis of the above ground tissues of the two classes of alfalfa plants grown under the two different N conditions demonstrated that forage quality was enhanced in the shoots of the 35S-mzSPS alfalfa transformants (FIGS. 17A-B and 19A-B; Table A.7). The level of fiber, measured as ADF and NDF content, was substantially lower in shoots of the transformants, which corresponded to about 5-6% increase in digestible dry matter and up to about 45% increase in dry matter intake, respectively. Moreover, levels of protein, particularly CP, were substantially higher in the transformants. It is important to note that the leaves of alfalfa are more digestible and higher in nutrient and CP content than the stems. While the leaves showed only a slight decline in digestibility as the plant matured, levels of CP declined continuously from the vegetative to the early seed stage. Several key characteristics exhibited by the alfalfa 35S-mzSPS transformants seemingly influenced the above forage tests such as delayed flowering time/development, increased leaf chlorophyll and N content, and decreased stem internode length (FIGS. 18, 20, 21A-B, and 22). The increase in soluble sugars resulting from increased sucrose biosynthetic capabilities of the transformants also has a role in the improvement of forage quality. The developmental stage of the plant is an important factor to influence forage quality. The tissue of plants in this example were harvested before the plants entered the bud/bloom stage. However, the NT plants were still ahead developmentally when compared to the 35-mzSPS transformants. Moreover, the 35S-mzSPS alfalfa transformants under symbiotic conditions exhibited higher N protein profile and a higher potential digestible dry matter intake (RFV) value when compared to the NT plants kept under non-symbiotic, fertilized, conditions (Table A.7). These findings show that the 35S-mzSPS transformants perform better than the NT plants, particularly under greenhouse conditions.

Increasing SPS activity leads to increased sucrose synthesis and increases the leaf to stem ratio, photosynthetic rates, nodulation and nitrogen fixation, elemental N, chlorophyll and protein content. The flowering time is delayed implying a prolonged vegetative state. However, a positive attribute of increasing SPS activity is the improvement in forage quality. A major focus for forage breeding and biotech programs includes improving forage digestibility. A 10% increase in cell-wall/fiber digestibility of forages has been estimated to increase production of milk and beef production by 350 million dollars/yr, as well as decrease manure production by 2.8 MM tons/yr and decrease grain supplements by 2 million tons/yr. Forage legumes have provided a critical component of feed for livestock in the meat and dairy industries for centuries. In fact, the dairy industry in New Mexico relies heavily on alfalfa, the number one cash crop in the state, due to a combination of several factors, such as its high nutritional quality and yield production. Animal performance in the above industries depends in part on the nutritional value or forage quality of the dry matter the livestock consumes.

Example 2

Figure 31:
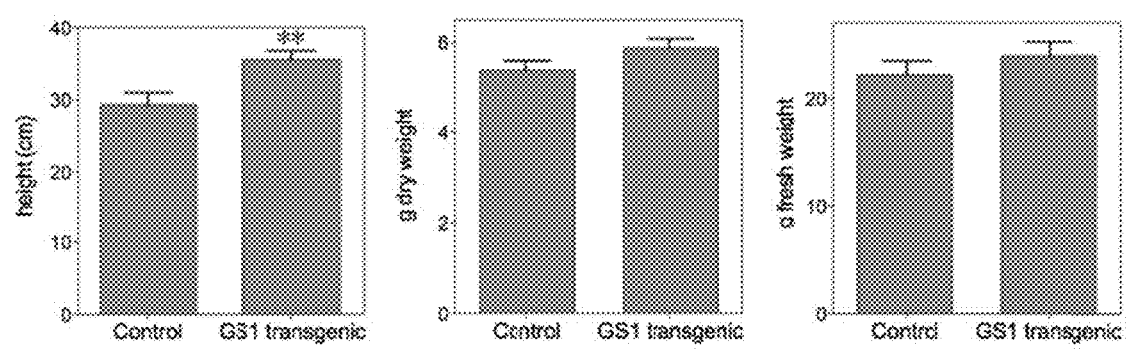
FIG. 31 shows differences in shoot height and biomass accumulation between transgenic and non-transformed alfalfa plants.

Referring to FIGS. 29A, 29B, 30 and 31, transgenic alfalfa plants transformed with the glutamine synthetase Gmgln$\beta$1 showed improved growth, elongated stem, increased protein and enhanced nitrogen use efficiency. In FIG. 31, alfalfa shoot height was measured, shoots were cut and fresh weight determined after five weeks of growth. Fresh tissues were dried out at about 37° C. and dry weight were measured. Asterisks indicate that the differences are statistically significant.

Example 3

An embodiment of the present invention was used to determine:
  i. if the 3'UTR mediated posttranscriptional regulation of GS1 is a universal phenomenon.
  ii. if the 5' and/or 3'UTR of the Gmgln$\beta$1 gene play a role in translational regulation.
  iii. if the posttranscriptional regulatory step is mediated by a protein factor or miRNA.
  iv. the biochemical signal(s) that stabilizes/destabilizes the transcript and/or translation repression.

To check if translation enhancement by the Gmgln$\beta$1 5'UTR was due to its interaction with some factor that is only present in the plant cells, in vitro reticulocyte and wheat germ translation systems were used to check for translational regulation of the Gmgln$\beta$1 transcript with or without its 3' and 5'UTRs.

Figure 32A:
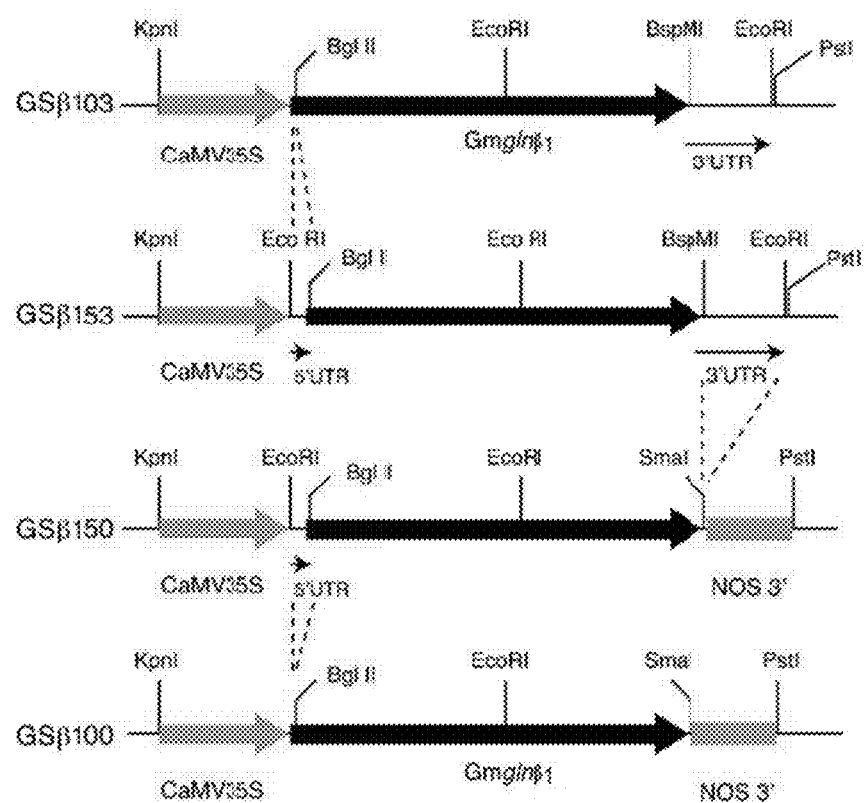
FIG. 32A shows gene constructs comprising the soybean Gmglnβ1 cDNA driven by the CaMV 35S promoter, either containing or lacking its 5'UTR and/or its 3'UTR.

Referring to FIG. 32A, pGS$\beta$103, is a gene construct without the 5'UTR but with the 3'UTR, pGS$\beta$153, has both 5' and 3'UTRs, pGS$\beta$150 has the 5'UTR but not the 3'UTR, and pGS$\beta$100 lacks both the 5' and 3'UTRs. The gln$\beta_1$ 5'UTR was replaced by the mRNA leader of the CAMBIA CaMV 35S promoter and the 3'UTR was replaced by the NOS terminator. The isolation of the Gmgln$\beta$1 gene (NCBI accession number AF301590) was previously described. Four different GS$\beta$1 gene constructs with and without its 5' and 3'UTRs were made. The Gmgln$\beta$1 gene constructs either included its own 5'UTR (GS$\beta$150, GS$\beta$153), its own 3'UTR (GS$\beta$103, GS153), or lacked both its 5' and 3'UTR (GS$\beta$100). In GS$\beta$150 and GS$\beta$100, the 3'UTR was replaced with the NOS 3'UTR and in pGS$\beta$103 and GS$\beta$100, the 5' UTR was replaced with the mRNA leader of the CaMV35S promoter::uidA gene construct in the CAMBIA 2301 plasmid (CAMBIA, Canberra, Australia). To make the gene constructs with the Gmgln$\beta$1 5'UTR, the CaMV35S promoter was amplified, using pCAMBIA2301 plasmid as a template, with reverse primers with an EcoRI site downstream of the CaMV35S transcription start site (5'-GAG AAT TCC CGT GTT CTC TCC AAA TGA AAT GAA CTT C-3') (SEQ ID. NO. 6). The CaMV35S promoter for the Gmglnβ1 gene constructs without the 5'UTR was amplified with a reverse primer that included extra nucleotides encoding the first seven amino acids of the Gmglnβ1 gene, down to a BglII site (5'-AGA TCT GAG AGC GA GAC ATG GTC AAG AGT CCC CCG TGT T-3') (SEQ ID. NO. 7), which was used to clone the remaining of the Gmglnβ1 gene (FIG. 32B). The forward primer for amplification of the CaMV35S promoter included a HindIII at the 5' end (5'-AAG CTT CAT GGA GTC AAA GAT TC-3') (SEQ ID. NO. 8). The Gmglnβ1 gene constructs without its 3'UTR (GSβ150 and GSβ100) were made by removing the Gmglnβ1 3'UTR and replacing it with a SmaI/PstI NOS 3'UTR fragment amplified from the pMON316 vector (forward primer: 5'-CCC GGG ATC GTT CAA ACA TTT GGC AAT AAA GTT-3' (SEQ ID. NO. 9); reverse primer: 5'-GAG CTC TGC AGC CCG ATC TAG TAA CAT AGA CAC C-3') (SEQ ID. NO. 10). For the β-glucuronidase gene construct GUSA50, the CaMV35S promoter comprising the Gmglnβ1 5'UTR was amplified from the GSβ153 gene construct by PCR using a primer comprising a NcoI site at the translation start site (FIGS. 35A-C, reverse primer: 5'-CCA TGG CTC CAA AAT CAA GCA AAG ACC CTT CTT T-3') (SEQ ID. NO. 11), which was then ligated to the uidA gene excised from the CAMBIA 2301 plasmid as a NcoI/BstEII fragment. A BstEII/PstI NOS 3'UTR fragment was amplified by PCR from the CAMBIA 2301 (forward primer: 5'-GGT GAC CAG CTC GAA TTT CCC CGA TCG TTC AAA CAT TTG GC-3') SEQ ID. NO. 12) and a NOS SacI/PstI reverse primer (as above) and placed at the end of the uidA gene. All PCR products were cloned into the pGEM-T easy vector and sequenced. Gene elements were assembled in the pBluescript II KS (-) plasmid. The constructs were sequenced and subsequently cloned in the pCAMBIA 2300 vector as KpnI/PstI inserts and transformed into *A. tumefaciens* strain GV3101 for plant infiltration.

Figure 23A:
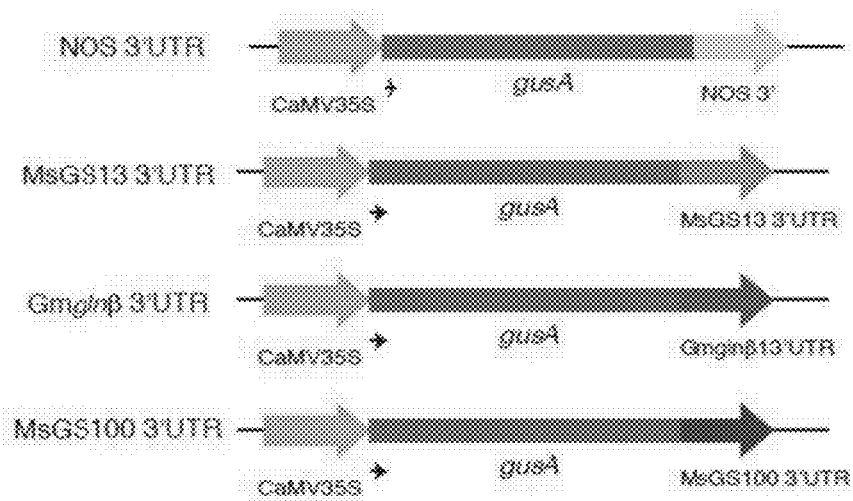
FIG. 23A shows constructs that were introduced into alfalfa by *A. tumefaciens* mediated transformation.
Figure 23B:
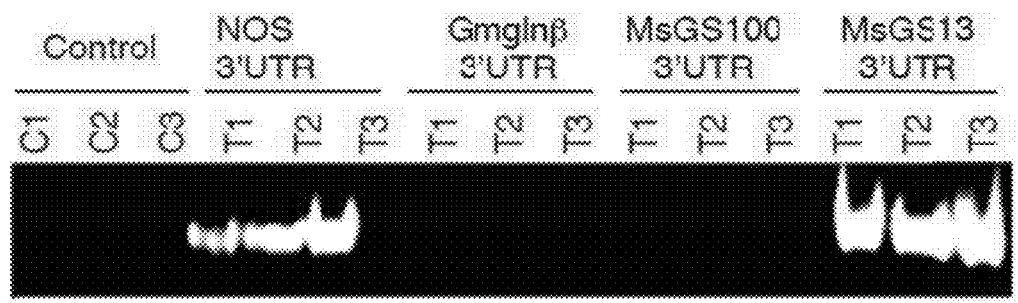
FIG. 23B shows results of protein extracts from the leaves of three independent transformants for each construct that were subjected to native gel electrophoresis followed by in-gel GUS staining using a flurogenic substrate.

FIGS. 23A and 23B show a GUS coding region engineered behind a CaMV 35S promoter, followed by different 3'UTRs—3' UTR of Gmglnβ1 (soy), 3'UTR of MsGS100 (GS100), 3' UTR of MsGS13 (GS13), and the NOS terminator (NOS). The 3'UTR of MsGS100, like that of the Gmglnβ1 gene plays a role in transcript turnover. The 3'UTR of MsGS13, however, has a stabilizing effect on the transcript compared to the NOS 3'UTR. The two alfalfa GS1 genes exhibited differential posttranscriptional regulation mediated by their 3'UTRs. Thus, the 3'UTR mediated transcript turnover was concluded to not be a universal phenomenon for all GS1 genes.

Figure 24A:
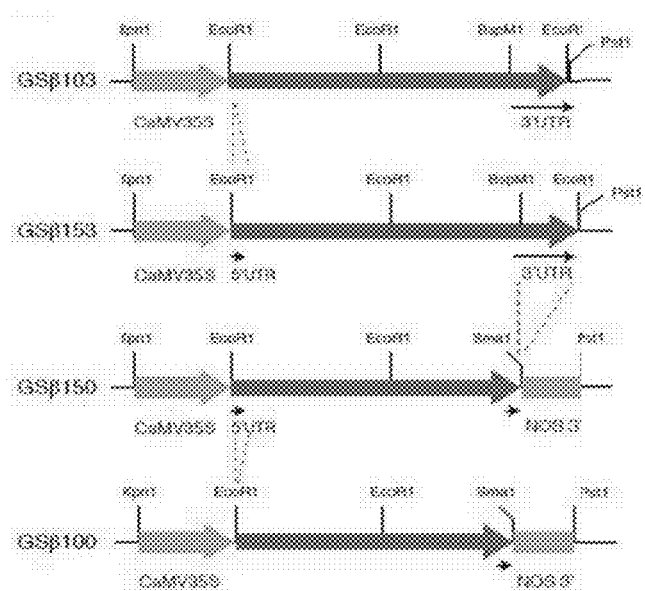
FIG. 24A shows a Gmglnβ1 gene that was engineered behind a CaMV 35S promoter with and/or without its 3'UTR and/or 5'UTR. The 3'UTR in the GSβ100 and GSβ150 constructs was replaced with a NOS terminator.
Figure 24B:
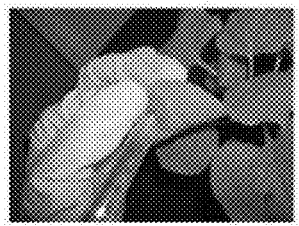
FIG. 24B shows constructs introduced into *A. tumefaciens* strain GV3101. The engineered *A. tumefaciens* were then used for Agroinfiltration into tobacco leaves.
Figure 24C:
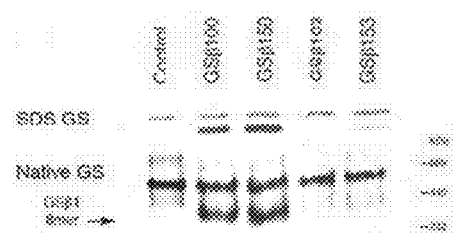
FIG. 24C shows RNA that was isolated from the infiltrated tissues and subjected to northern blot analysis using the Gmglnβ1 coding region, Gmglnβ1 3'UTR, NOS 3'UTR and the NPTII gene as probes.
Figure 24D:
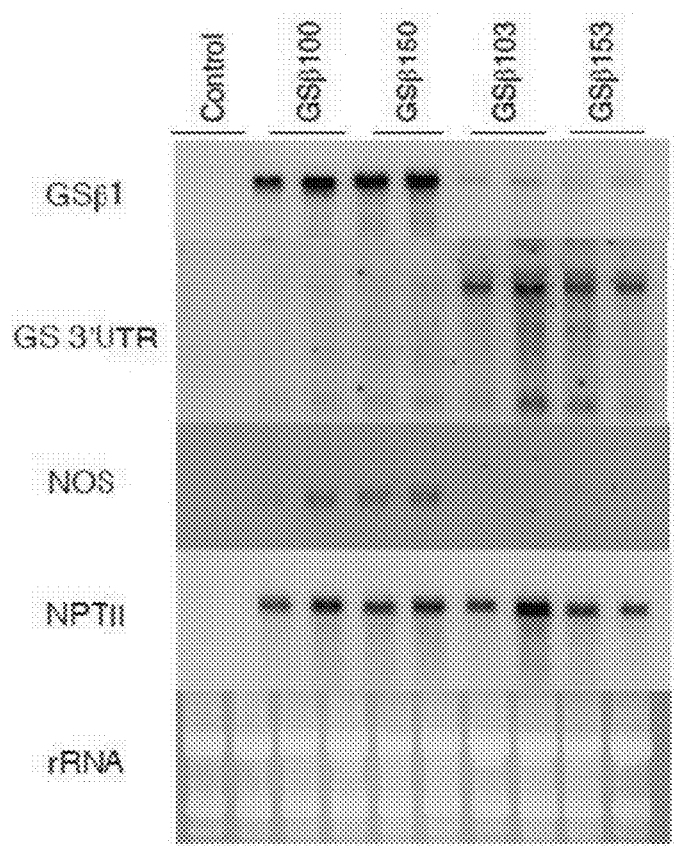
FIG. 24D shows transcript analysis of *Agrobacterium*-infiltrated tobacco leaf samples. For each experiment two independent plants for each construct were sampled, total RNA was isolated from 3 individual leaves from each independent plant 4 days after agroinfiltration with *A. tumefaciens* containing gene constructs of the Gmglnβ1 gene with and without its 5' and 3'UTRs. Twenty micrograms of each sample were then fractionated by electrophoresis and subjected to northern blot hybridization. The blots were sequentially hybridized with $^{32}P$ labeled probes corresponding to the coding region and the 3'UTR of the Gmglnβ1 gene, the *Agrobacterium* nopaline synthetase terminator (NOS 3'UTR) and the kanamycin resistance (NPTII) gene. The 28S rRNA stained by SYBR Gold is also shown as a control for loading.

Referring to FIG. 24A-C, the tissues infiltrated with the GSβ100 and GSβ150 constructs showed higher accumulation of GS1 polypeptide and a novel GS holoprotein. The tissues with the GSβ150 construct showed higher accumulation of the GS1 polypeptide and the novel holoprotein compared to tissues infiltrated with the GSβ100 construct. Tissues with GSβ153 showed a higher level of GS1 polypeptide compared to tissues infiltrated with the GSβ103 construct. The 3'UTR of Gmglnβ1 functions independent of the 5'UTR to destabilize the transcript. While the 3'UTR of Gmglnβ1 gene plays a role in transcript turnover, the 5'UTR functions as a translation enhancer.

Figure 25A:
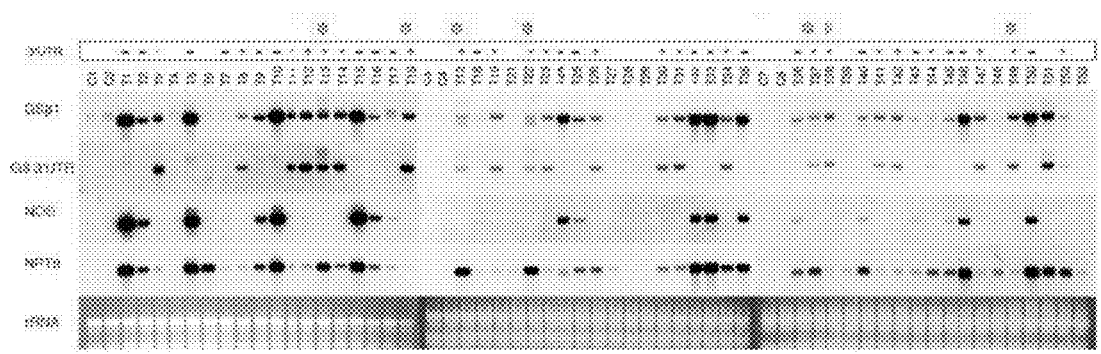
FIG. 25A shows RNA from 53 independent randomly selected transformants with either the GSβ153 construct or the GSβ150 construct subjected to northern blot analysis using the Gmglnβ1 coding region, Gmglnβ1 3'UTR, NOS 3'UTR and the NPTII gene as probes. The GSβ153 (+) and GSβ150 (−) transformants were identified based on whether the blot hybridized to the Gmglnβ1 3'UTR (+) or the NOS probes (−), respectively.

Referring to FIG. 25A, differences in the intensity level with the NPTII probe in the different transformants reflects position effect due to random insertion of the T-DNA in the genome of the transformant. Note: transformants T13, T22, T37 (*) showed higher NPTII transcript level and relatively lower level of Gmglnβ1 transcript and transformants T19, T38, T49 (*) showed higher level of Gmglnβ1 transcript relative to the NPTII transcript. Transformants T13, T22, T37 besides exhibiting extreme silencing of the transgene, also showed additional hybridizing bands with the Gmglnβ1 and Gmglnβ1 3'UTR as probes, and can be used for understanding the mechanism of transcript turnover.

Figure 25B:
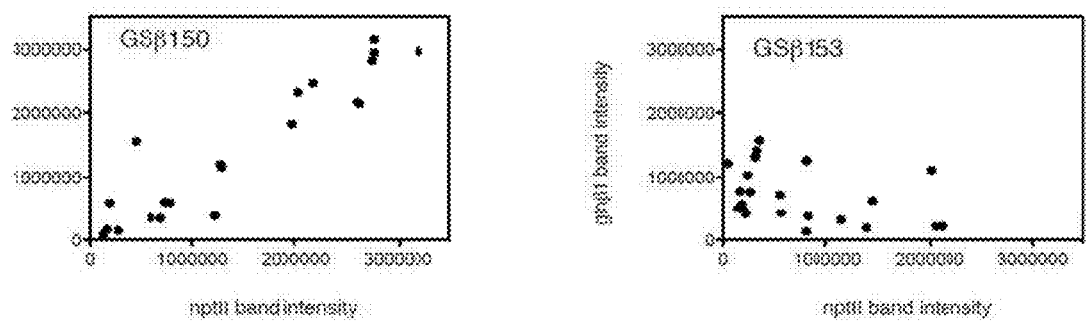
FIG. 25B shows the hybridization bands in FIG. 25A were scanned and quantified and the band intensity for hybridization with NPTII and the Gmglnβ1 probes was plotted.

Referring to FIG. 25B, a direct correlation between the hybridization signal with the NPTII probe and the Gmglnβ1 probe was observed in the GSβ150 transformants suggesting transcriptional regulation of the transgene. No direct correlation between the hybridization signal with the NPTII probe and the Gmglnβ1 probe was observed in the GSβ153 transformants. Gmglnβ1 transcript level is regulated by its 3'UTR at the level of transcript stability. RNA processing involves the formation of intermediates.

Figure 26A:
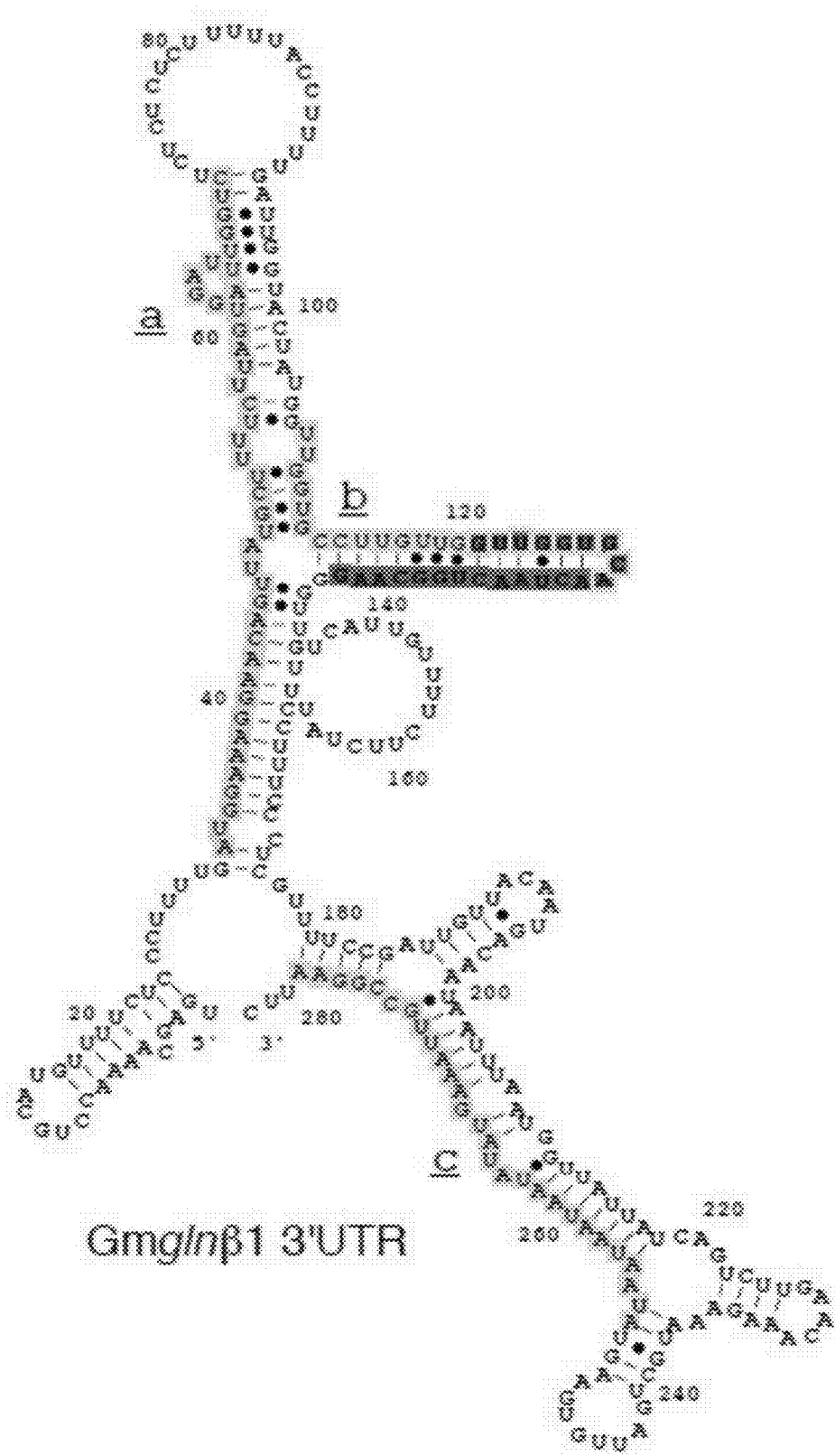
FIG. 26A shows the predicted secondary structure of the 3'UTR of Gmglnβ1 transcript. The secondary structure was predicted using the MFOLD Program. The colored regions indicate the position of conserved AU-rich regions. These sequences in the Amy3 3'UTR are located in domains I and III, which confer sugar-dependent regulation.
Figure 26B:
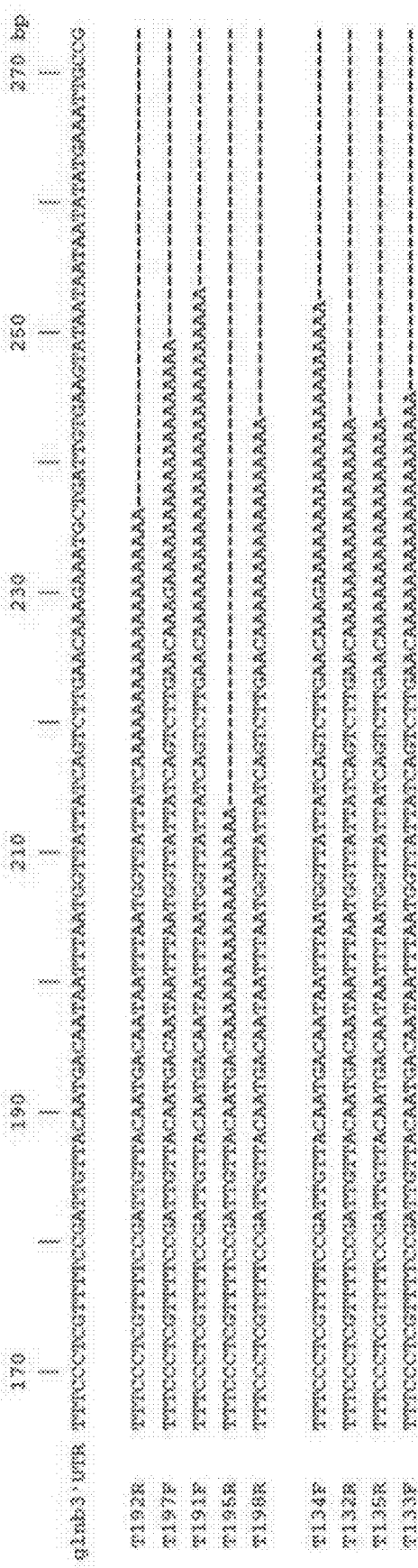
FIG. 26B shows RNA isolated from transformant T13 (exhibiting gene silencing) and transformant T19 (with levels of Gmglnβ1 transcript comparable to NPTII transcript level) was reverse transcribed followed by PCR amplification using oligo(dT) and a gene specific region as primers. The amplified fragments were cloned and sequenced.

Referring to FIGS. 26A and 26B, analysis of multiple clones from each set of alfalfa transformants showed that while RNA from T13 transformant used the same polyadenylation site at position 226 past the stop codon, the RNA from T19 transformant used multiple polyadenylation sites, at positions 194, 216 and 226 past the stop codon. 3' processing of the transcript may have a role in transcript instability. Only regions a and b were maintained in the mature transcript following polyadenylation and thus may be target regions for transcript turnover.

Figure 27A:
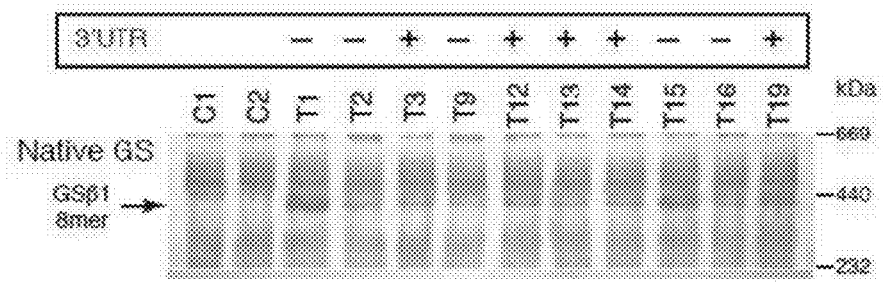
FIG. 27A shows the RNA blot that was hybridized to the Gmglnβ1 coding region, the Gmglnβ1 3'UTR or the NOS probe.
Figure 27B:
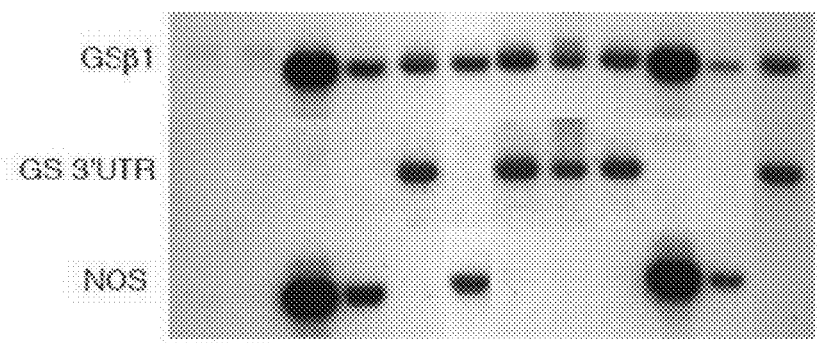
FIG. 27B shows the protein extracts from the same transformants as used for RNA analysis were subjected to native gel electrophoresis followed by immunoblot analysis using GS1 antibodies. While the blots showed many immunoreactive bands in all the lanes, a unique band was detected only in the transformants. This band corresponds with the GS31 holoprotein.
Figure 27C:
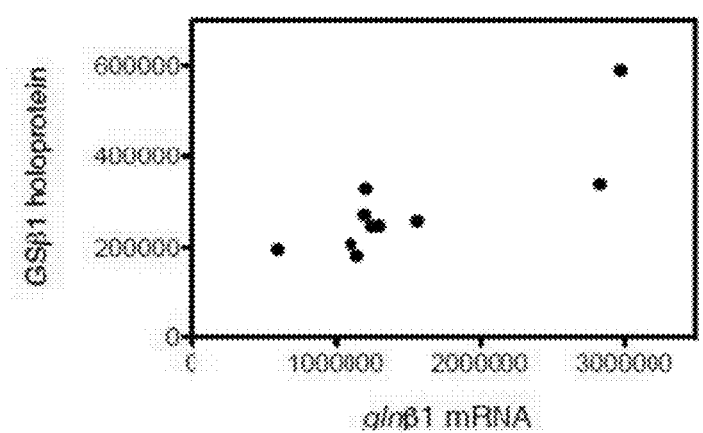
FIG. 27C shows the intensity of the hybridization signal with the Gmglnβ1 coding region probe and the band intensity for the immunoreactive band corresponding to the transgene protein.

FIGS. 27A-C show leaf RNA and protein from GSβ150 and GSβ153 transformants with equal level of NPTII transcript level. They were subjected to northern blot analysis and native gel electrophoresis followed by western blot analysis, respectively. There is a direct correlation between the glnβ1 mRNA and GSβ1 holoprotein irrespective of whether the transformant is GSβ153 or GSβ150. A direct correlation between transcript level and the corresponding protein irrespective of whether the transcript has or does not have its 3'UTR indicate that the Gmglnβ1 3'UTR does not cause repression of translation.

Figure 28A:
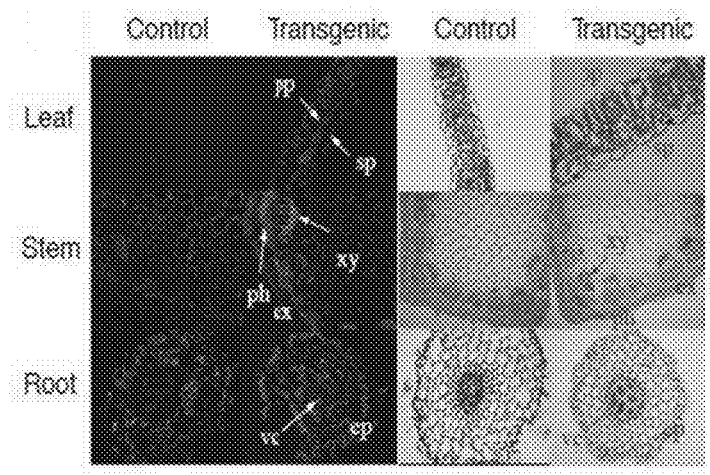
FIG. 28A shows the site of Gmglnβ1 expression in tissues of GS1β50 alfalfa transformants and the immunolocalization of GS in control and GS1β50 alfalfa transformants. Cross sections of leaves, stem and roots from a non-transformed (control) and the GS1β50 alfalfa transformants (GS) were stained with the GS1 antibodies in combination with a fluorescent antibody. Abbreviations: cx cortex, en endodermis, ep epidermis, pc pericycle, ph phloem, pp palisade parenchyma, sp spongy parenchyma, vc vascular cylinder, xy xylem.
Figure 28B:
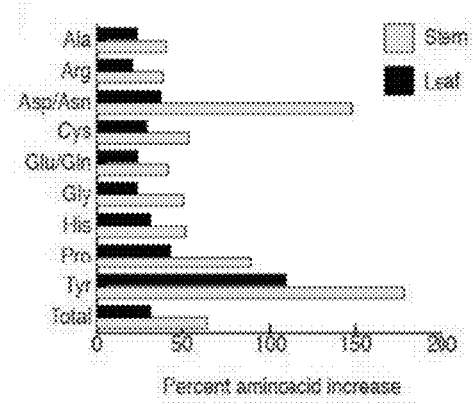
FIG. 28B shows an increase in total amino acid concentration in alfalfa tissues from transgenic plants compared to the concentration in control non-transformed plants.
Figure 28C:
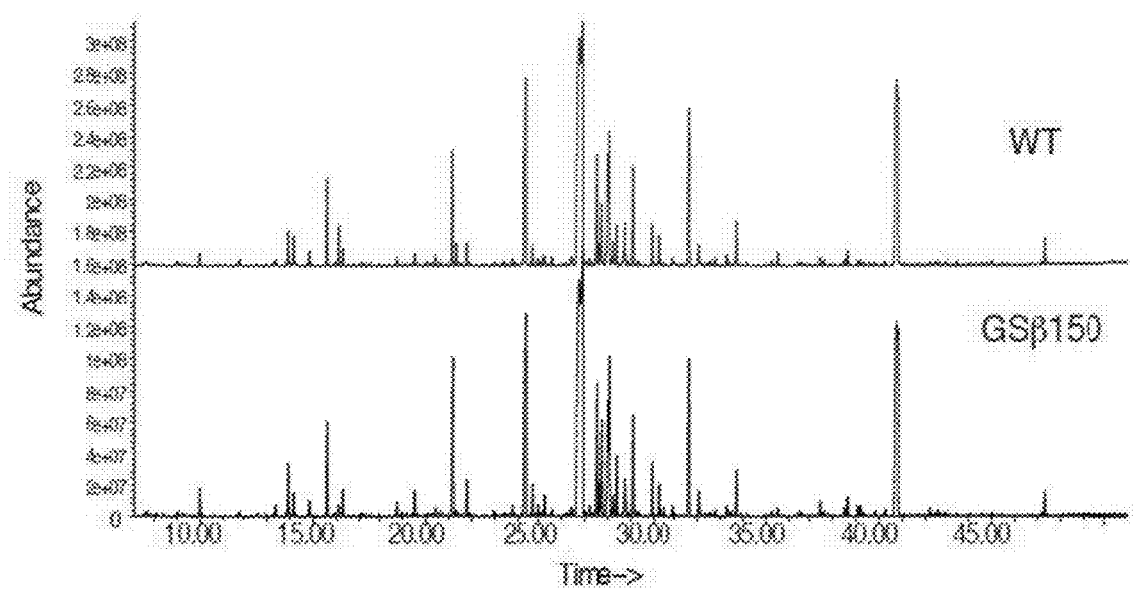
FIG. 28C shows GC-MS total ion chromatograms of leaf extracts from transgenic and wild type alfalfa. The following metabolites with a significant change in accumulation versus wild type plants were identified: Sucrose (28), Inositol (19), Myo Inositol (11), Asparagine (11), Gluconic Acid (10), 2-ketogluconic Acid (10), 2-propenoic Acid (8), Galactose (7), Valine (6), Gluconic Acid (6), Glucose (6), Citric Acid (6), Glutamine (6), Ribonic Acid (6), Fructose (5), Xylitol (3), Proline (3), Benzoic Acid (3), Cystathionine (2), Alanine (2), Cysteine (2).
Figure 29A:
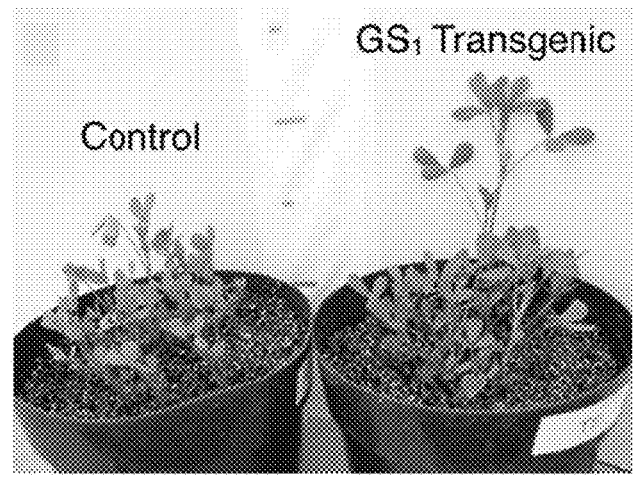
FIG. 29A shows phenotypic differences between control non-transformed and transgenic alfalfa plants transformed with glutamine synthetase Gmglnβ1 gene at two weeks of growth after cutting off the shoots.
Figure 29B:
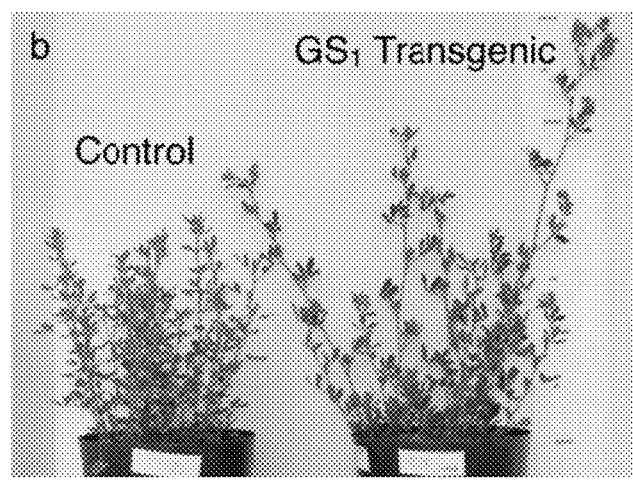
FIG. 29B shows phenotypic differences between control non-transformed and transgenic alfalfa plants transformed with glutamine synthetase Gmglnβ1 gene at five weeks of growth after cutting off the shoots.
Figure 30:
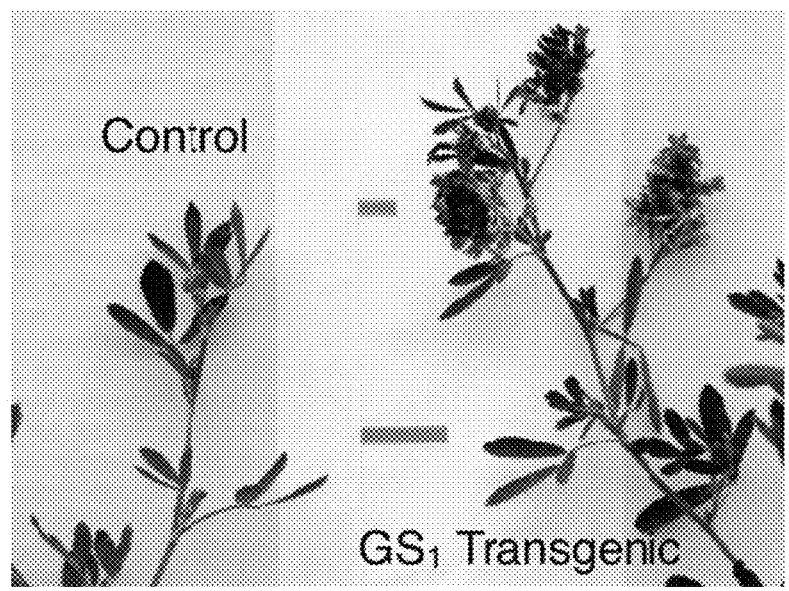
FIG. 30 shows differences in flowering between control non-transformed and GS1 alfalfa transgenic plants at five weeks of growth after cutting off the shoots.

Referring to FIGS. 28A-C, compared to control plants, the transformants showed major immunostaining in the vasculature of the leaves, stem and roots. Alfalfa transgenic plants showed higher amino acid concentration and higher accumulation of asparagine and proline. The higher accumulation of the amino acids in the stem over leaves of the transformants is an attribute of the vasculature enhanced expression of the CaMV 35S promoter. Increased GS activity is associated with changes in amino acid pools and other metabolites.

*Agrobacterium tumefaciens* strain GV3101 (Rif r) was used for tobacco infiltration experiments. Tobacco plants (*Nicotiana tabaccum* var. *Xanthi*) were propagated from cuttings of tops of plants grown under sterile conditions in magenta boxes containing solid Murashige and Skoog media supplemented with about 1% Sucrose. New tops were cut and transferred to new media every three weeks. Plant tops with developed roots were moved to pots with sterile vermiculite and grown for 3 weeks at a 16 h light/8 h dark cycle under fluorescent light before infiltration with *Agrobacterium*. Plants were maintained with Hoagland's nutrient solution containing about 5 mM $NH_4NO_3$.

Infiltration of *N. tabaccum Xanthi* leaves was done as a modification of a previous method. Single colonies of *A. tumefaciens* comprising the different gene constructs were grown overnight in LB media with Kanamycin and Rifampicin selection (about 50 μg/ml each). Cultures were diluted 10 fold in LB media and grown with antibiotic selection to a 0.5 OD600. Cells were centrifuged and resuspended in the same volume of induction media (about 10 mM MES, about 10 mM $MgCl_2$, about 0.2 mM acetosyringone, about pH 5.7)

and incubated overnight at 30° C. with shaking. *Agrobacterium* cells were then centrifuged and resuspended in the same volume of infiltration media (about 1 mM MES, about 0.5 mM $MgCl_2$, about 0.02 mM acetosyringone, about pH 5.7). The three youngest leaves of each tobacco plant were uniformly infiltrated with the *Agrobacterium* suspension (two plants per gene construct) using about 1 ml disposable syringe without a needle. Four days after infiltration, the middle vein of the leaf was removed and the leaf blades were used for protein extraction or harvested in liquid nitrogen and frozen at about −80° C. for RNA isolation.

RNA was isolated from leaf tissues by phenol/chloroform extraction and LiCl precipitation as previously described. Total leaf RNA was subjected to 1.5% (w/v) formaldehyde-agarose gel electrophoresis followed by northern blotting using 32P-labeled DNA probes. The same blot was hybridized to the different probes following stripping before hybridizing with the next probe.

RNA secondary structure of the Gmglnβ1 5'UTR was predicted with the RNA folding by free energy minimization software MFOLD 2.0 and with the Unified Nucleic Acid Folding software UNAFold 3.8 with similar results.

Fresh leaf tissue was ground in a mortar with about 2 volumes of extraction buffer (e.g., 25 mM Tris, 20% glycerol, 5% ethylene glycol, 1 mM $MgCl_2$, 1 mM EDTA, 0.1% Triton X100, 5 mM DTT, 3% insoluble PVPP, pH 8). *E. coli* proteins were extracted in the same buffer without PVPP or Triton X100 and sonicated for five cycles of about 10 sec each. Plant and bacterial extracts were clarified by centrifugation at about 20,000×g for about 15 min at about 4° C. and transferred to new tubes. Protein concentration was determined colorimetrically with a protein assay solution (Biorad, Hercules, Calif.). Protein extracts were fractionated by non-denaturing or SDS polyacrylamide gel electrophoresis as described, followed by blotting to PVDF transfer membranes (Millipore, Billerica, Mass.). Proteins were immunodetected with antibodies raised against soybean GS1 or with commercially available anti-β-glucuronidase (GUS) antibody (ABCAM, Cambridge, Mass.) and anti-glutathione transferase (GST) antibody (GE Healthcare, Piscataway, N.J.) and a secondary antibody coupled to Alkaline Phosphatase. GS immunoreacting bands were quantified using Carestream Molecular Imaging Software 5.0 (Carestream Health, Rochester, N.Y.). A statistical analysis of the GS band intensities was performed (unpaired t test) using the Prism 5.0 software (GraphPad Software).

β-glucuronidase activity in extracts of infiltrated tobacco plants was determined using the fluorogenic substrate 4-methyl umbelliferyl glucuronide (4-MUG, Gold Biotechnology, Saint Louis, Mo.). Leaf extracts were incubated in a 1 mL reaction containing about 1 mM 4-MUG at 37° C. Aliquots (about 200 µL) were removed at about 10 min or about 30 min intervals, the reaction was stopped by adding about 1.8 mL of 0.2 M $Na_2CO_3$ and the fluorescence of 4-methyl umbelliferone (4-MU) produced was measured in a fluorometer (Turner Designs, Sunnyvale, Calif.) with an excitation wavelength at 365 nm, emission filter at 455 nm. GUS specific activity was calculated against a 4-MU standard curve (from about 0.1 to 5 µM).

Total RNA isolated from tobacco leaves infiltrated with the different GS1 gene constructs was reverse transcribed (RD with an oligo-dT containing an anchor primer (5'-CCA GTG AGC AGA GTG ACG AGG AAG CTT(17)-3') (SEQ ID. NO. 13). GS1 PCR products were further amplified from the cDNA with a forward primer for the GS1 5'UTR (5'-CAC GGG AAT TCT CTA AAA GAG ATC TT-3' (SEQ ID. NO. 14) for constructs GSβ150 and GSβ153), or with a forward primer for the CaMV35S mRNA leader (5'-AAC ACG GGG GAC TCT TGA CCA T-3' (SEQ ID. NO. 15) for constructs GSβ100 and GSβ103), and a reverse primer corresponding to the anchor sequence, which contained a Hind III site at the end to preserve a continuous polyA tail. GS1 PCR products were cloned in pCRBlunt II and sequenced. RNA was in vitro transcribed from the RT-GSβ1 clones with a T7 RNA synthesis kit and purified. Equal amounts of capped and polyadenylated RNA were translated in vitro in a wheat germ system and the products were analyzed by western blotting using GS1 antibodies as described in a previous section.

The plasmid pKSglnβ153 contains a full length soybean cytosolic glutamine synthetase cDNA (Gmglnβ1) as an EcoRI fragment cloned in the sense orientation with respect to the P lac promoter (FIG. 38a) of the pBluescript II KS (−) phagemid, whereas the plasmid pKSglnβ135 has the Gmglnβ1 cDNA insert in the antisense orientation. The plasmid pGEX::glnβ1 has the full length Gmglnβ1 cDNA in the glutathione transferase expression plasmid pGEX-4T-2 and was created by inserting the Gmglnβ1 cDNA as a transcriptional fusion in the Eco RI fragment at the end of the GST gene. The 5'UTR of the Gmglnβ1 gene introduces a stop codon producing a GST protein in which the last nine amino acids were replaced by a leucine (see, FIG. 38B). The GS plasmids were transformed into *E. coli* XL1 Blue cells. Ten mL bacterial cultures were grown to an exponential phase. Expression of the Gmglnβ1 gene from the P lac in the pBluescript II KS or the P tac promoter in the pGEX-4T-2 plasmids was induced by incubating with 5 mM IPTG for about two hours. Cells were harvested by centrifugation at about 5,000×g for 5 minutes at about 4° C. Cell pellets were resuspended in about 1 mL of extraction buffer, protein was extracted and analyzed by Western blotting as described in the previous sections.

Figure 33A:
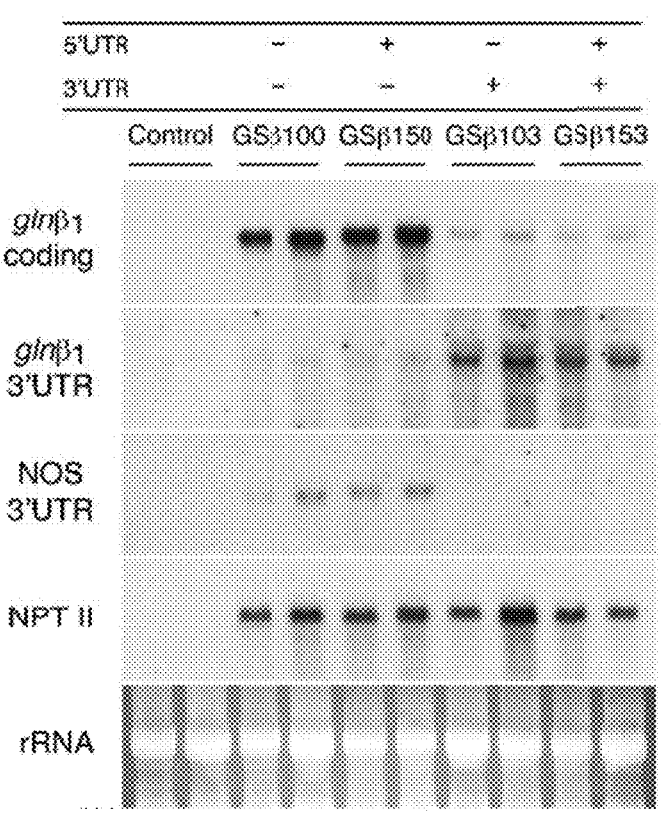
FIG. 33A shows the transcript analysis of agroinfiltrated leaf samples.
Figure 33B:
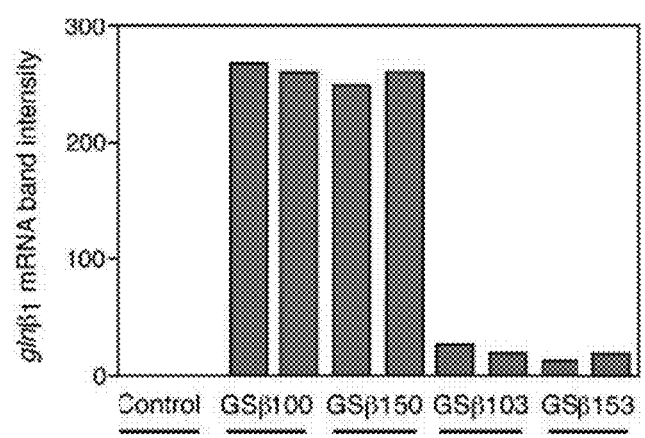
FIG. 33B shows that the hybridizing bands corresponding to the Gmglnβ$_1$ coding region and NPTII were quantified and standardized against the NPTII quantified bands and plotted. Two independent experiments were performed and similar results were obtained. Only one set of Northern blots is shown.

To check if the 5'UTR of a cytosolic GS gene has any role in regulating transcript stability or translation, gene constructs driven by the CaMV 35S promoter comprising a Gmglnβ1 coding region having or lacking its own 3'UTR and 5'UTR (FIGS. 32A and 32B) were examined by transient expression assays by means of *A. tumefaciens* infiltration of tobacco leaves (*Nicotiana tabaccum* var. *xanthi*). FIGS. 33A and 33B show transcript analysis of *Agrobacterium* infiltrated tobacco leaf samples. Four days after infiltration, the accumulation of the Gmglnβ1 mRNA was analyzed. RNA isolated from the infiltrated leaves was subjected serially to northern blot analysis using the coding region of the Gmglnβ1 gene, the 3'UTR of Gmglnβ1 gene, the NOS terminator and the NPTII gene as probes. Control tobacco plants infiltrated with *A. tumefaciens* without any plasmid did not show hybridization to any of the DNA probes. The accumulation of the NPTII mRNA was monitored to determine the efficacy of the infiltration procedure and to standardize for the Gmglnβ1 mRNA accumulation levels. As seen in FIGS. 33A and 33B, the level of hybridization in the leaf samples infiltrated with the different gene constructs showed some differences in hybridization with the NPTII probe, likely an attribute of the uniformity of the agroinfiltration, i.e. the number of cells that get the T-DNA during the process rather than position effect. The Gmglnβ1 coding region showed hybridization to all the samples infiltrated with the GS1 gene constructs, although to different levels (see FIGS. 33A and 33B). Referring to FIG. 33A, for each example, two independent plants for each construct were sampled, total RNA was isolated from 3 individual leaves from each independent plant 4 days after agroinfiltration with *A. tumefaciens* containing gene constructs of the Gmglnβ₁ gene with and without its 5' and 3'UTRs (as described in FIGS. 32A and 32B). About twenty μg of each sample was then fractionated by electrophoresis and subjected to northern blot hybridization. The blots were sequentially hybridized with $^{32}$P labeled probes corresponding to the coding region and the 3'UTR of the Gmglnβ₁ gene, the *Agrobacterium* nopaline synthetase terminator (NOS 3'UTR) and the kanamycin resistance (NPTII) gene. The 28S rRNA stained by SYBR Gold is also shown as a control for loading Quantification and standardization of the mRNA band intensities (see, FIG. 33B) showed that the Gmglnβ1 mRNA accumulation in leaves infiltrated with the gene constructs containing the 3'UTR (GSβ103 and GSβ153) was ten times lower compared to the mRNA accumulation levels of the Gmglnβ1 gene with the NOS 3'UTR (GSβ150, GSβ100). This indicates that the 3'UTR of the Gmglnβ1 gene downregulates mRNA levels at a post-transcriptional step, as has been demonstrated in stably transformed alfalfa and tobacco plants. As is also seen in FIGS. 33A and 33B, there is no difference in the transcript level for Gmglnβ1 gene in tissues infiltrated with the Gmglnβ1 gene constructs containing its own 5'UTR compared to the corresponding gene fusions in which the GS1 5'UTR was removed and replaced with the 5' noncoding region of the uidA gene of the CAMBIA 2301 (GSβ150 compared to GSβ100 and GSβ153 compared to GSβ103, FIGS. 32A and 32B). The 3'UTR of the Gmglnβ1 gene and the NOS terminator were used as probes to further distinguish between the transcript levels for the Gmglnβ1 gene in the different constructs. Hybridization with the 3'UTR and the NOS terminator as probes showed no significant difference in the intensity of the hybridization signal between the constructs with and without the 5'UTR, GSβ103 against GSβ153 and GSβ100 against GSβ150, respectively. These results indicate that the Gmglnβ1 5'UTR does not have a role in controlling GS1 transcript levels and that the 3'UTR functions independent of the 5'UTR, in controlling transcript turnover.

To check if the 5'UTR of the GS1 gene affects translation, a pattern was analyzed of GS protein accumulation and GS holoenzymes in tobacco leaves infiltrated with the different CaMV35S::Gmglnβ1 gene constructs in protein blots with antibodies against the soybean GSβ1 protein. GS is an octameric enzyme and can be either homomeric or heteromeric; based on its composition GS shows slight differences in the migration pattern on native gels. Control tobacco leaf GS1, in its native conformation migrated as a complex mixture of isoforms, probably representing different heteromeric forms (see FIG. 34A). Gmglnβ1 infiltrated samples showed another immunoreactive band in addition to the endogenous complexes seen in control samples, the level being relatively higher in the GSβ100 and GSβ150 infiltrated tissues compared to GSβ153 infiltrated tissues, in keeping with the corresponding transcript level (see FIGS. 33A and 33B). However, GSβ103 infiltrated samples showed a GS1 holoenzyme profile similar to that seen in control samples, because of the low level of expression of this gene construct. To look for quantitative differences in the steady state level of the Gmglnβ1 protein with the different gene constructs, the infiltrated tissue extracts were subjected to SDS PAGE followed by western blot analysis. The Gmglnβ1 protein comigrated with the endogenous tobacco GS1 in their denatured form. The GS1 immunoreactive band was quantified and the intensity was standardized against the average intensity of the GSβ153 gene construct, which comprises the unmodified Gmglnβ1 gene that includes its own 5'- and 3'-UTRs (FIG. 34B). The accumulation levels of the GS1 protein in the tissues infiltrated with gene constructs that lack the Gmglnβ1 3'UTR (GSβ100, GSβ150) was higher than the accumulation of GS1 in tissues infiltrated with the Gmglnβ1 constructs comprising the Gmglnβ1 3'UTR (GSβ103, GSβ153), in keeping with the corresponding transgene transcript level (FIGS. 33A and 33B). However, in spite of the fact that tissues infiltrated with GSβ150 and GSβ100 showed the same level of the transgene transcript, the GS1 accumulation levels showed differences that were statistically significant. The GSβ150 infiltrated tissues showed a 27% higher level of GS1 accumulation than GSβ100 infiltrated tissues. Similarly, the GSβ153 infiltrated tissues showed a significant 31% higher level of GS1 protein accumulation compared to GSβ103 infiltrated tissues, even though there was no difference in the level of transgene transcript accumulation. The GS2 protein levels in the denatured samples showed a reduction in the transformants compared to control plants. The same results were obtained in multiple experiments. The difference in the steady state level of the GS1 protein between tissues infiltrated with Gmglnβ1 gene constructs with or without its 5'UTR cannot be attributed to differences in transcript level (see FIGS. 33A and 33B) or to differential protein turnover since the coding sequence and hence the amino acid sequence is identical between the gene constructs. These results show that the 5'UTR plays a role in enhancing translation and that it functions independent of the 3'UTR.

Figure 35A:
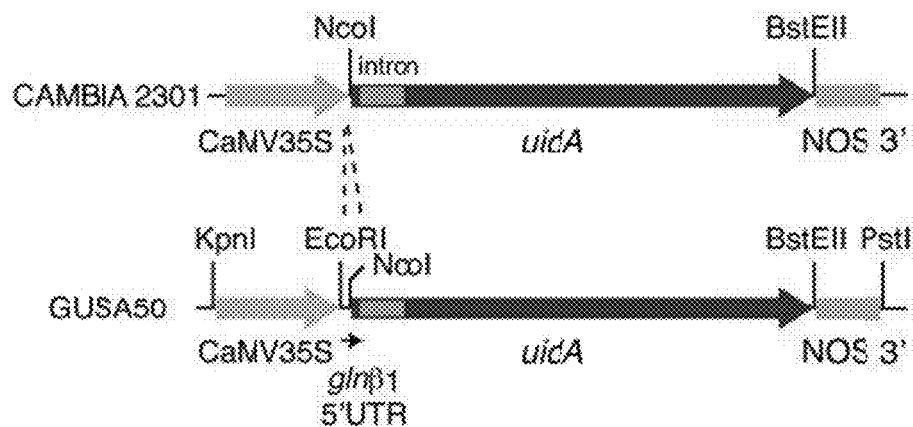
FIG. 35A shows tobacco plants were infiltrated with *A. tumefaciens* containing the CAMBIA 2301 plasmid (35SCaMV promoter::uidA reporter gene), or with the GUSA50 gene construct, which comprises the 5'UTR of the Gmglnβ$_1$ gene inserted between the CaMV 35S promoter and the uidA gene of the CAMBIA 2301 plasmid.
Figure 35B:
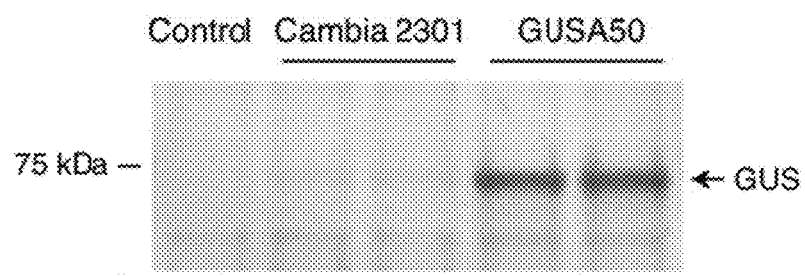
FIG. 35B shows the tobacco plants four days after infiltration protein was extracted from the tobacco leaves and about 50 µg of protein from duplicate samples was subjected to SDS PAGE followed by western blot analysis using anti-GUS antibodies. The control lane is a sample from leaves infiltrated with the CAMBIA 2300 (empty) vector.
Figure 35C:
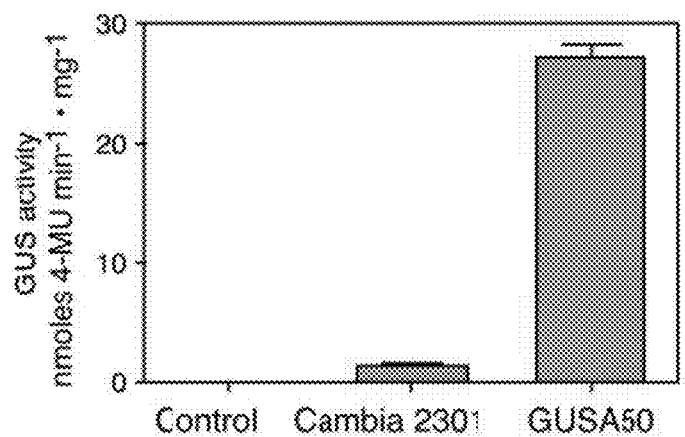
FIG. 35C shows leaf extracts from the uidA infiltrated leaves that were subjected to GUS enzyme activity determination using the fluorogenic substrate 4-MUG. The molar amount of the 4-methyl umbelliferone (4-MU) produced in the reaction was calculated against a 4-MU standard curve. The experiments were repeated three times with similar results.

To further demonstrate that the Gmglnβ1 5'-UTR has a role in enhancing translation, a gene construct was made with the 5'UTR of the Gmglnβ1 gene inserted between the CaMV 35S promoter and the β-glucuronidase reporter gene (uidA). FIGS. 35A-C show the effect of including the 5'UTR of Gmglnβ₁ in gene constructs with uidA reporter gene on the expression of β-glucuronidase (GUS) in agroinfiltrated tobacco leaves. The resulting gene construct GUSA50 and the parent CAMBIA 2301 plasmid, which comprises the uidA reporter gene driven by the CaMV 35S promoter (see FIG. 35A), were agroinfiltrated into tobacco leaves. Protein was extracted four days after infiltration and analyzed by western blotting with anti-β-glucuronidase (GUS) antibodies and measurement of its enzymatic activity (GUS activity). An immunoreactive band of 71 kDa, corresponding to the predicted size of the uidA gene product, accumulates to at least 10-fold higher accumulation level in the tissues infiltrated with GUSA50 than in the CAMBIA 2301 samples (see FIG. 35B), while the control samples infiltrated with the empty binary plasmid, CAMBIA 2300, did not show the corresponding band. GUS activity measurements showed that the inclusion of the Gmglnβ1 5'UTR in the 35SCaMV::uidA reporter gene construct increased the expression of GUS by 19.8-fold compared to the GUS expression in plants infiltrated with the original CAMBIA 2301 plasmid (FIG. 35C). The results suggest that the 5'UTR of the Gmglnβ1 gene functions as a translation enhancer independent of the coding region and the 3'UTR of the Gmglnβ1 gene.

Total RNA from tobacco leaves agroinfiltrated with the different gene constructs was reverse transcribed with an oligo-dT comprising an anchor primer, and PCR amplified with a forward primer for the Gmglnβ1 5'UTR (for constructs GSβ150 and GSβ153) or with a forward primer for the CaMV35S mRNA leader (constructs GSβ100 and GSβ103) and a reverse primer corresponding to an anchor sequence which comprises a Hind III site to preserve a continuous polyA tail. Gmglnβ1 PCR products were cloned and sequenced. RNA was then transcribed in vitro from the RT-GSβ1 clones and analyzed by subjecting equal amounts of the reaction products to electrophoresis followed by nucleic acid staining. No difference was observed in the transcript level for the different gene constructs (data not shown) indicating that the 3'UTR mediated transcript turnover does not take place in the in vitro system. Equal amounts of capped and polyadenylated RNA were then translated in a rabbit reticulocyte system and in a wheat germ system and equal amounts of the translation reaction products were analyzed by western blotting using an anti-GS1 antibody. No difference in the accumulation of the GS1 protein band translated from the different GSβ1 transcripts was seen either in the rabbit reticulocyte system (data not shown) or in the wheat germ system (see FIG. 36), indicating that the Gmglnβ1 5'UTR did not enhance translation in the in vitro system, neither the 3'UTR has an effect in the in vitro translation system.

Figure 37:
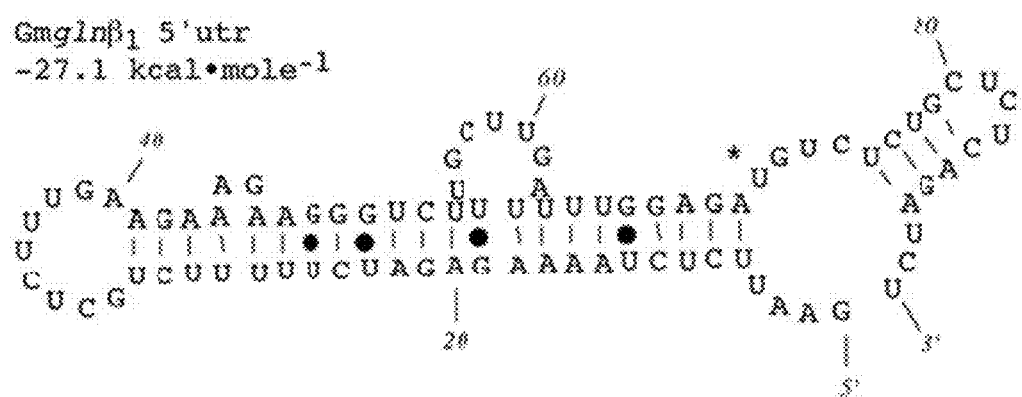
FIG. 37 shows a secondary structure of the 5'UTR of the Gmglnβ$_1$ mRNA. The optimal secondary structure of the 5'UTR, including some nucleotides in the coding region (down to a Bgl II site), was predicted by MFOLD 2.0. The predicted free energy of −27.1 kcal·mole$^{-1}$ was calculated by the UNAFold 3.8 software. The translation start codon is labeled with an asterisk.

Because of the role that the 5'UTR of the Gmglnβ1 gene plays in translation, the 5' UTR was sequenced and analyzed for any distinguishing features. The minimum energy folding of the Gmglnβ1 5'UTR shows a hairpin structure with the AUG start codon in an open unfolded region (see FIG. 37). A few features that are usually found in the non-coding regions of bacterial mRNA, were also found like a track of purines at position −20 to −32 relative to the start codon that has complementarity to the 16S rRNA in its mRNA 'track' region (see FIG. 38B). There is a partial Shine Dalgarno (SD) consensus sequence (GGAG) in the Gmglnβ1 gene at position −1 relative to the start codon. Immediately upstream of the track of purines in the Gmglnβ1 5'UTR, there is a sequence similar to the *E. coli* rrnB BoxA, which though a transcriptional antiterminator, binds the ribosomal S1 protein and acts as a translational enhancer in *E. coli*. It has been shown, that S1 is the major component of the *E. coli* ribosome directly involved in mRNA selection. Thus, the Gmglnβ1 gene transcript could be translated in the bacterial cells.

Figure 38A:
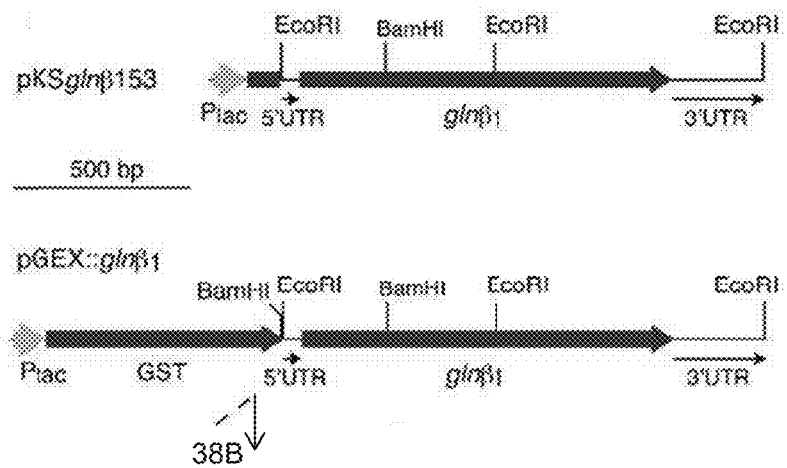
FIG. 38A shows maps of the constructs containing the Gmglnβ$_1$ gene in the pBluescript II KS (pKSglnβ153) or the pGEX-4T-2 (pGEX::glnβ$_1$) plasmids.
Figure 38B:
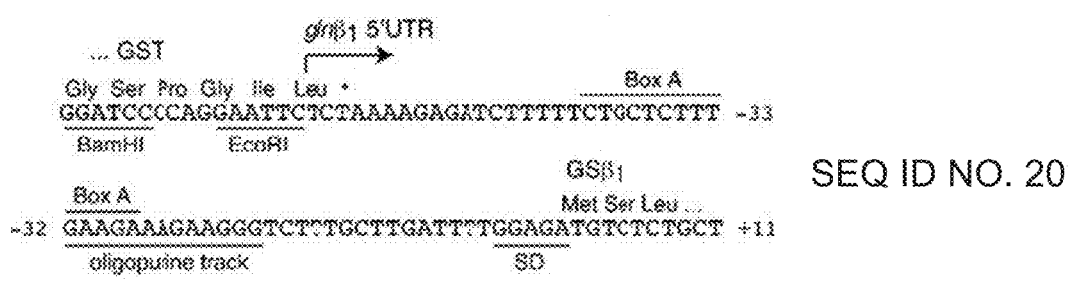
FIG. 38B shows the sequence of the GST gene and 5'UTR of the Gmglnβ$_1$ gene junction with regards to sequences that may have a role in translation initiation in prokaryotes. SD represents a Shine-Dalgarno-like sequence.
Figure 38C:
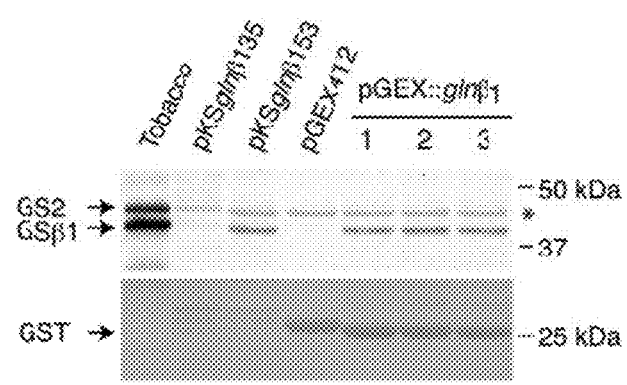
FIG. 38C shows that the expression of the plasmids comprising the Gmglnβ1 gene in the sense (pKSglnβ153 and pGEX::glnβ$_1$) or the antisense (pKSglnβ135) orientation in *E. coli*, was induced from the P$_{lac}$ or P$_{tac}$ promoters by IPTG. Proteins were extracted after two hours of induction, fractionated by electrophoresis, blotted and immunodetected using the antibodies against the soybean GSβ$_1$ protein, and against the GST protein. A sample from infiltrated tobacco leaves was included as control to indicate the migration pattern of the GSβ$_1$ protein in plants. A control sample from *E. coli* containing the pGEX-4T-2 plasmid was also included for comparison. An asterisk indicates the position of a non-specific antigenic band in *E. coli*. Lane numbers represent samples from three independent single *E. coli* colonies.

The regions, similar to bacterial translational elements, found in the 5'UTR of the Gmglnβ1 gene transcript may enable its translation in a bacterial system, the expression was analyzed in *Escherichia coli* of the plasmids containing Gmglnβ1 in the sense (pKSglnβ153) or the antisense (pKSglnβ135) orientation with respect to the P lac promoter. The expression of the Gmglnβ1 gene was induced by IPTG in exponentially growing *E. coli* XL1-Blue cultures. Induced *E. coli* proteins were extracted, subjected to SDS PAGE followed by western blotting using anti-GSβ1 antibodies. As shown in FIGS. 38A-C, the plasmid containing the full length Gmglnβ1 cDNA in the sense orientation (pKSglnβ153) expressed a protein that co-migrated with the GS1 band from a tobacco leaf sample infiltrated with the GSβ150 gene construct. The Mr of the GS1 protein produced in the bacterial system rules out the possibility of it being a β-galactosidase/GSβ1 protein fusion. Furthermore, sequence analysis showed no indication of a translational fusion with the lacZ structural gene. The results indicate that the Gmglnβ1 gene with its own 5'UTR is functional when placed under the control of a bacterial promoter, producing an mRNA that is translatable by the bacterial ribosomes.

To further confirm the potential of the Gmglnβ1 5'UTR in recruiting bacterial ribosomes, gene constructs were made with the glutathione transferase gene. The Gmglnβ1 gene with its 5'UTR and its 3'UTR was placed as a non-translational fusion downstream of the GST gene in the expression plasmid pGEX 4T 2 (FIG. 38B). The gene construct was transcribed from the IPTG inducible P tac promoter resulting in a polycistronic mRNA encoding a GST protein, eight amino acids shorter, followed by the glnβ1 5'UTR that would direct the translation of the GSβ1 protein. As seen in FIGS. 38A-C, both the GST and the GSβ1 proteins accumulate in the bacteria expressing the GST/GSβ1 constructs (pGEX::glnβ1) confirming that the Gmglnβ1 5'UTR is functional in recruiting ribosomes in a manner similar to an internal ribosomal entry site (IRES), allowing the expression of the Gmgβ1 gene. The expression of the GST protein in the pGEX::glnβ1 gene constructs is not affected, except for the fact that the GST protein is eight amino acids shorter. This is the first demonstration of the 5'UTR of an eukaryotic gene functioning as an IRES in *E. coli*.

The data presented indicates that the 5'UTR of the Gmglnβ1 gene is the determinant of translation enhancement and confirms earlier findings that the 3'UTR of the Gmglnβ1 gene controls the turnover of the transcript. A transient assay using agroinfiltration has allowed a simultaneous check of the expression of different gene constructs involving the 5' and 3'UTRs of the Gmglnβ1 gene at the level of transcript and protein accumulation. By testing gene constructs in different combinations, with and without the 3'UTR/5'UTR, it has been demonstrated that the role of the 5'UTR of the Gmglnβ1 gene in translational control and the 3'UTR in transcript turnover with both the UTRs functioning independent of each other.

Northern blot analysis using different probes, showed a 20-fold higher level of accumulation of the Gmglnβ1 transcript in the tissues infiltrated with the gene with the NOS terminator (pGSβ100 and pGSβ150) compared to tissues infiltrated with the Gmglnβ1 gene constructs containing its own 3'UTR (pGSβ103 and pGSβ153, FIGS. 33A and 33B). No differences in transcript levels were found between the samples with the gene constructs with the Gmglnβ1 5'UTR compared to the samples with the gene constructs without the 5'UTR when hybridized with either the GS1 coding region or the 3'-specific regions. The 5'UTR of the Gmglnβ1 most likely did not play a role in the 3'UTR mediated turnover of the GS1 transcript.

Figure 34A:
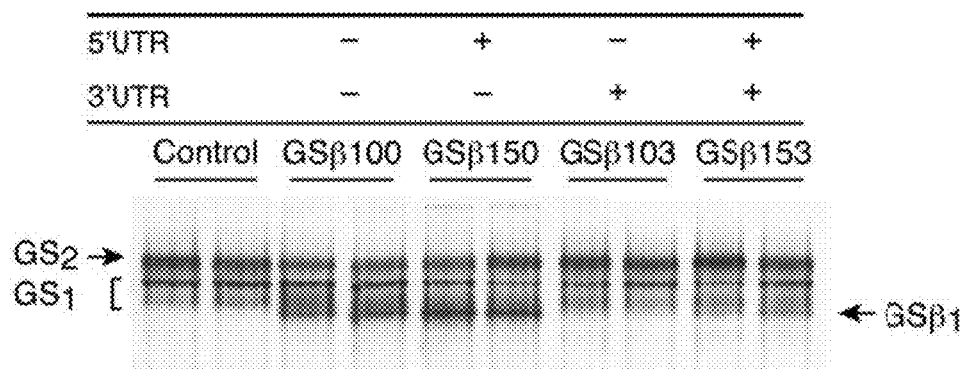
FIG. 34A shows western blot analysis of GS protein in leaf extracts of tobacco infiltrated with *A. tumefaciens* containing Gmglnβ$_1$ gene constructs with and without its 5' and 3'UTRs. Proteins were extracted from tobacco leaves 4 days after infiltration with *A. tumefaciens* containing the glnβ$_1$ gene constructs (described in FIGS. 32A and 32B). For each experiment, two individual leaves were agroinfiltrated with each gene construct. The proteins were fractionated by polyacrylamide gel electrophoresis in non-denaturing conditions (about 10 and 5 µg, respectively), followed by immunoblotting with an antibody against the soybean GSβ$_1$ protein.
Figure 34B:
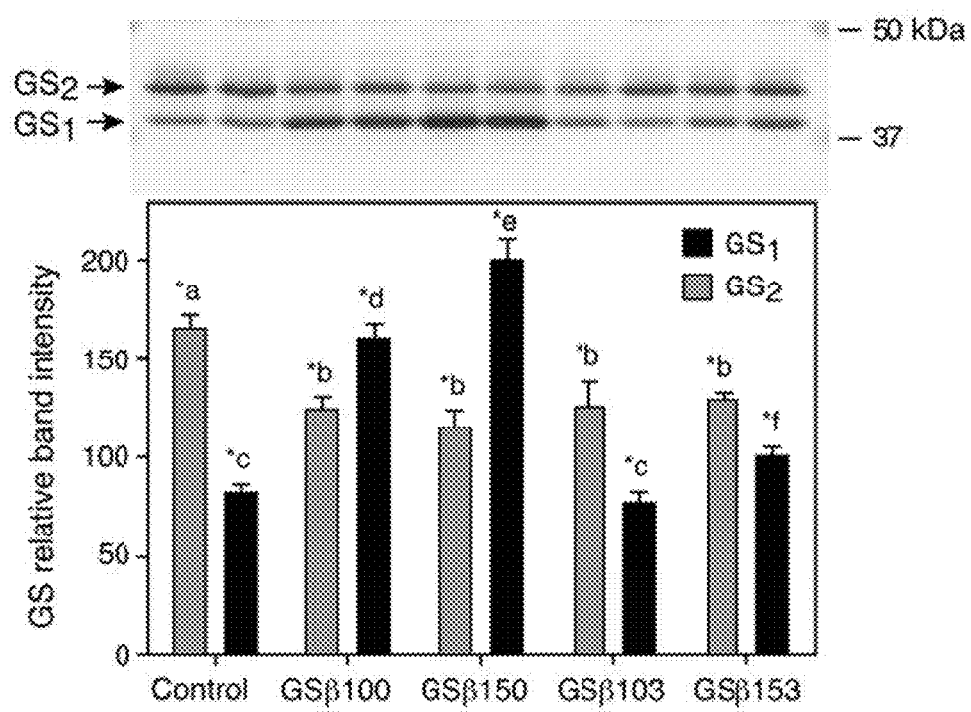
FIG. 34B shows western blot analysis of GS protein in leaf extracts of tobacco infiltrated with *A. tumefaciens* containing Gmglnβ$_1$ gene constructs with and without its 5' and 3'UTRs. Proteins were extracted from tobacco leaves 4 days after infiltration with *A. tumefaciens* containing the glnβ$_1$ gene constructs (described in FIGS. 32A and 32B). For each experiment, two individual leaves were agroinfiltrated with each gene construct. The proteins were fractionated by polyacrylamide gel electrophoresis in denaturing conditions (about 10 and 5 µg, respectively), followed by immunoblotting with an antibody against the soybean GSβ$_1$ protein. The experiment was repeated five times and the same results were obtained. The intensities of the GS$_1$ protein bands on the denaturing gel were quantified and the average intensities from five independent experiments± standard deviation were plotted. A different letter (*a-f) next to a bar means that the differences between these samples were statistically significant (P<0.05). Only one representative Western blot is shown here.

Comparison of the amounts of GS1 protein in the infiltrated tissues showed a significantly higher level of the GS1 polypeptide, 2.5-fold the amount of the endogenous GS1 levels, in the tissues infiltrated with the pGSβ150 gene construct (see FIGS. 34A and 34B). The pGSβ150 gene construct showed about 27% higher GS1 protein accumulation than with the Gmglnβ1 gene without its 5'UTR (pGSβ100). Similarly, the pGSβ153 infiltrated tissues showed a higher level of GS1 polypeptide compared to the pGSβ103 samples, with no difference in the corresponding transgene transcript level. Besides its own coding region and 3'UTR, the 5'UTR of the Gmglnβ1 transcript when placed in front of the uidA gene showed a huge increase in translation of the reporter gene, further emphasizing the role of Gmglnβ1 gene in enhancing translation. The results support the notion that the 5'UTR of the Gmglnβ1 gene functions as a translation enhancer. The 5'UTR of the Gmglnβ1 gene functions in an autonomous manner and functions as a translation enhancer independent of the coding region and the 3'UTR of the Gmglnβ1 gene. The 20-fold increase in expression level of the uidA gene with the 5'UTR of the Gmglnβ1 gene compared to the expression level of the uidA gene with its own mRNA leader (see FIGS. 35A-C), is striking when compared to the expression of the Gmglnβ1 gene with its 5'UTR which accounted for only about 27 to 31% increase in total GS1 protein accumulation, compared to the gene constructs without the 5'UTR.

The translation efficiency of mRNA is likely affected by the stability of the 5'UTR. The stem-loop region of the tobacco psbA-5'UTR and the Omega leader of the TMV RNA are important determinants of mRNA translation that act as translation enhancers because of their stable secondary and tertiary structure. The predicted secondary structure of the 5'UTR of the Gmglnβ1 is a stable hairpin with a free energy of −27.1 kcal·mole-1 that could play a role in translation enhancement (see FIG. 37).

Figure 36:
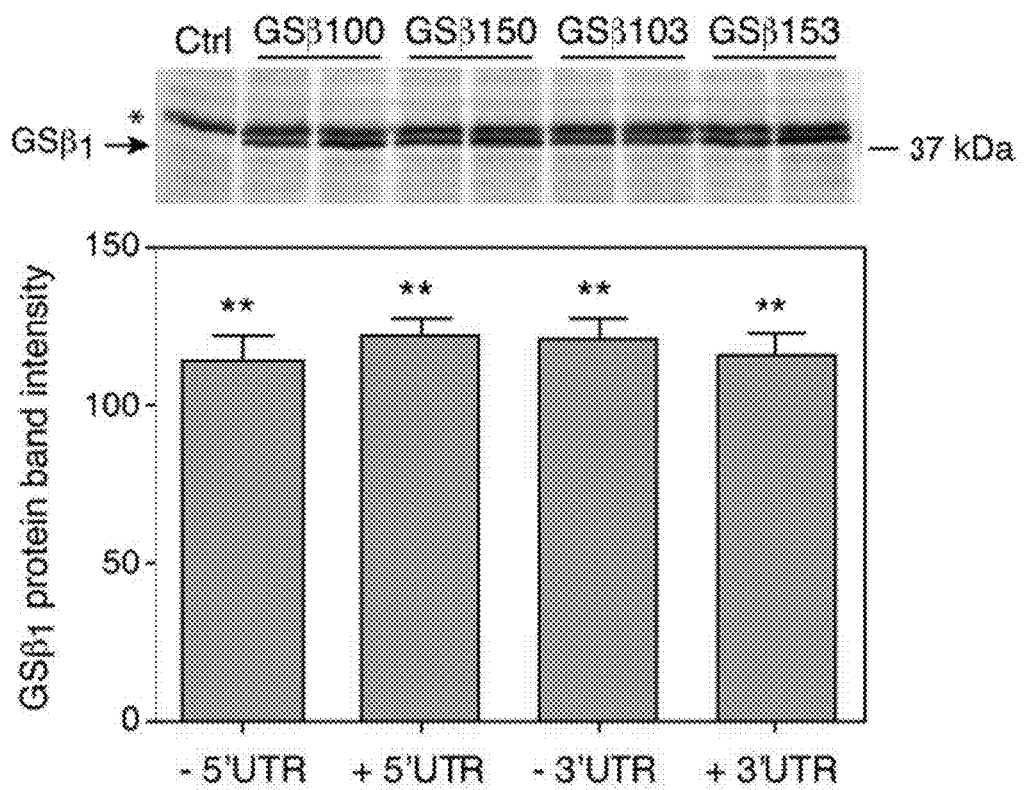
FIG. 36 shows analysis of in vitro translation products of in vitro produced transcripts corresponding to the different Gmglnβ$_1$ gene constructs (as described in FIGS. 32A and 32B). Total RNA was isolated from infiltrated tobacco leaves and reverse transcribed. GS$_1$ PCR products were further amplified from the cDNA with forward primers for the GS$_1$ 5'UTR (for constructs GSβ150 and GSβ153) or for the CaMV35S mRNA leader (constructs GSβ100 and GSβ103). RNA was in vitro transcribed from the RT-GSβ$_1$ clones and purified. Equal amounts of capped and polyadenylated RNA were translated in a wheat germ translation system and equal amounts of the translation reactions were analyzed by western blotting with an anti-GS$_1$ antibody. The position of the GSβ$_1$ immunodetected bands is indicated by an arrow. The presence of an immunoreactive band in the wheat germ extract, that may correspond to the endogenous GS$_1$, is marked with an asterisk. GSβ$_1$ protein bands were quantified and the band intensity values corresponding to the GS constructs with or without its 5'UTR/3'UTR were plotted. The in vitro transcription translation experiments were repeated three times with the same results, only a representative Western blot is shown. (*) Analysis showed that the differences in band intensities due to the presence of either the 5'UTR or the 3'UTR were not statistically significant (P<0.05).

The 5'UTR of the Gmglnβ1 gene does not function as a translation enhancer in an in vitro translation system (see FIG. 36). Indicating that some kind of factors, not present in the cell free systems but present in the leaf cells, interact with the 5'UTR of Gmglnβ1 gene to enhance translation rates ruling out the possibility of the 5'UTR acting as translational enhancer just based on its secondary structure.

Sequence analysis of the 5'UTR of the Gmglnβ1 mRNA showed a track of oligopyrimidines at −48 to −33 nucleotides upstream of the translation start codon (FIG. 32B).

FIGS. 38A-C show an expression of the Gmglnβ$_1$ gene in *Escherichia coli*. Plant glutamine synthetase genes have been expressed in *E. coli*. The GS1 and GS2 enzymes encoded by these genes are functional when expressed in bacteria, and their products correctly assemble into active native forms. However, in all cases the GS genes have been introduced as translational fusions in recombinant expression vectors. In this study example it was shown that GS1 mRNA is efficiently translated in bacteria when introduced as non-translational gene fusions, indicating that the eukaryotic 5'UTR of the Gmglnβ1 mRNA comprises the information to allow its translation in vivo in a prokaryotic system. Bacterial translational initiation involves the binding of the 30S ribosomal subunit to the ribosome binding site on the mRNA by base pairing between a Shine-Dalgarno (SD) region and the mRNA binding site (MBS) at the 3' end of the 16S rRNA. There is a partial Shine Dalgarno (SD) consensus sequence (GGAG) in the Gmglnβ1 gene at position −1 relative to the start codon (FIGS. 32A and 32B), though SD region is normally found between positions −15 to −2 relative to the start codon. There is also a track of purines at position −20 to −33 relative to the start codon that has complementarity to the 16S rRNA in its mRNA 'track' region and may have a role in translation initiation by enhancing the efficiency of recognition of the mRNA by the ribosome. Crosslinking studies have indicated that the ribosome might interact with the mRNA via alternative sites outside the SD region and the start codon. Sequences in the 16S rRNA other than the MBS, crosslink with nucleotides both upstream and downstream of the start codon, supporting the existence of alternative mechanisms of ribosome recruitment. Analyses of a large number of mRNA sequences have shown that base pairing is not the only significant factor in determining the efficiency of the expression of the mRNA. Several mRNA cis-elements have a substantial effect on the translation efficiency possibly due to its involvement in the ribosome-mRNA recognition. An alternative mechanism involves cis-acting mRNA sequences that serve as targets for the mRNA-binding ribosomal protein S1. This protein is essential for the translational machinery of Gram negative organisms and ensures the translation of mRNAs from a wide variety of sources. Immediately upstream of the track of purines in the Gmglnβ1 5'UTR, there is a sequence similar to the *E. coli* rrnB BoxA, which though a transcriptional antiterminator, binds the ribosomal S1 protein and acts as a translational enhancer. This region in the Gmglnβ1 5' UTR likely represents an efficient ribosomal S1 protein binding site. The translatability of the plant GS1 mRNA in *E. coli* indicates the working of a universal mechanism for translation initiation. The secondary structure of the 5'UTR likely prohibits translation initiation from other sites while leaving open the initiator site and allowing for the recognition by the ribosomes via the several ligands and this mechanism is universal, as shown for the GSβ1 5'UTR secondary structure (see FIG. 37).

Phylogenetic studies point to two classes of GS genes GSI and GSII. Although there are some exceptions, GSI class is found in prokaryotes, whereas the GSII class represent the functional GS genes in eukaryotes. In contrast to the endosymbiotic hypothesis which suggests the transfer of a prokaryotic gene to the nuclei in plants during the establishment of the endosymbiosis, the phylogenetic studies show that the GS genes involved in organelle function diverged long after the endosymbiosis from a common ancestor GSII type gene. It is thus unlikely that the remnants of translational elements in the plant GS which may function in *E. coli* are from bacterial origin. The presence of these translation initiation elements in the GS1 rather indicate that the mechanisms of translation initiation are conserved between prokaryotes and eukaryotes, as it has been shown.

The ability of the Gmglnβ1 5'UTR to enhance translation of a protein coding region, is of great biotechnological significance in that plant cells can be just as efficient in the synthesis of a foreign protein as bacterial cells. Moreover, plant cells are more ideal for proteins that undergo post-translational modification. The translational enhancement property of the Gmglnβ1 5'UTR on the reporter gene is also very useful for checking the functionality of weak promoters.

The preceding examples can be repeated with similar success by substituting the generically or specifically described reactants and/or operating conditions of this invention for those used in the preceding examples.

Note that in the specification and claims, "about" or "approximately" means within twenty percent (20%) of the numerical amount cited.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

The invention claimed is:

1. A transgenic leguminous plant, plant tissue or plant cell comprising a first expressible nucleic acid sequence encoding the sucrose phosphate synthase (SPS) gene of maize, said plant, plant tissue or plant cell expressing increased levels of SPS, which catalyzes sucrose synthesis, wherein said first expressible nucleic acid comprises 95% sequence identity with SEQ ID NO: 1, and a second expressible nucleic acid sequence encoding the Glutamine synthetase (GS) gene of soybean, said plant, plant tissue or plant cell expressing increased nitrogen metabolism, wherein said second nucleic acid comprises at least 95% sequence identity with SEQ ID NO: 2, wherein the 3' UTR of SEQ ID NO: 2 is excluded.

2. The transgenic leguminous plant, plant tissue or plant cell of claim 1 wherein said first and second expressible nucleic acid sequences are under the control of one or more promoters.

3. The transgenic leguminous plant, plant tissue or plant cell of claim 2 wherein said promoters are CaMV 35S.

4. The transgenic leguminous plant, plant tissue or plant cell of claim 1 wherein said first expressible nucleic acid sequence comprises 100% sequence identity with SEQ ID NO: 1.

5. The transgenic leguminous plant, plant tissue or plant cell of claim 4 wherein said first and second expressible nucleic acid sequences are under the control of one or more promoters.

6. The transgenic leguminous plant, plant tissue or plant cell of claim 5 wherein said promoters are CaMV 35S.

7. The transgenic leguminous plant, plant tissue or plant cell of claim 1 wherein said second expressible nucleic acid sequence comprises 100% sequence identity with SEQ ID NO: 2, wherein the 3' UTR of SEQ ID NO: 2 is excluded.

8. The transgenic leguminous plant, plant tissue or plant cell of claim 7 wherein said first and second expressible nucleic acid sequences are under the control of one or more promoters.

9. The transgenic leguminous plant, plant tissue or plant cell of claim 8 wherein said promoters are CaMV 35S.

10. The transgenic leguminous plant, plant tissue or plant cell of claim 1 wherein said first expressible nucleic acid sequence comprises 100% sequence identity with SEQ ID NO: 1; and said second expressible nucleic acid sequence comprises 100% sequence identity with SEQ ID NO: 2, wherein the 3' UTR of SEQ ID NO: 2 is excluded.

11. The transgenic leguminous plant, plant tissue or plant cell of claim 9 wherein said first and second expressible nucleic acid sequences are under the control of one or more promoters.

12. The transgenic leguminous plant, plant tissue or plant cell of claim 11 wherein said promoters are CaMV 35S.

* * * * *